United States Patent
Keller et al.

(10) Patent No.: US 10,718,018 B2
(45) Date of Patent: Jul. 21, 2020

(54) COMPLEX SETS OF MIRNAS AS NON-INVASIVE BIOMARKERS FOR DILATED CARDIOMYOPATHY

(75) Inventors: Andreas Keller, Püttlingen (DE); Benjamin Meder, Dossenheim (DE); Hugo Katus, Heidelberg (DE); Britta Vogel, Heidelberg (DE); Markus Beier, Weinheim (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 0 days.

(21) Appl. No.: 14/124,264

(22) PCT Filed: Jun. 8, 2012

(86) PCT No.: PCT/EP2012/060927
§ 371 (c)(1),
(2), (4) Date: Dec. 6, 2013

(87) PCT Pub. No.: WO2012/168448
PCT Pub. Date: Dec. 13, 2012

(65) Prior Publication Data
US 2014/0194312 A1    Jul. 10, 2014

(30) Foreign Application Priority Data
Jun. 8, 2011 (EP) .................................. 11169192

(51) Int. Cl.
*C12Q 1/6883* (2018.01)
(52) U.S. Cl.
CPC ..... *C12Q 1/6883* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

| 9,758,827 B2 * | 9/2017 | Keller .................. C12Q 1/6809 |
| 2011/0152352 A1 * | 6/2011 | Hata ..................... C12N 15/111 |
| | | 514/44 A |

FOREIGN PATENT DOCUMENTS

WO    WO 2010/139810    * 12/2010

OTHER PUBLICATIONS

The Agilent Gene Expression Platform. Agilent Technologies, Nov. 18, 2010.*
European Communication Pursuant to Article 94(3) EPC, Application No. EP 16151269.4, dated Dec. 5, 2016.
Voellenkle et al., "MicroRNA signatures in peripheral blood mononuclear cells of chronic heart failure patients", 2010, vol. 42, pp. 420-426.

* cited by examiner

*Primary Examiner* — Channing S Mahatan
(74) *Attorney, Agent, or Firm* — MacMillan, Sobanski & Todd, LLC

(57) ABSTRACT

The present invention relates to non-invasive methods, kits and means for diagnosing and/or prognosing of dilated cardiomyopathy in a body fluid sample from a subject. Further, the present invention relates to set of polynucleotides or sets of primer pairs for detecting sets of miRNAs for diagnosing and/or prognosing of dilated cardiomyopathy in a body fluid sample from a subject. In addition, the present invention relates to sets of miRNAs for diagnosing and/or prognosing of dilated cardiomyopathy in a body fluid sample from a subject.

2 Claims, 23 Drawing Sheets
Specification includes a Sequence Listing.

| miRNA | median g1 | median g2 | qmedian | logqmedian | wmw_rawp | wmw_adjp | ttest_rawp | ttest_adjp | AUC | limma_rawp | limma_adjp |
|---|---|---|---|---|---|---|---|---|---|---|---|
| hsa-miR-520d-5p | 59 | 90 | 0.66 | -0.41 | 3.19E-04 | 2.61E-01 | 3.99E-04 | 3.53E-01 | 0.28 | 4.96E-03 | 4.66E-01 |
| hsa-miR-548i | 7 | 28 | 0.24 | -1.44 | 1.68E-03 | 2.96E-01 | 8.23E-04 | 3.63E-01 | 0.31 | 1.43E-03 | 3.44E-01 |
| hsa-miR-122* | 79 | 104 | 0.75 | -0.28 | 1.18E-03 | 2.61E-01 | 1.51E-03 | 4.44E-01 | 0.30 | 1.98E-03 | 3.50E-01 |
| hsa-miR-345 | 151 | 118 | 1.28 | 0.25 | 4.97E-03 | 3.99E-01 | 2.47E-03 | 4.84E-01 | 0.67 | 9.25E-03 | 5.45E-01 |
| hsa-miR-1225-5p | 126 | 155 | 0.81 | -0.21 | 1.15E-02 | 4.79E-01 | 3.14E-03 | 4.84E-01 | 0.34 | 4.91E-03 | 4.66E-01 |
| hsa-miR-558 | 106 | 63 | 1.70 | 0.53 | 8.86E-04 | 2.61E-01 | 4.17E-03 | 4.84E-01 | 0.70 | 1.37E-02 | 5.54E-01 |
| hsa-miR-1302 | 30 | 10 | 3.02 | 1.11 | 2.39E-03 | 3.47E-01 | 4.59E-03 | 4.84E-01 | 0.68 | 2.57E-03 | 3.78E-01 |
| hsa-miR-760 | 53 | 26 | 2.02 | 0.70 | 3.88E-03 | 3.47E-01 | 4.80E-03 | 4.84E-01 | 0.68 | 2.11E-02 | 6.45E-01 |
| hsa-let-7e* | 9 | 37 | 0.25 | -1.39 | 2.92E-03 | 3.47E-01 | 4.93E-03 | 4.84E-01 | 0.32 | 1.17E-03 | 3.44E-01 |
| hsa-miR-1301 | 215 | 191 | 1.12 | 0.12 | 9.02E-03 | 4.79E-01 | 6.84E-03 | 5.67E-01 | 0.66 | 5.99E-03 | 4.66E-01 |
| hsa-miR-422a | 243 | 284 | 0.86 | -0.15 | 2.46E-02 | 7.42E-01 | 7.74E-03 | 5.67E-01 | 0.36 | 6.02E-03 | 4.66E-01 |
| hsa-miR-551b* | 58 | 77 | 0.75 | -0.28 | 9.23E-03 | 4.79E-01 | 8.34E-03 | 5.67E-01 | 0.34 | 5.00E-02 | 7.05E-01 |
| hsa-miR-604 | 97 | 63 | 1.53 | 0.43 | 9.66E-03 | 4.79E-01 | 9.12E-03 | 5.67E-01 | 0.66 | 5.54E-02 | 7.05E-01 |
| hsa-miR-200b* | 67 | 88 | 0.76 | -0.27 | 1.77E-02 | 6.27E-01 | 9.88E-03 | 5.67E-01 | 0.35 | 9.06E-03 | 5.45E-01 |
| hsa-miR-146b-3p | 89 | 67 | 1.33 | 0.28 | 3.93E-03 | 3.47E-01 | 1.00E-02 | 5.67E-01 | 0.68 | 9.07E-02 | 7.72E-01 |
| hsa-miR-944 | 31 | 48 | 0.65 | -0.44 | 1.77E-02 | 6.27E-01 | 1.03E-02 | 5.67E-01 | 0.35 | 3.68E-02 | 7.05E-01 |
| hsa-miR-892a | 16 | 29 | 0.56 | -0.59 | 2.52E-02 | 7.42E-01 | 1.18E-02 | 6.11E-01 | 0.36 | 5.56E-02 | 7.05E-01 |
| hsa-miR-218 | 46 | 28 | 1.63 | 0.49 | 6.65E-03 | 4.79E-01 | 1.26E-02 | 6.18E-01 | 0.67 | 1.08E-02 | 5.54E-01 |
| hsa-miR-224 | 80 | 103 | 0.77 | -0.26 | 1.06E-02 | 4.79E-01 | 1.48E-02 | 6.86E-01 | 0.34 | 1.35E-01 | 8.00E-01 |
| hsa-miR-30a | 467 | 607 | 0.77 | -0.26 | 5.34E-02 | 8.34E-01 | 1.77E-02 | 6.86E-01 | 0.38 | 7.01E-02 | 7.05E-01 |
| hsa-miR-643 | 31 | 47 | 0.66 | -0.41 | 1.03E-02 | 2.61E-01 | 2.05E-02 | 6.86E-01 | 0.30 | 1.56E-03 | 3.44E-01 |
| hsa-miR-566 | 125 | 107 | 1.17 | 0.16 | 4.82E-02 | 8.34E-01 | 2.06E-02 | 6.86E-01 | 0.62 | 6.16E-02 | 7.05E-01 |
| hsa-let-7g* | 141 | 129 | 1.10 | 0.09 | 4.60E-02 | 8.34E-01 | 2.14E-02 | 6.86E-01 | 0.62 | 6.84E-02 | 7.05E-01 |
| hsa-miR-622 | 82 | 108 | 0.76 | -0.27 | 2.17E-02 | 7.10E-01 | 2.18E-02 | 6.86E-01 | 0.36 | 1.27E-02 | 5.54E-01 |
| hsa-miR-331-5p | 23 | 43 | 0.53 | -0.63 | 1.15E-02 | 4.79E-01 | 2.23E-02 | 6.86E-01 | 0.35 | 4.73E-03 | 4.66E-01 |
| hsa-miR-767-5p | 181 | 173 | 1.04 | 0.04 | 1.02E-01 | 8.34E-01 | 2.28E-02 | 6.86E-01 | 0.60 | 1.31E-01 | 8.00E-01 |
| hsa-miR-1231 | 119 | 140 | 0.85 | -0.16 | 5.24E-02 | 8.34E-01 | 2.31E-02 | 6.86E-01 | 0.38 | 1.17E-02 | 5.54E-01 |
| hsa-miR-551b | 84 | 66 | 1.26 | 0.23 | 3.07E-02 | 8.21E-01 | 2.36E-02 | 6.86E-01 | 0.63 | 4.97E-02 | 7.05E-01 |

FIGURE 1

| miRNA | | | | | | | | | | | |
|---|---|---|---|---|---|---|---|---|---|---|---|
| hsa-miR-140-5p | 20 | 34 | 0.60 | -0.52 | 3.84E-02 | 8.34E-01 | 2.45E-02 | 6.86E-01 | 0.37 | 5.16E-02 | 7.05E-01 |
| hsa-miR-1228* | 2184 | 2492 | 0.88 | -0.13 | 8.56E-02 | 8.34E-01 | 2.48E-02 | 6.86E-01 | 0.39 | 9.68E-02 | 7.72E-01 |
| hsa-miR-1914 | 71 | 58 | 1.23 | 0.21 | 5.19E-02 | 8.34E-01 | 2.50E-02 | 6.86E-01 | 0.62 | 8.75E-03 | 5.45E-01 |
| hsa-miR-144 | 2492 | 2092 | 1.19 | 0.17 | 4.18E-02 | 8.34E-01 | 2.74E-02 | 6.86E-01 | 0.62 | 4.65E-02 | 7.05E-01 |
| hsa-miR-141* | 65 | 88 | 0.74 | -0.30 | 5.49E-02 | 8.34E-01 | 2.82E-02 | 6.86E-01 | 0.38 | 4.16E-01 | 8.76E-01 |
| hsa-miR-519e* | 63 | 89 | 0.71 | -0.35 | 2.98E-02 | 8.21E-01 | 2.83E-02 | 6.86E-01 | 0.37 | 1.10E-03 | 3.44E-01 |
| hsa-miR-1322 | 174 | 147 | 1.18 | 0.17 | 6.92E-02 | 8.34E-01 | 2.96E-02 | 6.86E-01 | 0.61 | 8.40E-02 | 7.57E-01 |
| hsa-miR-99a* | 63 | 79 | 0.80 | -0.22 | 4.19E-02 | 8.34E-01 | 3.02E-02 | 6.86E-01 | 0.38 | 3.79E-02 | 7.05E-01 |
| hsa-miR-520d-3p | 25 | 22 | 1.15 | 0.14 | 1.98E-01 | 8.54E-01 | 3.11E-02 | 6.86E-01 | 0.58 | 2.88E-01 | 8.76E-01 |
| hsa-miR-19a* | 20 | 38 | 0.51 | -0.66 | 1.13E-01 | 8.34E-01 | 3.11E-02 | 6.86E-01 | 0.40 | 4.03E-01 | 8.76E-01 |
| hsa-miR-1183 | 108 | 98 | 1.10 | 0.10 | 6.17E-02 | 8.34E-01 | 3.19E-02 | 6.86E-01 | 0.61 | 2.76E-02 | 6.97E-01 |
| hsa-miR-493* | 41 | 45 | 0.91 | -0.10 | 8.34E-02 | 8.34E-01 | 3.19E-02 | 6.86E-01 | 0.39 | 4.51E-01 | 8.76E-01 |
| hsa-miR-323-5p | 51 | 43 | 1.19 | 0.17 | 6.16E-02 | 8.34E-01 | 3.28E-02 | 6.86E-01 | 0.61 | 5.71E-02 | 7.05E-01 |
| hsa-miR-147 | 43 | 29 | 1.47 | 0.39 | 5.44E-02 | 8.34E-01 | 3.34E-02 | 6.86E-01 | 0.62 | 9.65E-02 | 7.72E-01 |
| hsa-miR-19b | 18244 | 21472 | 0.85 | -0.16 | 4.70E-02 | 8.34E-01 | 3.38E-02 | 6.86E-01 | 0.38 | 5.77E-02 | 7.05E-01 |
| hsa-miR-376a | 73 | 112 | 0.65 | -0.44 | 9.55E-03 | 4.79E-01 | 3.50E-02 | 6.86E-01 | 0.34 | 8.20E-02 | 7.54E-01 |
| hsa-miR-455-3p | 181 | 178 | 1.01 | 0.01 | 1.64E-01 | 8.39E-01 | 3.53E-02 | 6.86E-01 | 0.59 | 4.86E-02 | 7.05E-01 |
| hsa-miR-143* | 139 | 105 | 1.33 | 0.29 | 4.43E-02 | 8.34E-01 | 3.73E-02 | 6.86E-01 | 0.62 | 4.38E-02 | 7.05E-01 |
| hsa-miR-597 | 50 | 43 | 1.17 | 0.15 | 6.25E-02 | 8.34E-01 | 3.76E-02 | 6.86E-01 | 0.61 | 5.22E-02 | 7.05E-01 |
| hsa-miR-367* | 45 | 30 | 1.50 | 0.40 | 6.58E-02 | 8.34E-01 | 3.82E-02 | 6.86E-01 | 0.61 | 4.60E-01 | 8.76E-01 |
| hsa-miR-578 | 1 | 1 | 1.39 | 0.33 | 1.10E-01 | 8.34E-01 | 3.85E-02 | 6.86E-01 | 0.59 | 1.25E-01 | 8.00E-01 |
| hsa-miR-668 | 63 | 73 | 0.86 | -0.15 | 5.49E-02 | 8.34E-01 | 3.94E-02 | 6.86E-01 | 0.38 | 2.19E-02 | 6.45E-01 |
| hsa-miR-623 | 65 | 55 | 1.20 | 0.18 | 3.34E-02 | 8.34E-01 | 3.96E-02 | 6.86E-01 | 0.63 | 1.38E-02 | 5.54E-01 |
| hsa-miR-563 | 1 | 6 | 0.16 | -1.82 | 1.38E-01 | 8.34E-01 | 4.19E-02 | 7.12E-01 | 0.41 | 1.60E-01 | 8.00E-01 |
| hsa-miR-582-3p | 93 | 121 | 0.77 | -0.26 | 2.48E-02 | 7.42E-01 | 4.43E-02 | 7.38E-01 | 0.36 | 1.11E-01 | 7.93E-01 |
| hsa-miR-19a | 4160 | 3618 | 1.15 | 0.14 | 5.97E-02 | 8.34E-01 | 4.64E-02 | 7.38E-01 | 0.62 | 6.40E-02 | 7.05E-01 |
| hsa-miR-369-3p | 26 | 43 | 0.61 | -0.50 | 1.29E-02 | 4.95E-01 | 4.70E-02 | 7.38E-01 | 0.35 | 6.33E-03 | 4.66E-01 |
| hsa-miR-670 | 30 | 58 | 0.52 | -0.65 | 1.19E-02 | 4.79E-01 | 4.94E-02 | 7.38E-01 | 0.35 | 3.53E-02 | 7.05E-01 |
| hsa-miR-1272 | 132 | 106 | 1.24 | 0.21 | 6.51E-02 | 8.34E-01 | 5.03E-02 | 7.38E-01 | 0.61 | 3.03E-02 | 7.03E-01 |
| hsa-miR-2278 | 86 | 73 | 1.18 | 0.17 | 1.22E-01 | 8.34E-01 | 5.16E-02 | 7.38E-01 | 0.59 | 7.25E-02 | 7.05E-01 |

FIGURE 1 cont.

| | | | | | | | | | | |
|---|---|---|---|---|---|---|---|---|---|---|
| hsa-miR-1289 | 103 | 85 | 1.20 | 0.19 | 7.54E-02 | 8.34E-01 | 5.16E-02 | 7.38E-01 | 0.61 | 1.61E-01 | 8.00E-01 |
| hsa-miR-1255b | 103 | 105 | 0.99 | -0.01 | 1.68E-01 | 8.39E-01 | 5.23E-02 | 7.38E-01 | 0.42 | 2.26E-02 | 6.45E-01 |
| hsa-miR-616 | 22 | 38 | 0.59 | -0.54 | 1.35E-01 | 8.34E-01 | 5.45E-02 | 7.38E-01 | 0.41 | 3.18E-01 | 8.76E-01 |
| hsa-miR-516b* | 16 | 21 | 0.79 | -0.24 | 1.33E-01 | 8.34E-01 | 5.80E-02 | 7.38E-01 | 0.41 | 1.41E-01 | 8.00E-01 |
| hsa-miR-628-3p | 381 | 363 | 1.05 | 0.05 | 1.43E-01 | 8.34E-01 | 5.80E-02 | 7.38E-01 | 0.41 | 1.08E-01 | 7.93E-01 |
| hsa-miR-1271 | 209 | 243 | 0.86 | -0.15 | 5.44E-02 | 8.34E-01 | 5.95E-02 | 7.38E-01 | 0.38 | 1.94E-02 | 6.45E-01 |
| hsa-miR-338-5p | 52 | 63 | 0.83 | -0.19 | 9.63E-02 | 8.34E-01 | 6.00E-02 | 7.38E-01 | 0.40 | 1.07E-01 | 7.93E-01 |
| hsa-miR-379* | 69 | 88 | 0.78 | -0.25 | 9.87E-02 | 8.34E-01 | 6.18E-02 | 7.38E-01 | 0.40 | 3.62E-01 | 8.76E-01 |
| hsa-miR-449c | 22 | 16 | 1.37 | 0.31 | 1.39E-01 | 8.34E-01 | 6.39E-02 | 7.38E-01 | 0.59 | 2.91E-01 | 8.76E-01 |
| hsa-miR-561 | 32 | 26 | 1.22 | 0.20 | 2.86E-01 | 8.64E-01 | 6.43E-02 | 7.38E-01 | 0.57 | 3.43E-01 | 8.76E-01 |
| hsa-miR-513a-5p | 86 | 64 | 1.34 | 0.29 | 3.92E-02 | 8.34E-01 | 6.44E-02 | 7.38E-01 | 0.63 | 7.04E-01 | 9.22E-01 |
| hsa-miR-522* | 163 | 145 | 1.13 | 0.12 | 8.79E-02 | 8.34E-01 | 6.53E-02 | 7.38E-01 | 0.60 | 1.57E-01 | 8.00E-01 |
| hsa-miR-539 | 7 | 16 | 0.46 | -0.78 | 1.03E-01 | 8.34E-01 | 6.64E-02 | 7.38E-01 | 0.40 | 9.33E-02 | 7.72E-01 |
| hsa-miR-1227 | 84 | 102 | 0.82 | -0.20 | 1.69E-01 | 8.39E-01 | 6.68E-02 | 7.38E-01 | 0.42 | 1.84E-02 | 6.45E-01 |
| hsa-miR-367 | 82 | 93 | 0.88 | -0.12 | 8.15E-02 | 8.34E-01 | 6.98E-02 | 7.38E-01 | 0.39 | 1.96E-01 | 8.55E-01 |
| hsa-miR-509-3p | 20 | 6 | 3.03 | 1.11 | 1.56E-01 | 8.39E-01 | 7.01E-02 | 7.38E-01 | 0.59 | 1.59E-01 | 8.00E-01 |
| hsa-miR-30c-2* | 41 | 43 | 0.96 | -0.04 | 2.55E-01 | 8.54E-01 | 7.03E-02 | 7.38E-01 | 0.57 | 1.32E-02 | 5.54E-01 |
| hsa-miR-625* | 228 | 250 | 0.91 | -0.09 | 1.33E-01 | 8.34E-01 | 7.30E-02 | 7.38E-01 | 0.41 | 1.64E-01 | 8.00E-01 |
| hsa-miR-520a-5p | 145 | 151 | 0.96 | -0.04 | 2.39E-01 | 8.54E-01 | 7.35E-02 | 7.38E-01 | 0.43 | 2.40E-02 | 6.45E-01 |
| hsa-miR-92a | 12974 | 11182 | 1.16 | 0.15 | 7.77E-02 | 8.34E-01 | 7.41E-02 | 7.38E-01 | 0.61 | 1.54E-01 | 8.00E-01 |
| hsa-miR-658 | 96 | 109 | 0.89 | -0.12 | 1.70E-01 | 8.41E-01 | 7.44E-02 | 7.38E-01 | 0.42 | 5.44E-02 | 7.05E-01 |
| hsa-miR-221* | 85 | 85 | 0.99 | -0.01 | 1.15E-01 | 8.34E-01 | 7.56E-02 | 7.38E-01 | 0.40 | 1.33E-02 | 5.54E-01 |
| hsa-miR-485-5p | 40 | 26 | 1.52 | 0.42 | 1.45E-01 | 8.34E-01 | 7.59E-02 | 7.38E-01 | 0.59 | 4.08E-01 | 8.76E-01 |
| hsa-miR-583 | 45 | 53 | 0.85 | -0.16 | 2.49E-01 | 8.54E-01 | 7.59E-02 | 7.38E-01 | 0.43 | 9.88E-02 | 7.72E-01 |
| hsa-miR-211 | 1 | 1 | 1.00 | 0.00 | 3.72E-01 | 8.81E-01 | 7.63E-02 | 7.38E-01 | 0.55 | 2.89E-01 | 8.76E-01 |
| hsa-miR-1207-3p | 53 | 33 | 1.60 | 0.47 | 1.77E-01 | 8.51E-01 | 7.64E-02 | 7.38E-01 | 0.58 | 2.81E-01 | 8.76E-01 |
| hsa-miR-518c* | 79 | 93 | 0.84 | -0.17 | 1.27E-01 | 8.34E-01 | 7.64E-02 | 7.38E-01 | 0.41 | 7.26E-01 | 9.31E-01 |
| hsa-miR-340 | 440 | 491 | 0.90 | -0.11 | 1.20E-01 | 8.34E-01 | 7.74E-02 | 7.38E-01 | 0.40 | 9.80E-02 | 7.72E-01 |
| hsa-miR-559 | 40 | 49 | 0.80 | -0.22 | 1.20E-01 | 8.34E-01 | 7.86E-02 | 7.38E-01 | 0.40 | 4.03E-02 | 7.05E-01 |
| hsa-miR-1282 | 1 | 1 | 1.00 | 0.00 | 1.61E-01 | 8.39E-01 | 8.01E-02 | 7.38E-01 | 0.57 | 1.07E-01 | 7.93E-01 |

FIGURE 1 cont.

| | | | | | | | | | | |
|---|---|---|---|---|---|---|---|---|---|---|
| hsa-miR-671-5p | 55 | 64 | 0.86 | -0.15 | 8.29E-02 | 8.34E-01 | 8.11E-02 | 7.38E-01 | 0.39 | 3.50E-01 | 8.76E-01 |
| hsa-miR-1179 | 4 | 13 | 0.34 | -1.08 | 8.93E-02 | 8.34E-01 | 8.13E-02 | 7.38E-01 | 0.40 | 9.35E-02 | 7.72E-01 |
| hsa-miR-1321 | 46 | 26 | 1.78 | 0.58 | 3.99E-02 | 8.34E-01 | 8.17E-02 | 7.38E-01 | 0.63 | 3.32E-02 | 7.05E-01 |
| hsa-miR-1304 | 58 | 70 | 0.83 | -0.19 | 2.54E-01 | 8.54E-01 | 8.18E-02 | 7.38E-01 | 0.43 | 3.59E-02 | 7.05E-01 |
| hsa-miR-365 | 61 | 81 | 0.75 | -0.28 | 8.22E-02 | 8.34E-01 | 8.28E-02 | 7.38E-01 | 0.39 | 2.41E-02 | 6.45E-01 |
| hsa-miR-34a* | 83 | 62 | 1.32 | 0.28 | 6.66E-02 | 8.34E-01 | 8.37E-02 | 7.38E-01 | 0.61 | 4.10E-01 | 8.76E-01 |
| hsa-miR-127-3p | 79 | 64 | 1.24 | 0.21 | 2.34E-01 | 8.54E-01 | 8.42E-02 | 7.38E-01 | 0.57 | 1.18E-01 | 8.00E-01 |
| hsa-miR-21* | 89 | 105 | 0.85 | -0.17 | 9.01E-02 | 8.34E-01 | 8.42E-02 | 7.38E-01 | 0.40 | 3.60E-02 | 7.05E-01 |
| hsa-miR-32* | 1 | 1 | 1.00 | 0.00 | 2.63E-01 | 8.59E-01 | 8.42E-02 | 7.38E-01 | 0.44 | 1.61E-01 | 8.00E-01 |
| hsa-let-7f-2* | 30 | 20 | 1.49 | 0.40 | 1.09E-01 | 8.34E-01 | 8.47E-02 | 7.38E-01 | 0.60 | 1.19E-01 | 8.00E-01 |
| hsa-miR-30e | 325 | 355 | 0.92 | -0.09 | 2.44E-01 | 8.54E-01 | 8.52E-02 | 7.38E-01 | 0.43 | 1.96E-01 | 8.55E-01 |
| hsa-miR-516b | 26 | 1 | 25.52 | 3.24 | 6.06E-02 | 8.34E-01 | 8.59E-02 | 7.38E-01 | 0.61 | 6.46E-02 | 7.05E-01 |
| hsa-miR-569 | 19 | 26 | 0.75 | -0.29 | 1.02E-01 | 8.34E-01 | 8.66E-02 | 7.38E-01 | 0.40 | 5.79E-02 | 7.05E-01 |
| hsa-miR-609 | 7 | 1 | 7.30 | 1.99 | 1.69E-01 | 8.39E-01 | 8.73E-02 | 7.38E-01 | 0.58 | 1.66E-01 | 8.00E-01 |
| hsa-miR-605 | 36 | 22 | 1.63 | 0.49 | 8.54E-02 | 8.34E-01 | 8.75E-02 | 7.38E-01 | 0.61 | 6.93E-02 | 7.05E-01 |
| hsa-miR-617 | 15 | 26 | 0.59 | -0.52 | 1.32E-01 | 8.34E-01 | 8.93E-02 | 7.38E-01 | 0.41 | 2.00E-01 | 8.55E-01 |
| hsa-miR-30d | 7738 | 8683 | 0.89 | -0.12 | 6.02E-02 | 8.34E-01 | 8.99E-02 | 7.38E-01 | 0.38 | 2.10E-01 | 8.55E-01 |
| hsa-miR-1277 | 61 | 73 | 0.83 | -0.18 | 1.40E-01 | 8.34E-01 | 9.02E-02 | 7.38E-01 | 0.41 | 1.47E-01 | 8.00E-01 |
| hsa-miR-370 | 74 | 53 | 1.40 | 0.33 | 3.96E-02 | 8.34E-01 | 9.04E-02 | 7.38E-01 | 0.63 | 1.61E-01 | 8.00E-01 |
| hsa-miR-545* | 11 | 1 | 10.98 | 2.40 | 3.53E-02 | 8.34E-01 | 9.06E-02 | 7.38E-01 | 0.62 | 5.41E-02 | 7.05E-01 |
| hsa-miR-548h | 20 | 13 | 1.54 | 0.43 | 4.91E-02 | 8.34E-01 | 9.15E-02 | 7.38E-01 | 0.62 | 6.71E-02 | 7.05E-01 |
| hsa-miR-26b* | 40 | 26 | 1.52 | 0.42 | 2.55E-01 | 8.54E-01 | 9.19E-02 | 7.38E-01 | 0.57 | 4.94E-01 | 8.76E-01 |
| hsa-miR-1254 | 161 | 160 | 1.01 | 0.01 | 2.76E-01 | 8.64E-01 | 9.48E-02 | 7.43E-01 | 0.57 | 3.54E-01 | 8.76E-01 |
| hsa-miR-1290 | 10 | 17 | 0.58 | -0.55 | 2.96E-01 | 8.64E-01 | 1.00E-01 | 7.43E-01 | 0.44 | 3.00E-01 | 8.76E-01 |
| hsa-miR-586 | 61 | 53 | 1.14 | 0.13 | 1.27E-01 | 8.34E-01 | 1.01E-01 | 7.43E-01 | 0.59 | 1.27E-01 | 8.00E-01 |
| hsa-miR-1293 | 46 | 17 | 2.77 | 1.02 | 1.63E-01 | 8.39E-01 | 1.03E-01 | 7.43E-01 | 0.58 | 2.69E-01 | 8.76E-01 |
| hsa-miR-1248 | 22 | 17 | 1.33 | 0.29 | 1.23E-01 | 8.34E-01 | 1.03E-01 | 7.43E-01 | 0.59 | 1.67E-01 | 8.01E-01 |
| hsa-miR-205 | 62 | 73 | 0.86 | -0.15 | 1.30E-01 | 8.34E-01 | 1.03E-01 | 7.43E-01 | 0.41 | 1.65E-01 | 8.00E-01 |
| hsa-miR-192* | 147 | 157 | 0.93 | -0.07 | 2.78E-02 | 7.91E-01 | 1.03E-01 | 7.43E-01 | 0.37 | 2.03E-02 | 6.45E-01 |
| hsa-miR-920 | 46 | 52 | 0.90 | -0.11 | 2.19E-01 | 8.54E-01 | 1.06E-01 | 7.43E-01 | 0.42 | 1.56E-01 | 8.00E-01 |

FIGURE 1 cont.

| | | | | | | | | | | |
|---|---|---|---|---|---|---|---|---|---|---|
| hsa-miR-1264 | 59 | 48 | 1.22 | 0.20 | 1.17E-01 | 8.34E-01 | 1.06E-01 | 7.43E-01 | 0.60 | 3.68E-01 | 8.76E-01 |
| hsa-miR-181d | 53 | 33 | 1.60 | 0.47 | 1.26E-01 | 8.34E-01 | 1.06E-01 | 7.43E-01 | 0.59 | 6.69E-02 | 7.05E-01 |
| hsa-miR-1274a | 232 | 248 | 0.94 | -0.06 | 3.57E-01 | 8.74E-01 | 1.07E-01 | 7.43E-01 | 0.44 | 3.14E-01 | 8.76E-01 |
| hsa-miR-654-5p | 158 | 161 | 0.99 | -0.01 | 3.19E-01 | 8.65E-01 | 1.07E-01 | 7.43E-01 | 0.56 | 1.87E-01 | 8.48E-01 |
| hsa-miR-1324 | 106 | 94 | 1.12 | 0.12 | 1.04E-01 | 8.34E-01 | 1.07E-01 | 7.43E-01 | 0.60 | 3.37E-01 | 8.76E-01 |
| hsa-miR-142-5p | 961 | 1128 | 0.85 | -0.16 | 9.31E-02 | 8.34E-01 | 1.07E-01 | 7.43E-01 | 0.40 | 1.62E-01 | 8.00E-01 |
| hsa-miR-519c-5p | 165 | 170 | 0.97 | -0.03 | 3.74E-01 | 8.81E-01 | 1.08E-01 | 7.43E-01 | 0.45 | 6.65E-02 | 7.05E-01 |
| hsa-miR-450b-3p | 22 | 11 | 1.89 | 0.64 | 3.44E-01 | 8.65E-01 | 1.08E-01 | 7.43E-01 | 0.56 | 3.38E-01 | 8.76E-01 |
| hsa-miR-421 | 90 | 79 | 1.13 | 0.13 | 7.81E-02 | 8.34E-01 | 1.08E-01 | 7.43E-01 | 0.61 | 4.75E-02 | 7.05E-01 |
| hsa-miR-1252 | 3 | 7 | 0.38 | -0.98 | 3.78E-01 | 8.81E-01 | 1.08E-01 | 7.43E-01 | 0.45 | 2.98E-01 | 8.76E-01 |
| hsa-miR-1914* | 217 | 217 | 1.00 | 0.00 | 3.83E-01 | 8.81E-01 | 1.09E-01 | 7.43E-01 | 0.45 | 2.53E-01 | 8.60E-01 |
| hsa-miR-378 | 338 | 385 | 0.88 | -0.13 | 1.83E-01 | 8.51E-01 | 1.11E-01 | 7.43E-01 | 0.42 | 4.38E-01 | 8.76E-01 |
| hsa-miR-552 | 41 | 52 | 0.78 | -0.25 | 4.04E-01 | 8.87E-01 | 1.11E-01 | 7.43E-01 | 0.45 | 4.88E-01 | 8.76E-01 |
| hsa-miR-155* | 47 | 52 | 0.90 | -0.10 | 3.43E-01 | 8.65E-01 | 1.12E-01 | 7.43E-01 | 0.44 | 3.58E-01 | 8.76E-01 |
| hsa-miR-2276 | 208 | 213 | 0.98 | -0.02 | 3.61E-01 | 8.74E-01 | 1.14E-01 | 7.43E-01 | 0.44 | 7.26E-02 | 7.05E-01 |
| hsa-miR-659 | 55 | 70 | 0.78 | -0.25 | 1.11E-01 | 8.34E-01 | 1.14E-01 | 7.43E-01 | 0.40 | 8.80E-02 | 7.71E-01 |
| hsa-let-7d* | 168 | 215 | 0.78 | -0.24 | 2.10E-01 | 8.54E-01 | 1.15E-01 | 7.43E-01 | 0.42 | 5.98E-02 | 7.05E-01 |
| hsa-miR-525-3p | 65 | 43 | 1.51 | 0.41 | 1.08E-01 | 8.34E-01 | 1.16E-01 | 7.43E-01 | 0.60 | 1.08E-01 | 7.93E-01 |
| hsa-miR-196b* | 177 | 159 | 1.11 | 0.11 | 8.15E-02 | 8.34E-01 | 1.16E-01 | 7.43E-01 | 0.61 | 7.39E-02 | 7.09E-01 |
| hsa-miR-219-1-3p | 26 | 14 | 1.82 | 0.60 | 1.73E-01 | 8.48E-01 | 1.17E-01 | 7.43E-01 | 0.58 | 2.03E-01 | 8.55E-01 |
| hsa-miR-34c-3p | 100 | 110 | 0.91 | -0.10 | 2.28E-01 | 8.54E-01 | 1.17E-01 | 7.43E-01 | 0.43 | 7.30E-01 | 9.31E-01 |
| hsa-miR-579 | 26 | 33 | 0.79 | -0.23 | 2.81E-01 | 8.64E-01 | 1.18E-01 | 7.43E-01 | 0.43 | 7.01E-01 | 9.22E-01 |
| hsa-miR-554 | 82 | 74 | 1.10 | 0.09 | 1.69E-01 | 8.39E-01 | 1.19E-01 | 7.44E-01 | 0.58 | 1.60E-01 | 8.00E-01 |
| hsa-miR-767-3p | 71 | 58 | 1.22 | 0.20 | 1.26E-01 | 8.34E-01 | 1.20E-01 | 7.46E-01 | 0.59 | 3.55E-01 | 8.76E-01 |
| hsa-miR-574-5p | 915 | 569 | 1.61 | 0.48 | 2.06E-02 | 7.00E-01 | 1.21E-01 | 7.46E-01 | 0.64 | 2.68E-02 | 6.97E-01 |
| hsa-miR-99b | 219 | 178 | 1.23 | 0.21 | 1.17E-01 | 8.34E-01 | 1.23E-01 | 7.46E-01 | 0.60 | 5.72E-02 | 7.05E-01 |
| hsa-miR-125a-5p | 299 | 243 | 1.23 | 0.21 | 2.16E-01 | 8.54E-01 | 1.23E-01 | 7.46E-01 | 0.58 | 2.98E-01 | 8.76E-01 |
| hsa-miR-608 | 45 | 26 | 1.71 | 0.54 | 1.60E-01 | 8.39E-01 | 1.24E-01 | 7.46E-01 | 0.59 | 7.70E-02 | 7.31E-01 |
| hsa-miR-1257 | 3 | 1 | 3.30 | 1.20 | 1.39E-01 | 8.34E-01 | 1.24E-01 | 7.46E-01 | 0.58 | 1.22E-01 | 8.00E-01 |
| hsa-miR-934 | 39 | 38 | 1.02 | 0.02 | 1.91E-01 | 8.51E-01 | 1.25E-01 | 7.46E-01 | 0.58 | 4.71E-01 | 8.76E-01 |

FIGURE 1 cont.

| | | | | | | | | | | |
|---|---|---|---|---|---|---|---|---|---|---|
| hsa-miR-548d-3p | 28 | 19 | 1.47 | 0.39 | 2.32E-01 | 8.54E-01 | 1.26E-01 | 7.48E-01 | 0.57 | 3.52E-01 | 8.76E-01 |
| hsa-miR-675 | 187 | 224 | 0.84 | -0.18 | 1.94E-01 | 8.51E-01 | 1.27E-01 | 7.50E-01 | 0.42 | 3.19E-01 | 8.76E-01 |
| hsa-miR-1238 | 46 | 29 | 1.59 | 0.46 | 4.04E-01 | 8.87E-01 | 1.28E-01 | 7.50E-01 | 0.55 | 6.64E-01 | 9.11E-01 |
| hsa-miR-301b | 196 | 187 | 1.05 | 0.05 | 1.49E-01 | 8.34E-01 | 1.29E-01 | 7.52E-01 | 0.59 | 7.15E-02 | 7.05E-01 |
| hsa-miR-449b | 45 | 36 | 1.26 | 0.23 | 1.01E-01 | 8.34E-01 | 1.31E-01 | 7.52E-01 | 0.60 | 3.31E-01 | 8.76E-01 |
| hsa-miR-744* | 40 | 53 | 0.77 | -0.26 | 1.15E-01 | 8.34E-01 | 1.32E-01 | 7.52E-01 | 0.40 | 4.02E-01 | 8.76E-01 |
| hsa-miR-675* | 54 | 66 | 0.81 | -0.21 | 1.13E-02 | 4.79E-01 | 1.32E-01 | 7.52E-01 | 0.34 | 8.90E-01 | 7.71E-02 |
| hsa-miR-24 | 3266 | 3820 | 0.85 | -0.16 | 9.28E-02 | 8.34E-01 | 1.34E-01 | 7.54E-01 | 0.40 | 1.40E-01 | 8.00E-01 |
| hsa-miR-1207-5p | 961 | 1128 | 0.85 | -0.16 | 1.45E-01 | 8.34E-01 | 1.35E-01 | 7.54E-01 | 0.41 | 2.27E-02 | 6.45E-01 |
| hsa-miR-139-3p | 69 | 54 | 1.29 | 0.25 | 1.03E-01 | 8.34E-01 | 1.36E-01 | 7.54E-01 | 0.60 | 1.34E-01 | 8.00E-01 |
| hsa-miR-145 | 223 | 236 | 0.94 | -0.06 | 3.25E-01 | 8.65E-01 | 1.37E-01 | 7.54E-01 | 0.44 | 1.18E-01 | 8.00E-01 |
| hsa-miR-588 | 149 | 130 | 1.14 | 0.13 | 1.05E-01 | 8.34E-01 | 1.37E-01 | 7.54E-01 | 0.60 | 1.22E-01 | 8.00E-01 |
| hsa-miR-151-3p | 926 | 1152 | 0.80 | -0.22 | 1.28E-01 | 8.34E-01 | 1.38E-01 | 7.54E-01 | 0.41 | 1.34E-01 | 8.00E-01 |
| hsa-miR-17* | 805 | 765 | 1.05 | 0.05 | 2.52E-01 | 8.54E-01 | 1.38E-01 | 7.54E-01 | 0.57 | 2.25E-01 | 8.55E-01 |
| hsa-miR-198 | 94 | 75 | 1.25 | 0.22 | 1.30E-01 | 8.34E-01 | 1.40E-01 | 7.56E-01 | 0.59 | 2.63E-01 | 8.73E-01 |
| hsa-let-7a-2* | 82 | 94 | 0.87 | -0.14 | 6.51E-02 | 8.34E-01 | 1.41E-01 | 7.60E-01 | 0.39 | 8.78E-02 | 7.71E-01 |
| hsa-miR-146a | 256 | 340 | 0.75 | -0.28 | 1.86E-01 | 8.51E-01 | 1.42E-01 | 7.60E-01 | 0.42 | 2.36E-01 | 8.55E-01 |
| hsa-miR-650 | 155 | 133 | 1.16 | 0.15 | 1.43E-01 | 8.34E-01 | 1.44E-01 | 7.63E-01 | 0.59 | 1.28E-01 | 8.00E-01 |
| hsa-miR-20b* | 79 | 60 | 1.31 | 0.27 | 6.62E-02 | 8.34E-01 | 1.45E-01 | 7.63E-01 | 0.61 | 4.16E-01 | 8.76E-01 |
| hsa-miR-26a-1* | 25 | 26 | 0.95 | -0.05 | 2.82E-01 | 8.64E-01 | 1.45E-01 | 7.63E-01 | 0.43 | 5.50E-01 | 8.76E-01 |
| hsa-miR-382 | 20 | 14 | 1.42 | 0.35 | 5.05E-01 | 9.21E-01 | 1.47E-01 | 7.66E-01 | 0.54 | 4.53E-01 | 8.76E-01 |
| hsa-miR-24-2* | 135 | 139 | 0.97 | -0.03 | 3.27E-01 | 8.65E-01 | 1.49E-01 | 7.70E-01 | 0.56 | 1.49E-01 | 8.00E-01 |
| hsa-miR-892b | 45 | 39 | 1.14 | 0.13 | 2.63E-01 | 8.59E-01 | 1.50E-01 | 7.70E-01 | 0.57 | 2.96E-01 | 8.76E-01 |
| hsa-miR-595 | 37 | 38 | 1.00 | 0.00 | 3.75E-01 | 8.81E-01 | 1.50E-01 | 7.70E-01 | 0.55 | 1.97E-01 | 8.55E-01 |
| hsa-miR-302f | 7 | 17 | 0.42 | -0.88 | 1.99E-01 | 8.54E-01 | 1.55E-01 | 7.73E-01 | 0.42 | 2.05E-01 | 8.55E-01 |
| hsa-miR-432 | 3 | 21 | 0.13 | -2.03 | 1.34E-01 | 8.34E-01 | 1.57E-01 | 7.73E-01 | 0.41 | 9.41E-02 | 7.72E-01 |
| hsa-miR-181a* | 91 | 73 | 1.26 | 0.23 | 2.02E-01 | 8.54E-01 | 1.58E-01 | 7.73E-01 | 0.58 | 2.29E-01 | 8.55E-01 |
| hsa-miR-1197 | 50 | 43 | 1.17 | 0.15 | 2.23E-01 | 8.54E-01 | 1.59E-01 | 7.73E-01 | 0.57 | 3.00E-01 | 8.76E-01 |
| hsa-miR-2052 | 22 | 24 | 0.91 | -0.09 | 5.12E-01 | 9.21E-01 | 1.61E-01 | 7.73E-01 | 0.46 | 5.17E-01 | 8.76E-01 |
| hsa-miR-1910 | 50 | 47 | 1.06 | 0.06 | 4.02E-01 | 8.87E-01 | 1.61E-01 | 7.73E-01 | 0.55 | 2.24E-01 | 8.55E-01 |

FIGURE 1 cont.

| hsa-miR-2110 | 404 | 388 | 1.04 | 0.04 | 3.78E-01 | 8.81E-01 | 1.62E-01 | 7.73E-01 | 0.45 | 2.48E-01 | 8.56E-01 |
| --- | --- | --- | --- | --- | --- | --- | --- | --- | --- | --- | --- |
| hsa-miR-541 | 97 | 109 | 0.89 | -0.12 | 1.48E-01 | 8.34E-01 | 1.64E-01 | 7.73E-01 | 0.41 | 9.46E-01 | 9.98E-01 |
| hsa-miR-455-5p | 48 | 39 | 1.23 | 0.20 | 1.84E-01 | 8.51E-01 | 1.65E-01 | 7.73E-01 | 0.58 | 2.50E-01 | 8.56E-01 |
| hsa-miR-380* | 78 | 66 | 1.17 | 0.16 | 1.87E-01 | 8.51E-01 | 1.65E-01 | 7.73E-01 | 0.58 | 6.81E-01 | 9.16E-01 |
| hsa-miR-373 | 33 | 31 | 1.06 | 0.06 | 5.47E-01 | 9.28E-01 | 1.65E-01 | 7.73E-01 | 0.46 | 9.98E-01 | 9.98E-01 |
| hsa-miR-612 | 86 | 76 | 1.13 | 0.12 | 3.33E-01 | 8.65E-01 | 1.66E-01 | 7.73E-01 | 0.56 | 8.29E-02 | 7.54E-01 |
| hsa-miR-631 | 175 | 152 | 1.15 | 0.14 | 1.09E-01 | 8.34E-01 | 1.66E-01 | 7.73E-01 | 0.60 | 8.84E-02 | 7.71E-01 |
| hsa-miR-137 | 50 | 52 | 0.97 | -0.03 | 2.34E-01 | 8.54E-01 | 1.67E-01 | 7.73E-01 | 0.43 | 3.08E-01 | 8.76E-01 |
| hsa-miR-1178 | 34 | 28 | 1.18 | 0.17 | 1.52E-01 | 8.39E-01 | 1.68E-01 | 7.73E-01 | 0.59 | 2.97E-02 | 7.03E-01 |
| hsa-miR-518f | 93 | 110 | 0.85 | -0.17 | 2.50E-01 | 8.54E-01 | 1.68E-01 | 7.73E-01 | 0.43 | 4.13E-01 | 8.76E-01 |
| hsa-miR-525-5p | 101 | 109 | 0.93 | -0.08 | 2.76E-01 | 8.64E-01 | 1.69E-01 | 7.73E-01 | 0.43 | 5.87E-01 | 8.82E-01 |
| hsa-miR-2114 | 10 | 17 | 0.61 | -0.50 | 4.33E-01 | 8.94E-01 | 1.69E-01 | 7.73E-01 | 0.45 | 4.51E-01 | 8.76E-01 |
| hsa-miR-532-3p | 4266 | 5613 | 0.76 | -0.27 | 2.37E-01 | 8.54E-01 | 1.70E-01 | 7.73E-01 | 0.43 | 4.05E-01 | 8.76E-01 |
| hsa-miR-663b | 126 | 107 | 1.18 | 0.16 | 2.15E-01 | 8.54E-01 | 1.71E-01 | 7.73E-01 | 0.58 | 3.73E-01 | 8.76E-01 |
| hsa-miR-130a* | 46 | 37 | 1.23 | 0.21 | 1.16E-01 | 8.34E-01 | 1.71E-01 | 7.73E-01 | 0.60 | 3.84E-02 | 7.05E-01 |
| hsa-miR-549 | 58 | 55 | 1.05 | 0.05 | 3.25E-01 | 8.65E-01 | 1.72E-01 | 7.73E-01 | 0.56 | 2.40E-01 | 8.55E-01 |
| hsa-miR-875-5p | 34 | 26 | 1.28 | 0.25 | 4.42E-01 | 8.94E-01 | 1.73E-01 | 7.73E-01 | 0.55 | 5.41E-01 | 8.76E-01 |
| hsa-miR-1537 | 40 | 33 | 1.24 | 0.22 | 2.13E-01 | 8.54E-01 | 1.73E-01 | 7.73E-01 | 0.58 | 3.66E-01 | 8.76E-01 |
| hsa-miR-506 | 48 | 60 | 0.80 | -0.22 | 2.17E-01 | 8.54E-01 | 1.73E-01 | 7.73E-01 | 0.42 | 3.19E-01 | 8.76E-01 |
| hsa-miR-610 | 75 | 69 | 1.09 | 0.08 | 1.91E-01 | 8.51E-01 | 1.74E-01 | 7.73E-01 | 0.58 | 2.66E-01 | 8.76E-01 |
| hsa-miR-876-5p | 28 | 40 | 0.71 | -0.34 | 2.23E-01 | 8.54E-01 | 1.74E-01 | 7.73E-01 | 0.43 | 4.02E-01 | 8.76E-01 |
| hsa-miR-196b | 2 | 3 | 0.70 | -0.35 | 8.94E-01 | 9.84E-01 | 1.77E-01 | 7.77E-01 | 0.51 | 6.71E-01 | 9.13E-01 |

FIGURE 1 cont.

| miRNA | median g1 | median g2 | qmedian | logqmedian | ttest rawp | ttest adjp | limma rawp | limma adjp |
|---|---|---|---|---|---|---|---|---|
| hsa-miR-550a* | 3049 | 2016 | 1.51 | 0.41 | 1.66E-02 | 9.95E-01 | 1.12E-02 | 8.75E-01 |
| hsa-miR-501-3p | 158 | 142 | 1.11 | 0.10 | 2.43E-02 | 9.95E-01 | 2.13E-02 | 8.75E-01 |
| hsa-miR-744 | 166 | 152 | 1.10 | 0.09 | 2.86E-02 | 9.95E-01 | 3.82E-02 | 8.75E-01 |
| hsa-miR-532-3p | 1903 | 1654 | 1.15 | 0.14 | 3.69E-02 | 9.95E-01 | 7.02E-02 | 8.75E-01 |
| hsa-miR-502-3p | 870 | 812 | 1.07 | 0.07 | 3.99E-02 | 9.95E-01 | 7.79E-02 | 8.75E-01 |
| hsa-miR-324-5p | 855 | 741 | 1.15 | 0.14 | 5.59E-02 | 9.95E-01 | 8.02E-02 | 8.75E-01 |
| hsa-miR-140-3p | 21976 | 18890 | 1.16 | 0.15 | 5.91E-02 | 9.95E-01 | 9.20E-02 | 8.75E-01 |
| hsa-miR-652 | 2364 | 2180 | 1.08 | 0.08 | 6.59E-02 | 9.95E-01 | 8.86E-02 | 8.75E-01 |
| hsa-miR-155 | 99 | 138 | 0.72 | -0.33 | 6.67E-02 | 9.95E-01 | 8.05E-02 | 8.75E-01 |
| hsa-miR-342-3p | 2763 | 2461 | 1.12 | 0.12 | 7.71E-02 | 9.95E-01 | 1.05E-01 | 8.75E-01 |
| hsa-miR-664 | 313 | 279 | 1.12 | 0.12 | 1.00E-01 | 9.95E-01 | 1.09E-01 | 8.75E-01 |
| hsa-miR-99b | 65 | 48 | 1.36 | 0.31 | 1.16E-01 | 9.95E-01 | 4.25E-01 | 8.75E-01 |
| hsa-miR-365 | 271 | 238 | 1.14 | 0.13 | 1.33E-01 | 9.95E-01 | 1.38E-01 | 8.75E-01 |
| hsa-miR-3200-3p | 40 | 49 | 0.83 | -0.19 | 1.41E-01 | 9.95E-01 | 2.24E-01 | 8.75E-01 |
| hsa-miR-126 | 2617 | 3174 | 0.82 | -0.19 | 1.42E-01 | 9.95E-01 | 2.61E-02 | 8.75E-01 |
| hsa-miR-500a* | 991 | 884 | 1.12 | 0.11 | 1.47E-01 | 9.95E-01 | 2.23E-01 | 8.75E-01 |
| hsa-miR-221 | 139 | 164 | 0.85 | -0.17 | 1.52E-01 | 9.95E-01 | 1.23E-01 | 8.75E-01 |
| hsa-miR-484 | 4795 | 4468 | 1.07 | 0.07 | 1.57E-01 | 9.95E-01 | 2.48E-01 | 8.75E-01 |
| hsa-miR-146a | 408 | 503 | 0.81 | -0.21 | 1.57E-01 | 9.95E-01 | 7.10E-02 | 8.75E-01 |
| hsa-miR-500b | 82 | 72 | 1.14 | 0.14 | 1.58E-01 | 9.95E-01 | 1.33E-01 | 8.75E-01 |
| hsa-miR-423-3p | 72 | 64 | 1.13 | 0.12 | 1.86E-01 | 9.95E-01 | 1.33E-01 | 8.75E-01 |
| hsa-let-7g | 11392 | 12879 | 0.88 | -0.12 | 1.86E-01 | 9.95E-01 | 9.02E-02 | 8.75E-01 |
| hsa-miR-197 | 841 | 660 | 1.27 | 0.24 | 1.95E-01 | 9.95E-01 | 1.65E-01 | 8.75E-01 |
| hsa-miR-339-5p | 55 | 49 | 1.13 | 0.12 | 2.01E-01 | 9.95E-01 | 2.70E-01 | 8.75E-01 |
| hsa-miR-500a | 263 | 238 | 1.11 | 0.10 | 2.08E-01 | 9.95E-01 | 2.11E-01 | 8.75E-01 |
| hsa-miR-21 | 12087 | 14948 | 0.81 | -0.21 | 2.09E-01 | 9.95E-01 | 1.23E-01 | 8.75E-01 |
| hsa-miR-3653 | 226 | 230 | 0.98 | -0.02 | 2.09E-01 | 9.95E-01 | 2.95E-01 | 8.75E-01 |
| hsa-miR-144* | 6031 | 10671 | 0.57 | -0.57 | 2.10E-01 | 9.95E-01 | 1.92E-02 | 8.75E-01 |
| hsa-miR-3200-5p | 128 | 154 | 0.83 | -0.18 | 2.15E-01 | 9.95E-01 | 1.01E-01 | 8.75E-01 |
| hsa-miR-15a* | 50 | 40 | 1.23 | 0.21 | 2.15E-01 | 9.95E-01 | 5.60E-02 | 8.75E-01 |
| hsa-miR-1260b | 1896 | 1717 | 1.10 | 0.10 | 2.21E-01 | 9.95E-01 | 1.81E-01 | 8.75E-01 |
| hsa-miR-1285 | 126 | 109 | 1.15 | 0.14 | 2.22E-01 | 9.95E-01 | 2.85E-01 | 8.75E-01 |
| hsa-miR-331-3p | 15320 | 13467 | 1.14 | 0.13 | 2.23E-01 | 9.95E-01 | 1.42E-01 | 8.75E-01 |
| hsa-miR-194 | 7326 | 6950 | 1.05 | 0.05 | 2.27E-01 | 9.95E-01 | 2.56E-01 | 8.75E-01 |
| hsa-miR-150 | 10983 | 9247 | 1.19 | 0.17 | 2.38E-01 | 9.95E-01 | 4.49E-01 | 8.75E-01 |
| hsa-miR-3198 | 225 | 216 | 1.04 | 0.04 | 2.51E-01 | 9.95E-01 | 2.62E-01 | 8.75E-01 |
| hsa-miR-324-3p | 5874 | 5358 | 1.10 | 0.09 | 2.57E-01 | 9.95E-01 | 3.38E-01 | 8.75E-01 |
| hsa-miR-222 | 402 | 379 | 1.06 | 0.06 | 2.62E-01 | 9.95E-01 | 3.42E-01 | 8.75E-01 |
| hsa-miR-374c | 218 | 269 | 0.81 | -0.21 | 2.71E-01 | 9.95E-01 | 2.74E-01 | 8.75E-01 |
| hsa-miR-93* | 225 | 211 | 1.07 | 0.07 | 2.83E-01 | 9.95E-01 | 1.58E-01 | 8.75E-01 |

FIGURE 2

| | | | | | | | | |
|---|---|---|---|---|---|---|---|---|
| hsa-miR-424 | 289 | 519 | 0.56 | -0.58 | 2.88E-01 | 9.95E-01 | 6.63E-02 | 8.75E-01 |
| hsa-miR-3125 | 88 | 78 | 1.12 | 0.11 | 2.88E-01 | 9.95E-01 | 4.33E-01 | 8.75E-01 |
| hsa-miR-584 | 454 | 396 | 1.15 | 0.14 | 2.89E-01 | 9.95E-01 | 2.52E-01 | 8.75E-01 |
| hsa-miR-361-3p | 954 | 884 | 1.08 | 0.08 | 2.96E-01 | 9.95E-01 | 3.65E-01 | 8.75E-01 |
| hsa-miR-1274a | 1623 | 1505 | 1.08 | 0.08 | 2.98E-01 | 9.95E-01 | 2.07E-01 | 8.75E-01 |
| hsa-miR-766 | 114 | 113 | 1.01 | 0.01 | 3.00E-01 | 9.95E-01 | 3.98E-01 | 8.75E-01 |
| hsa-miR-423-5p | 2819 | 2617 | 1.08 | 0.07 | 3.04E-01 | 9.95E-01 | 3.11E-01 | 8.75E-01 |
| hsa-miR-23b | 1357 | 1134 | 1.20 | 0.18 | 3.05E-01 | 9.95E-01 | 2.78E-01 | 8.75E-01 |
| hsa-miR-29c* | 1134 | 988 | 1.15 | 0.14 | 3.05E-01 | 9.95E-01 | 2.03E-01 | 8.75E-01 |
| hsa-miR-186 | 4298 | 3706 | 1.16 | 0.15 | 3.08E-01 | 9.95E-01 | 2.05E-01 | 8.75E-01 |
| hsa-miR-4323 | 36 | 38 | 0.95 | -0.05 | 3.11E-01 | 9.95E-01 | 4.82E-01 | 8.75E-01 |
| hsa-let-7b | 9945 | 10983 | 0.91 | -0.10 | 3.13E-01 | 9.95E-01 | 2.17E-01 | 8.75E-01 |
| hsa-miR-769-5p | 47 | 50 | 0.94 | -0.06 | 3.17E-01 | 9.95E-01 | 3.38E-01 | 8.75E-01 |
| hsa-miR-30c | 14616 | 13875 | 1.05 | 0.05 | 3.21E-01 | 9.95E-01 | 4.02E-01 | 8.75E-01 |
| hsa-miR-7 | 786 | 1028 | 0.76 | -0.27 | 3.25E-01 | 9.95E-01 | 7.75E-02 | 8.75E-01 |
| hsa-miR-374b | 1822 | 1833 | 0.99 | -0.01 | 3.25E-01 | 9.95E-01 | 2.00E-01 | 8.75E-01 |
| hsa-miR-451 | 294967 | 294967 | 1.00 | 0.00 | 3.26E-01 | 9.95E-01 | 5.99E-01 | 9.25E-01 |
| hsa-let-7f-1* | 17 | 15 | 1.13 | 0.12 | 3.27E-01 | 9.95E-01 | 3.18E-01 | 8.75E-01 |
| hsa-miR-762 | 54 | 68 | 0.79 | -0.23 | 3.29E-01 | 9.95E-01 | 3.61E-01 | 8.75E-01 |
| hsa-miR-1305 | 176 | 159 | 1.11 | 0.10 | 3.31E-01 | 9.95E-01 | 3.59E-01 | 8.75E-01 |
| hsa-miR-328 | 76 | 71 | 1.07 | 0.06 | 3.32E-01 | 9.95E-01 | 2.36E-01 | 8.75E-01 |
| hsa-miR-378 | 125 | 125 | 1.00 | 0.00 | 3.36E-01 | 9.95E-01 | 2.96E-01 | 8.75E-01 |
| hsa-miR-494 | 211 | 197 | 1.07 | 0.07 | 3.42E-01 | 9.95E-01 | 8.39E-01 | 9.83E-01 |
| hsa-miR-3907 | 204 | 164 | 1.24 | 0.22 | 3.43E-01 | 9.95E-01 | 2.85E-01 | 8.75E-01 |
| hsa-miR-505 | 225 | 204 | 1.11 | 0.10 | 3.45E-01 | 9.95E-01 | 1.54E-01 | 8.75E-01 |
| hsa-miR-199a-5p | 731 | 660 | 1.11 | 0.10 | 3.54E-01 | 9.95E-01 | 3.94E-01 | 8.75E-01 |
| hsa-miR-342-5p | 366 | 325 | 1.13 | 0.12 | 3.56E-01 | 9.95E-01 | 4.29E-01 | 8.75E-01 |
| hsa-miR-1914* | 263 | 238 | 1.10 | 0.10 | 3.72E-01 | 9.95E-01 | 2.80E-01 | 8.75E-01 |
| hsa-miR-1915 | 220 | 236 | 0.93 | -0.07 | 3.82E-01 | 9.95E-01 | 9.43E-01 | 9.83E-01 |
| hsa-miR-4291 | 67 | 86 | 0.78 | -0.25 | 3.82E-01 | 9.95E-01 | 2.55E-01 | 8.75E-01 |
| hsa-miR-361-5p | 576 | 568 | 1.01 | 0.01 | 3.83E-01 | 9.95E-01 | 3.27E-01 | 8.75E-01 |
| hsa-miR-30a | 269 | 248 | 1.08 | 0.08 | 3.88E-01 | 9.95E-01 | 4.85E-01 | 8.75E-01 |
| hsa-let-7d | 8062 | 8444 | 0.95 | -0.05 | 3.97E-01 | 9.95E-01 | 2.59E-01 | 8.75E-01 |
| hsa-miR-24 | 3893 | 4126 | 0.94 | -0.06 | 4.02E-01 | 9.95E-01 | 5.06E-01 | 8.75E-01 |
| hsa-miR-125a-5p | 194 | 172 | 1.13 | 0.12 | 4.06E-01 | 9.95E-01 | 7.84E-01 | 9.83E-01 |
| hsa-miR-340 | 468 | 467 | 1.00 | 0.00 | 4.14E-01 | 9.95E-01 | 4.12E-01 | 8.75E-01 |
| hsa-miR-3940 | 28 | 26 | 1.09 | 0.08 | 4.19E-01 | 9.95E-01 | 4.09E-01 | 8.75E-01 |
| hsa-miR-1288 | 76 | 69 | 1.10 | 0.10 | 4.28E-01 | 9.95E-01 | 4.56E-01 | 8.75E-01 |
| hsa-miR-4318 | 213 | 236 | 0.90 | -0.10 | 4.28E-01 | 9.95E-01 | 4.67E-01 | 8.75E-01 |
| hsa-miR-30d | 7867 | 6767 | 1.16 | 0.15 | 4.29E-01 | 9.95E-01 | 5.17E-01 | 8.75E-01 |
| hsa-let-7c | 2719 | 2819 | 0.96 | -0.04 | 4.37E-01 | 9.95E-01 | 3.32E-01 | 8.75E-01 |
| hsa-miR-4317 | 40 | 52 | 0.76 | -0.27 | 4.42E-01 | 9.95E-01 | 1.51E-01 | 8.75E-01 |
| hsa-miR-215 | 5358 | 4136 | 1.30 | 0.26 | 4.47E-01 | 9.95E-01 | 6.32E-01 | 9.61E-01 |

FIGURE 2 cont.

| | | | | | | | | |
|---|---|---|---|---|---|---|---|---|
| hsa-miR-29b | 3278 | 3174 | 1.03 | 0.03 | 4.48E-01 | 9.95E-01 | 7.02E-01 | 9.83E-01 |
| hsa-let-7b* | 15 | 19 | 0.80 | -0.23 | 4.54E-01 | 9.95E-01 | 8.22E-01 | 9.83E-01 |
| hsa-miR-101 | 4795 | 5136 | 0.93 | -0.07 | 4.56E-01 | 9.95E-01 | 2.69E-01 | 8.75E-01 |
| hsa-miR-142-3p | 46848 | 37224 | 1.26 | 0.23 | 4.57E-01 | 9.95E-01 | 4.09E-01 | 8.75E-01 |
| hsa-miR-1280 | 461 | 402 | 1.15 | 0.14 | 4.60E-01 | 9.95E-01 | 3.24E-01 | 8.75E-01 |
| hsa-miR-25 | 75010 | 75010 | 1.00 | 0.00 | 4.63E-01 | 9.95E-01 | 5.26E-01 | 8.83E-01 |
| hsa-miR-378* | 172 | 132 | 1.30 | 0.27 | 4.64E-01 | 9.95E-01 | 2.62E-01 | 8.75E-01 |
| hsa-miR-142-5p | 12113 | 10671 | 1.14 | 0.13 | 4.65E-01 | 9.95E-01 | 4.46E-01 | 8.75E-01 |
| hsa-miR-363 | 12879 | 12113 | 1.06 | 0.06 | 4.66E-01 | 9.95E-01 | 4.91E-01 | 8.75E-01 |
| hsa-miR-625 | 441 | 454 | 0.97 | -0.03 | 4.82E-01 | 9.95E-01 | 9.69E-01 | 9.83E-01 |
| hsa-miR-720 | 44457 | 40259 | 1.10 | 0.10 | 4.82E-01 | 9.95E-01 | 4.13E-01 | 8.75E-01 |
| hsa-miR-574-3p | 474 | 423 | 1.12 | 0.11 | 4.84E-01 | 9.95E-01 | 5.15E-01 | 8.75E-01 |
| hsa-miR-128 | 1630 | 1416 | 1.15 | 0.14 | 4.89E-01 | 9.95E-01 | 1.99E-01 | 8.75E-01 |
| hsa-miR-193a-3p | 77 | 88 | 0.88 | -0.13 | 4.89E-01 | 9.95E-01 | 7.79E-01 | 9.83E-01 |
| hsa-miR-939 | 166 | 189 | 0.88 | -0.13 | 4.89E-01 | 9.95E-01 | 9.73E-01 | 9.83E-01 |
| hsa-miR-20a | 3422 | 4039 | 0.85 | -0.17 | 5.01E-01 | 9.95E-01 | 2.71E-01 | 8.75E-01 |
| hsa-miR-192 | 9017 | 7867 | 1.15 | 0.14 | 5.03E-01 | 9.95E-01 | 6.28E-01 | 9.61E-01 |
| hsa-miR-130a | 2514 | 2461 | 1.02 | 0.02 | 5.12E-01 | 9.95E-01 | 5.96E-01 | 9.25E-01 |
| hsa-let-7a | 26925 | 27680 | 0.97 | -0.03 | 5.13E-01 | 9.95E-01 | 2.47E-01 | 8.75E-01 |
| hsa-miR-27a | 1069 | 1307 | 0.82 | -0.20 | 5.24E-01 | 9.95E-01 | 1.56E-01 | 8.75E-01 |
| hsa-miR-339-3p | 26 | 26 | 1.00 | 0.00 | 5.24E-01 | 9.95E-01 | 5.68E-01 | 9.16E-01 |
| hsa-miR-942 | 150 | 109 | 1.37 | 0.32 | 5.26E-01 | 9.95E-01 | 2.29E-01 | 8.75E-01 |
| hsa-miR-22 | 40259 | 44457 | 0.91 | -0.10 | 5.38E-01 | 9.95E-01 | 4.96E-01 | 8.75E-01 |
| hsa-miR-3180-3p | 63 | 52 | 1.21 | 0.19 | 5.38E-01 | 9.95E-01 | 4.61E-01 | 8.75E-01 |
| hsa-miR-1225-5p | 329 | 362 | 0.91 | -0.10 | 5.40E-01 | 9.95E-01 | 7.72E-01 | 9.83E-01 |
| hsa-miR-627 | 329 | 356 | 0.92 | -0.08 | 5.52E-01 | 9.95E-01 | 4.50E-01 | 8.75E-01 |
| hsa-miR-505* | 282 | 289 | 0.97 | -0.03 | 5.52E-01 | 9.95E-01 | 6.37E-01 | 9.62E-01 |
| hsa-miR-15b* | 329 | 302 | 1.09 | 0.08 | 5.55E-01 | 9.95E-01 | 9.29E-01 | 9.83E-01 |
| hsa-miR-16 | 100974 | 114310 | 0.88 | -0.12 | 5.56E-01 | 9.95E-01 | 1.72E-01 | 8.75E-01 |
| hsa-miR-501-5p | 111 | 111 | 1.00 | 0.00 | 5.60E-01 | 9.95E-01 | 5.38E-01 | 8.95E-01 |
| hsa-miR-106b | 31938 | 35483 | 0.90 | -0.11 | 5.64E-01 | 9.95E-01 | 5.09E-01 | 8.75E-01 |
| hsa-miR-362-3p | 954 | 860 | 1.11 | 0.10 | 5.65E-01 | 9.95E-01 | 5.62E-01 | 9.16E-01 |
| hsa-miR-26a | 17403 | 16077 | 1.08 | 0.08 | 5.71E-01 | 9.95E-01 | 4.28E-01 | 8.75E-01 |
| hsa-miR-132 | 107 | 117 | 0.91 | -0.09 | 5.73E-01 | 9.95E-01 | 5.47E-01 | 9.03E-01 |
| hsa-miR-1268 | 58 | 61 | 0.94 | -0.06 | 5.76E-01 | 9.95E-01 | 9.58E-01 | 9.83E-01 |
| hsa-miR-181b | 55 | 51 | 1.08 | 0.08 | 5.78E-01 | 9.95E-01 | 5.06E-01 | 8.75E-01 |
| hsa-miR-28-5p | 228 | 249 | 0.92 | -0.09 | 5.92E-01 | 9.95E-01 | 3.00E-01 | 8.75E-01 |
| hsa-miR-212 | 32 | 35 | 0.91 | -0.09 | 5.92E-01 | 9.95E-01 | 7.08E-01 | 9.83E-01 |
| hsa-miR-151-3p | 1224 | 1284 | 0.95 | -0.05 | 5.95E-01 | 9.95E-01 | 8.86E-01 | 9.83E-01 |
| hsa-miR-17 | 3800 | 4557 | 0.83 | -0.18 | 5.99E-01 | 9.95E-01 | 3.43E-01 | 8.75E-01 |
| hsa-miR-362-5p | 919 | 1028 | 0.89 | -0.11 | 5.99E-01 | 9.95E-01 | 4.35E-01 | 8.75E-01 |
| hsa-miR-144 | 35483 | 35483 | 1.00 | 0.00 | 6.00E-01 | 9.95E-01 | 6.91E-01 | 9.83E-01 |
| hsa-let-7i | 7326 | 9475 | 0.77 | -0.26 | 6.07E-01 | 9.95E-01 | 1.59E-01 | 8.75E-01 |

FIGURE 2 cont.

| | | | | | | | | |
|---|---|---|---|---|---|---|---|---|
| hsa-miR-4281 | 1054 | 975 | 1.08 | 0.08 | 6.07E-01 | 9.95E-01 | 9.74E-01 | 9.83E-01 |
| hsa-miR-1274b | 21334 | 18358 | 1.16 | 0.15 | 6.10E-01 | 9.95E-01 | 3.87E-01 | 8.75E-01 |
| hsa-miR-92a | 114310 | 114310 | 1.00 | 0.00 | 6.12E-01 | 9.95E-01 | 6.62E-01 | 9.79E-01 |
| hsa-miR-502-5p | 160 | 132 | 1.21 | 0.19 | 6.18E-01 | 9.95E-01 | 6.84E-01 | 9.83E-01 |
| hsa-miR-181a | 658 | 660 | 1.00 | 0.00 | 6.26E-01 | 9.95E-01 | 7.01E-01 | 9.83E-01 |
| hsa-miR-3651 | 144 | 164 | 0.88 | -0.13 | 6.34E-01 | 9.95E-01 | 9.33E-01 | 9.83E-01 |
| hsa-miR-3162 | 269 | 333 | 0.81 | -0.21 | 6.35E-01 | 9.95E-01 | 7.95E-01 | 9.83E-01 |
| hsa-miR-19a | 21976 | 23114 | 0.95 | -0.05 | 6.35E-01 | 9.95E-01 | 5.02E-01 | 8.75E-01 |
| hsa-miR-17* | 346 | 375 | 0.92 | -0.08 | 6.43E-01 | 9.95E-01 | 7.55E-01 | 9.83E-01 |
| hsa-miR-93 | 2617 | 2987 | 0.88 | -0.13 | 6.56E-01 | 9.95E-01 | 5.16E-01 | 8.75E-01 |
| hsa-miR-3195 | 166 | 184 | 0.90 | -0.10 | 6.58E-01 | 9.95E-01 | 8.71E-01 | 9.83E-01 |
| hsa-miR-4270 | 154 | 146 | 1.05 | 0.05 | 6.59E-01 | 9.95E-01 | 7.63E-01 | 9.83E-01 |
| hsa-miR-4286 | 4296 | 3893 | 1.10 | 0.10 | 6.62E-01 | 9.95E-01 | 4.80E-01 | 8.75E-01 |
| hsa-miR-130b | 1307 | 1416 | 0.92 | -0.08 | 6.66E-01 | 9.95E-01 | 5.16E-01 | 8.75E-01 |
| hsa-let-7f | 16933 | 16463 | 1.03 | 0.03 | 6.69E-01 | 9.95E-01 | 3.85E-01 | 8.75E-01 |
| hsa-miR-4306 | 54790 | 54790 | 1.00 | 0.00 | 6.73E-01 | 9.95E-01 | 5.66E-01 | 9.16E-01 |
| hsa-miR-182 | 799 | 826 | 0.97 | -0.03 | 6.82E-01 | 9.95E-01 | 8.24E-01 | 9.83E-01 |
| hsa-miR-638 | 174 | 176 | 0.99 | -0.01 | 6.84E-01 | 9.95E-01 | 8.16E-01 | 9.83E-01 |
| hsa-miR-30e | 6584 | 6018 | 1.09 | 0.09 | 6.87E-01 | 9.95E-01 | 9.29E-01 | 9.83E-01 |
| hsa-miR-27b | 225 | 208 | 1.08 | 0.08 | 6.92E-01 | 9.95E-01 | 2.71E-01 | 8.75E-01 |
| hsa-miR-320e | 5874 | 5033 | 1.17 | 0.15 | 6.93E-01 | 9.95E-01 | 9.31E-01 | 9.83E-01 |
| hsa-miR-20b | 2180 | 2226 | 0.98 | -0.02 | 6.95E-01 | 9.95E-01 | 2.07E-01 | 8.75E-01 |
| hsa-miR-103 | 14948 | 16077 | 0.93 | -0.07 | 6.97E-01 | 9.95E-01 | 4.42E-01 | 8.75E-01 |
| hsa-miR-148a | 2512 | 2933 | 0.86 | -0.15 | 7.09E-01 | 9.95E-01 | 1.65E-01 | 8.75E-01 |
| hsa-miR-148b | 1008 | 938 | 1.08 | 0.07 | 7.09E-01 | 9.95E-01 | 6.90E-01 | 9.83E-01 |
| hsa-let-7d* | 76 | 72 | 1.05 | 0.05 | 7.16E-01 | 9.95E-01 | 7.12E-01 | 9.83E-01 |
| hsa-miR-3196 | 146 | 154 | 0.95 | -0.05 | 7.27E-01 | 9.95E-01 | 8.54E-01 | 9.83E-01 |
| hsa-miR-145 | 266 | 228 | 1.17 | 0.16 | 7.38E-01 | 9.95E-01 | 9.84E-01 | 9.84E-01 |
| hsa-miR-320c | 4897 | 3893 | 1.26 | 0.23 | 7.54E-01 | 9.95E-01 | 8.42E-01 | 9.83E-01 |
| hsa-miR-1260 | 9718 | 7867 | 1.24 | 0.21 | 7.57E-01 | 9.95E-01 | 3.00E-01 | 8.75E-01 |
| hsa-miR-320b | 5874 | 5604 | 1.05 | 0.05 | 7.66E-01 | 9.95E-01 | 8.80E-01 | 9.83E-01 |
| hsa-miR-454 | 391 | 385 | 1.01 | 0.01 | 7.70E-01 | 9.95E-01 | 5.83E-01 | 9.25E-01 |
| hsa-miR-3679-5p | 71 | 65 | 1.09 | 0.09 | 7.80E-01 | 9.95E-01 | 5.77E-01 | 9.24E-01 |
| hsa-miR-140-5p | 396 | 402 | 0.99 | -0.01 | 7.84E-01 | 9.95E-01 | 3.35E-01 | 8.75E-01 |
| hsa-miR-29a | 3422 | 3160 | 1.08 | 0.08 | 7.86E-01 | 9.95E-01 | 7.37E-01 | 9.83E-01 |
| hsa-miR-183 | 1284 | 1384 | 0.93 | -0.07 | 8.00E-01 | 9.95E-01 | 7.34E-01 | 9.83E-01 |
| hsa-miR-98 | 229 | 241 | 0.95 | -0.05 | 8.11E-01 | 9.95E-01 | 2.28E-01 | 8.75E-01 |
| hsa-miR-296-5p | 63 | 60 | 1.04 | 0.04 | 8.14E-01 | 9.95E-01 | 9.59E-01 | 9.83E-01 |
| hsa-miR-532-5p | 660 | 648 | 1.02 | 0.02 | 8.15E-01 | 9.95E-01 | 9.64E-01 | 9.83E-01 |
| hsa-miR-2861 | 370 | 314 | 1.18 | 0.17 | 8.16E-01 | 9.95E-01 | 7.57E-01 | 9.83E-01 |
| hsa-miR-195 | 371 | 481 | 0.77 | -0.26 | 8.21E-01 | 9.95E-01 | 3.49E-01 | 8.75E-01 |
| hsa-miR-191 | 56 | 60 | 0.93 | -0.08 | 8.23E-01 | 9.95E-01 | 8.67E-01 | 9.83E-01 |
| hsa-miR-892b | 42 | 38 | 1.12 | 0.11 | 8.27E-01 | 9.95E-01 | 7.10E-01 | 9.83E-01 |
| hsa-miR-590-5p | 424 | 428 | 0.99 | -0.01 | 8.34E-01 | 9.95E-01 | 2.11E-01 | 8.75E-01 |

FIGURE 2 cont.

| | | | | | | | | |
|---|---|---|---|---|---|---|---|---|
| hsa-miR-326 | 96 | 97 | 0.99 | -0.01 | 8.38E-01 | 9.95E-01 | 8.19E-01 | 9.83E-01 |
| hsa-miR-1202 | 288 | 303 | 0.95 | -0.05 | 8.41E-01 | 9.95E-01 | 7.27E-01 | 9.83E-01 |
| hsa-miR-425 | 27680 | 29910 | 0.93 | -0.08 | 8.43E-01 | 9.95E-01 | 9.27E-01 | 9.83E-01 |
| hsa-miR-486-5p | 186211 | 186211 | 1.00 | 0.00 | 8.51E-01 | 9.95E-01 | 7.30E-01 | 9.83E-01 |
| hsa-miR-223 | 114310 | 100974 | 1.13 | 0.12 | 8.55E-01 | 9.95E-01 | 5.08E-01 | 8.75E-01 |
| hsa-miR-320d | 7503 | 6452 | 1.16 | 0.15 | 8.59E-01 | 9.95E-01 | 8.97E-01 | 9.83E-01 |
| hsa-miR-30b | 40259 | 40259 | 1.00 | 0.00 | 8.63E-01 | 9.95E-01 | 9.79E-01 | 9.83E-01 |
| hsa-miR-16-2* | 1008 | 1245 | 0.81 | -0.21 | 8.67E-01 | 9.95E-01 | 5.96E-01 | 9.25E-01 |
| hsa-miR-575 | 125 | 117 | 1.07 | 0.06 | 8.68E-01 | 9.95E-01 | 7.03E-01 | 9.83E-01 |
| hsa-miR-30e* | 372 | 370 | 1.00 | 0.00 | 8.72E-01 | 9.95E-01 | 9.48E-01 | 9.83E-01 |
| hsa-miR-18a | 352 | 322 | 1.09 | 0.09 | 8.78E-01 | 9.95E-01 | 4.88E-01 | 8.75E-01 |
| hsa-miR-624* | 108 | 148 | 0.73 | -0.31 | 8.84E-01 | 9.95E-01 | 9.69E-01 | 9.83E-01 |
| hsa-miR-301a | 425 | 454 | 0.94 | -0.07 | 8.84E-01 | 9.95E-01 | 2.51E-01 | 8.75E-01 |
| hsa-miR-185 | 35483 | 34188 | 1.04 | 0.04 | 8.85E-01 | 9.95E-01 | 8.83E-01 | 9.83E-01 |
| hsa-miR-1275 | 85 | 73 | 1.16 | 0.15 | 8.87E-01 | 9.95E-01 | 9.47E-01 | 9.83E-01 |
| hsa-miR-107 | 23114 | 22545 | 1.03 | 0.02 | 8.87E-01 | 9.95E-01 | 6.42E-01 | 9.62E-01 |
| hsa-miR-629* | 32 | 33 | 0.96 | -0.04 | 8.94E-01 | 9.95E-01 | 8.59E-01 | 9.83E-01 |
| hsa-miR-19b | 114310 | 114310 | 1.00 | 0.00 | 8.98E-01 | 9.95E-01 | 8.46E-01 | 9.83E-01 |
| hsa-miR-3665 | 648 | 576 | 1.13 | 0.12 | 8.99E-01 | 9.95E-01 | 7.04E-01 | 9.83E-01 |
| hsa-miR-660 | 1480 | 1480 | 1.00 | 0.00 | 9.04E-01 | 9.95E-01 | 8.75E-01 | 9.83E-01 |
| hsa-miR-23a | 10742 | 11296 | 0.95 | -0.05 | 9.05E-01 | 9.95E-01 | 8.83E-01 | 9.83E-01 |
| hsa-miR-29c | 12496 | 10671 | 1.17 | 0.16 | 9.06E-01 | 9.95E-01 | 9.03E-01 | 9.83E-01 |
| hsa-miR-151-5p | 7138 | 7326 | 0.97 | -0.03 | 9.16E-01 | 9.95E-01 | 9.74E-01 | 9.83E-01 |
| hsa-miR-26b | 5748 | 6402 | 0.90 | -0.11 | 9.16E-01 | 9.95E-01 | 4.93E-01 | 8.75E-01 |
| hsa-miR-320a | 2987 | 2821 | 1.06 | 0.06 | 9.22E-01 | 9.95E-01 | 7.74E-01 | 9.83E-01 |
| hsa-miR-103-2* | 37 | 36 | 1.03 | 0.03 | 9.25E-01 | 9.95E-01 | 9.32E-01 | 9.83E-01 |
| hsa-miR-940 | 81 | 76 | 1.07 | 0.07 | 9.27E-01 | 9.95E-01 | 8.25E-01 | 9.83E-01 |
| hsa-miR-629 | 314 | 266 | 1.18 | 0.16 | 9.40E-01 | 9.95E-01 | 9.30E-01 | 9.83E-01 |
| hsa-miR-18b | 442 | 419 | 1.06 | 0.05 | 9.43E-01 | 9.95E-01 | 4.84E-01 | 8.75E-01 |
| hsa-miR-183* | 36 | 35 | 1.03 | 0.03 | 9.49E-01 | 9.95E-01 | 8.95E-01 | 9.83E-01 |
| hsa-miR-1207-5p | 238 | 244 | 0.97 | -0.03 | 9.51E-01 | 9.95E-01 | 8.66E-01 | 9.83E-01 |
| hsa-miR-4284 | 988 | 870 | 1.14 | 0.13 | 9.51E-01 | 9.95E-01 | 8.92E-01 | 9.83E-01 |
| hsa-miR-99a | 89 | 94 | 0.94 | -0.06 | 9.56E-01 | 9.95E-01 | 9.67E-01 | 9.83E-01 |
| hsa-miR-15a | 26170 | 27680 | 0.95 | -0.06 | 9.61E-01 | 9.95E-01 | 4.06E-01 | 8.75E-01 |
| hsa-miR-374a | 2133 | 2763 | 0.77 | -0.26 | 9.65E-01 | 9.95E-01 | 8.29E-01 | 9.83E-01 |
| hsa-miR-210 | 1833 | 1686 | 1.09 | 0.08 | 9.70E-01 | 9.95E-01 | 9.41E-01 | 9.83E-01 |
| hsa-miR-96 | 1536 | 1623 | 0.95 | -0.06 | 9.77E-01 | 9.95E-01 | 6.60E-01 | 9.79E-01 |
| hsa-miR-338-3p | 162 | 206 | 0.79 | -0.24 | 9.80E-01 | 9.95E-01 | 3.15E-01 | 8.75E-01 |
| hsa-miR-3656 | 528 | 414 | 1.28 | 0.24 | 9.83E-01 | 9.95E-01 | 5.87E-01 | 9.25E-01 |
| hsa-miR-15b | 114310 | 107642 | 1.06 | 0.06 | 9.84E-01 | 9.95E-01 | 8.98E-01 | 9.83E-01 |
| hsa-miR-125b | 401 | 454 | 0.88 | -0.12 | 9.86E-01 | 9.95E-01 | 9.01E-01 | 9.83E-01 |
| hsa-miR-4299 | 154 | 121 | 1.27 | 0.24 | 9.94E-01 | 9.99E-01 | 4.84E-01 | 8.75E-01 |
| hsa-miR-146b-5p | 122 | 135 | 0.90 | -0.10 | 1.00E+00 | 1.00E+00 | 4.99E-01 | 8.75E-01 |

FIGURE 2 cont.

| Signature | # miRNAs | Accuracy | miRNAs |
|---|---|---|---|
| DCM-1 | 2 | 74.0% | hsa-miR-718, hsa-miR-634 |
| DCM-2 | 2 | 72.7% | hsa-miR-519e*, hsa-miR-1236 |
| DCM-3 | 3 | 72.3% | hsa-miR-718, hsa-miR-30e, hsa-miR-634, |
| DCM-4 | 3 | 72.2% | hsa-miR-32*, hsa-miR-519e*, hsa-miR-1236, |
| DCM-5 | 4 | 70.2% | hsa-miR-32*, hsa-miR-519e*, hsa-miR-1236, hsa-let-7i* |
| DCM-6 | 4 | 71.9% | hsa-miR-32*, hsa-miR-519e*, hsa-miR-1236, hsa-let-7i* |
| DCM-7 | 5 | 70.7% | hsa-miR-26a, hsa-miR-1268, hsa-miR-150, hsa-miR-144, hsa-miR-574-5p |
| DCM-8 | 5 | 71.0% | hsa-miR-32*, hsa-miR-2114*, hsa-miR-519e*, hsa-miR-1236, hsa-let-7i* |
| DCM-9 | 6 | 68.9% | hsa-miR-718, hsa-miR-153, hsa-miR-148a, hsa-miR-92a, hsa-miR-574-5p, hsa-miR-422a |
| DCM-10 | 6 | 69.9% | hsa-miR-890, hsa-miR-566, hsa-miR-32*, hsa-miR-493*, hsa-miR-718, hsa-miR-760 |
| DCM-11 | 7 | 72.6% | hsa-miR-1268, hsa-miR-718, hsa-miR-153, hsa-miR-148a, hsa-miR-92a, hsa-miR-574-5p, hsa-miR-422a |
| DCM-12 | 7 | 73.0% | hsa-miR-513a-3p, hsa-miR-566, hsa-miR-32*, hsa-miR-935, hsa-miR-30c-2*, hsa-miR-760, hsa-miR-877* |
| DCM-13 | 8 | 73.8% | hsa-miR-563, hsa-miR-935, hsa-miR-493*, hsa-miR-1912, hsa-miR-202*, hsa-miR-558, hsa-miR-520d-5p, hsa-miR-877* |
| DCM-14 | 8 | 73.8% | hsa-miR-513a-3p, hsa-miR-32*, hsa-miR-2114*, hsa-miR-935, hsa-miR-519e*, hsa-miR-1236, hsa-miR-520d-5p, hsa-let-7i* |
| DCM-15 | 9 | 74.4% | hsa-miR-1268, hsa-miR-718, hsa-miR-153, hsa-miR-516a-5p, hsa-miR-148a, hsa-miR-92a, hsa-miR-574-5p, hsa-miR-191, hsa-miR-422a |
| DCM-16 | 9 | 76.6% | hsa-miR-513a-3p, hsa-miR-32*, hsa-miR-2114*, hsa-miR-935, hsa-miR-519e*, hsa-miR-1236, hsa-miR-520d-5p, hsa-miR-877*, hsa-let-7i* |
| DCM-17 | 10 | 73.6% | hsa-miR-513a-3p, hsa-miR-566, hsa-miR-32*, hsa-miR-935, hsa-miR-30c-2*, hsa-miR-493*, hsa-miR-1304, hsa-miR-520d-5p, hsa-miR-760, hsa-miR-877* |
| DCM-18 | 10 | 75.7% | hsa-miR-513a-3p, hsa-miR-32*, hsa-miR-2114*, hsa-miR-935, hsa-miR-202*, hsa-miR-519e*, hsa-miR-1236, hsa-miR-520d-5p, hsa-miR-877*, hsa-let-7i* |
| DCM-19 | 11 | 74.1% | hsa-miR-513a-3p, hsa-miR-566, hsa-miR-32*, hsa-miR-935, hsa-miR-30c-2*, hsa-miR-493*, hsa-miR-1304, hsa-miR-564, hsa-miR-520d-5p, hsa-miR-760, hsa-miR-877* |
| DCM-20 | 11 | 75.2% | hsa-miR-513a-3p, hsa-miR-32*, hsa-miR-2114*, hsa-miR-935, hsa-miR-202*, hsa-miR-519e*, hsa-miR-1236, hsa-miR-520d-5p, hsa-miR-760, hsa-miR-877*, hsa-let-7i* |
| DCM-21 | 12 | 73.7% | hsa-miR-513a-3p, hsa-miR-563, hsa-miR-566, hsa-miR-32*, hsa-miR-935, hsa-miR-30c-2*, hsa-miR-493*, hsa-miR-1304, hsa-miR-564, hsa-miR-520d-5p, hsa-miR-760, hsa-miR-877* |
| DCM-22 | 12 | 75.0% | hsa-miR-513a-3p, hsa-miR-563, hsa-miR-566, hsa-miR-32*, hsa-miR-935, hsa-miR-30c-2*, hsa-miR-493*, hsa-miR-1304, hsa-miR-564, hsa-miR-520d-5p, hsa-miR-760, hsa-miR-877* |
| DCM-23 | 13 | 73.7% | hsa-miR-513a-3p, hsa-miR-563, hsa-miR-32*, hsa-miR-935, hsa-miR-30c-2*, hsa-miR-493*, hsa-miR-1304, hsa-miR-1912, hsa-miR-202*, hsa-miR-558, hsa-miR-520d-5p, hsa-miR-760, hsa-miR-877* |
| DCM-24 | 13 | 74.6% | hsa-miR-513a-3p, hsa-miR-563, hsa-miR-32*, hsa-miR-935, hsa-miR-30c-2*, hsa-miR-493*, hsa-miR-1304, hsa-miR-1912, hsa-miR-202*, hsa-miR-558, hsa-miR-520d-5p, hsa-miR-760, hsa-miR-877* |
| DCM-25 | 14 | 73.5% | hsa-miR-513a-3p, hsa-miR-890, hsa-miR-566, hsa-miR-32*, hsa-miR-935, hsa-miR-30c-2*, hsa-miR-493*, hsa-miR-1304, hsa-miR-202*, hsa-miR-558, hsa-miR-520d-5p, hsa-miR-760, hsa-let-7e*, hsa-miR-877* |

FIGURE 3A

| | | | |
|---|---|---|---|
| DCM-26 | 14 | 73.1% | hsa-miR-513a-3p, hsa-miR-563, hsa-miR-566, hsa-miR-32*, hsa-miR-935, hsa-miR-30c-2*, hsa-miR-493*, hsa-miR-1304, hsa-miR-564, hsa-miR-202*, hsa-miR-520d-5p, hsa-miR-760, hsa-let-7e*, hsa-miR-877* |
| DCM-27 | 15 | 73.3% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-520d-5p, hsa-miR-760, hsa-miR-524-3p, hsa-let-7e*, hsa-miR-877* |
| DCM-28 | 15 | 75.2% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-520d-5p, hsa-miR-760, hsa-miR-524-3p, hsa-let-7e*, hsa-miR-877* |
| DCM-29 | 16 | 72.8% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-520d-5p, hsa-miR-760, hsa-miR-524-3p, hsa-let-7e*, hsa-miR-877* |
| DCM-30 | 16 | 74.5% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-520d-5p, hsa-miR-760, hsa-miR-524-3p, hsa-let-7e*, hsa-miR-877* |
| DCM-31 | 17 | 73.1% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-558, hsa-miR-520d-5p, hsa-miR-760, hsa-miR-524-3p, hsa-let-7e*, hsa-miR-877* |
| DCM-32 | 17 | 73.2% | hsa-miR-513a-3p, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-558, hsa-miR-520d-5p, hsa-miR-760, hsa-miR-524-3p, hsa-let-7e*, hsa-miR-877* |
| DCM-33 | 18 | 73.7% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-520d-5p, hsa-miR-760, hsa-miR-524-3p, hsa-let-7e*, hsa-miR-877*, hsa-miR-302d |
| DCM-34 | 18 | 74.3% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-558, hsa-miR-520d-5p, hsa-miR-760, hsa-miR-524-3p, hsa-let-7e*, hsa-miR-877* |
| DCM-35 | 19 | 73.3% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-558, hsa-miR-520d-5p, hsa-miR-760, hsa-miR-524-3p, hsa-let-7e*, hsa-miR-877*, hsa-miR-302d |
| DCM-36 | 19 | 74.0% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-564, hsa-miR-202*, hsa-miR-892a, hsa-miR-558, hsa-miR-520d-5p, hsa-miR-760, hsa-miR-524-3p, hsa-let-7e*, hsa-miR-877* |
| DCM-37 | 20 | 72.7% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-513a-5p, hsa-miR-564, hsa-miR-202*, hsa-miR-892a, hsa-miR-558, hsa-miR-520d-5p, hsa-miR-760, hsa-miR-524-3p, hsa-let-7e*, hsa-miR-877* |
| DCM-38 | 20 | 74.1% | hsa-miR-513a-3p, hsa-miR-890, hsa-miR-563, hsa-miR-566, hsa-miR-32*, hsa-miR-935, hsa-miR-30c-2*, hsa-miR-1302, hsa-miR-493*, hsa-miR-1304, hsa-miR-513a-5p, hsa-miR-202*, hsa-miR-708*, hsa-miR-892a, hsa-miR-558, hsa-miR-520d-5p, hsa-miR-760, hsa-miR-524-3p, hsa-let-7e*, hsa-miR-877* |

FIGURE 3A cont.

| Signature | # miRNAs | Accuracy | miRNAs |
|---|---|---|---|
| DCM-39 | 8 | 70 % | hsa-miR-558, hsa-miR-122*, hsa-miR -520d-5p, hsa-miR -622, hsa-miR-519e*, hsa-miR -1228*, hsa-miR -200b*, hsa-miR -1231 |
| DCM-40 | 2 | | hsa-miR-122*, hsa-miR-1228* |
| DCM-41 | 2 | | hsa-miR-122*, hsa-miR-558 |
| DCM-42 | 2 | | hsa-miR-122*, hsa-miR-519e* |
| DCM-43 | 2 | | hsa-miR-122*, hsa-miR-622 |
| DCM-44 | 2 | | hsa-miR-122*, hsa-miR-520d-5p |
| DCM-45 | 2 | | hsa-miR-122*, hsa-miR-200b* |
| DCM-46 | 2 | | hsa-miR-1228*, hsa-miR-558 |
| DCM-47 | 2 | | hsa-miR-1228*, hsa-miR-519e* |
| DCM-48 | 2 | | hsa-miR-1228*, hsa-miR-622 |
| DCM-49 | 2 | | hsa-miR-1228*, hsa-miR-520d-5p |
| DCM-50 | 2 | | hsa-miR-1228*, hsa-miR-200b* |
| DCM-51 | 2 | | hsa-miR-558, hsa-miR-519e* |
| DCM-52 | 2 | | hsa-miR-558, hsa-miR-622 |
| DCM-53 | 2 | | hsa-miR-558, hsa-miR-520d-5p |
| DCM-54 | 2 | | hsa-miR-558, hsa-miR-200b* |
| DCM-55 | 2 | | hsa-miR-519e*, hsa-miR-622 |
| DCM-56 | 2 | | hsa-miR-519e*, hsa-miR-520d-5p |
| DCM-57 | 2 | | hsa-miR-519e*, hsa-miR-200b* |
| DCM-58 | 2 | | hsa-miR-622, hsa-miR-520d-5p |
| DCM-59 | 2 | | hsa-miR-622, hsa-miR-200b* |
| DCM-60 | 3 | | hsa-miR-122*, hsa-miR-1228*, hsa-miR-558 |
| DCM-61 | 3 | | hsa-miR-122*, hsa-miR-1228*, hsa-miR-519e* |
| DCM-62 | 3 | | hsa-miR-122*, hsa-miR-1228*, hsa-miR-622 |
| DCM-63 | 3 | | hsa-miR-122*, hsa-miR-1228*, hsa-miR-520d-5p |
| DCM-64 | 3 | | hsa-miR-122*, hsa-miR-1228*, hsa-miR-200b* |
| DCM-65 | 3 | | hsa-miR-122*, hsa-miR-558, hsa-miR-519e* |
| DCM-66 | 3 | | hsa-miR-122*, hsa-miR-558, hsa-miR-622 |
| DCM-67 | 3 | | hsa-miR-122*, hsa-miR-558, hsa-miR-520d-5p |
| DCM-68 | 3 | | hsa-miR-122*, hsa-miR-558, hsa-miR-200b* |
| DCM-69 | 3 | | hsa-miR-122*, hsa-miR-519e*, hsa-miR-622 |
| DCM-70 | 3 | | hsa-miR-122*, hsa-miR-519e*, hsa-miR-520d-5p |
| DCM-71 | 3 | | hsa-miR-122*, hsa-miR-519e*, hsa-miR-200b* |
| DCM-72 | 3 | | hsa-miR-122*, hsa-miR-622, hsa-miR-520d-5p |
| DCM-73 | 3 | | hsa-miR-122*, hsa-miR-622, hsa-miR-200b* |
| DCM-74 | 3 | | hsa-miR-122*, hsa-miR-520d-5p, hsa-miR-200b* |
| DCM-75 | 3 | | hsa-miR-1228*, hsa-miR-558, hsa-miR-519e* |
| DCM-76 | 3 | | hsa-miR-1228*, hsa-miR-558, hsa-miR-622 |
| DCM-77 | 3 | | hsa-miR-1228*, hsa-miR-558, hsa-miR-520d-5p |
| DCM-78 | 3 | | hsa-miR-1228*, hsa-miR-558, hsa-miR-200b* |
| DCM-79 | 3 | | hsa-miR-1228*, hsa-miR-519e*, hsa-miR-622 |

FIGURE 3B

| | | | |
|---|---|---|---|
| DCM-80 | 3 | | hsa-miR-1228*, hsa-miR-519e*, hsa-miR-520d-5p |
| DCM-81 | 3 | | hsa-miR-1228*, hsa-miR-519e*, hsa-miR-200b* |
| DCM-82 | 3 | | hsa-miR-1228*, hsa-miR-622, hsa-miR-520d-5p |
| DCM-83 | 3 | | hsa-miR-1228*, hsa-miR-622, hsa-miR-200b* |
| DCM-84 | 3 | | hsa-miR-1228*, hsa-miR-520d-5p, hsa-miR-200b* |
| DCM-85 | 3 | | hsa-miR-558, hsa-miR-519e*, hsa-miR-622 |
| DCM-86 | 3 | | hsa-miR-558, hsa-miR-519e*, hsa-miR-520d-5p |
| DCM-87 | 3 | | hsa-miR-558, hsa-miR-519e*, hsa-miR-200b* |
| DCM-88 | 3 | | hsa-miR-558, hsa-miR-622, hsa-miR-520d-5p |
| DCM-89 | 3 | | hsa-miR-558, hsa-miR-622, hsa-miR-200b* |
| DCM-90 | 3 | | hsa-miR-558, hsa-miR-520d-5p, hsa-miR-200b* |
| DCM-91 | 3 | | hsa-miR-519e*, hsa-miR-622, hsa-miR-520d-5p |
| DCM-92 | 3 | | hsa-miR-519e*, hsa-miR-622, hsa-miR-200b* |
| DCM-93 | 3 | | hsa-miR-519e*, hsa-miR-520d-5p, hsa-miR-200b* |
| DCM-94 | 3 | | hsa-miR-622, hsa-miR-520d-5p, hsa-miR-200b* |

FIGURE 3B cont.

Figure 11
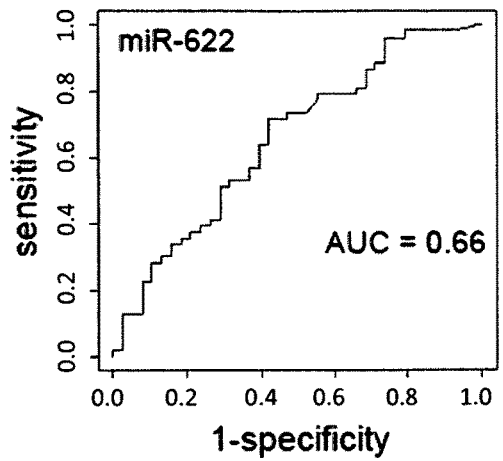
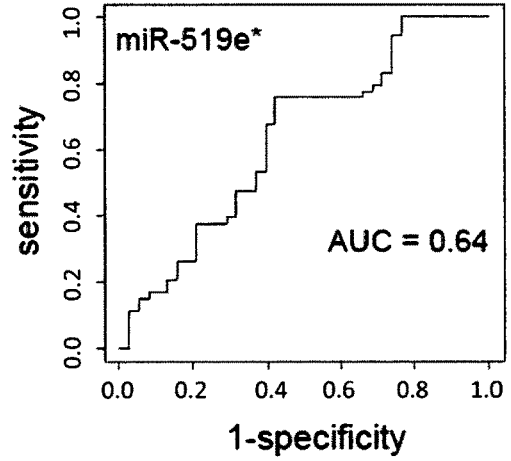
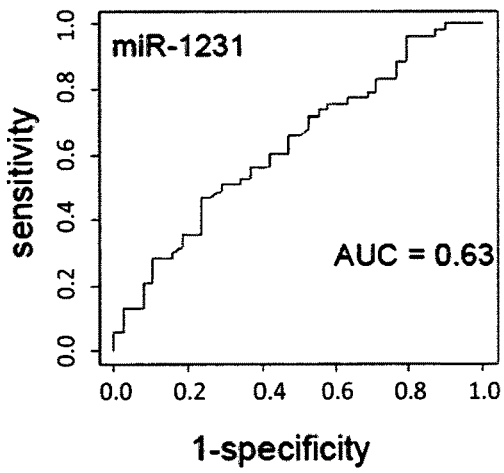
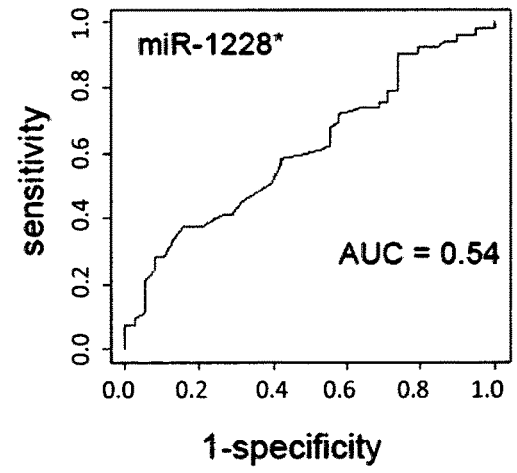
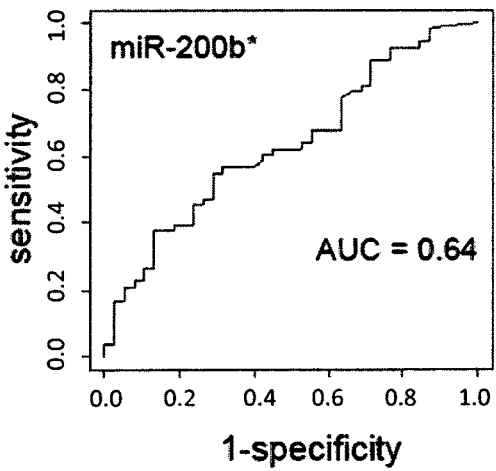

SEQUENCE LISTING

```
<160> NUMBER OF SEQ ID NOS: 387

<210> SEQ ID NO 1
<211> LENGTH: 20
<212> TYPE: RNA
<213> ORGANISM: Homo sapiens

<400> SEQUENCE: 1
cuacaaaggg aagcccuuuc                                                    20

<210> SEQ ID NO 2
<211> LENGTH: 22
<212> TYPE: RNA
<213> ORGANISM: Homo sapiens

<400> SEQUENCE: 2
aaaaguaauu gcggauuuug cc                                                 22

<210> SEQ ID NO 3
<211> LENGTH: 22
<212> TYPE: RNA
<213> ORGANISM: Homo sapiens

<400> SEQUENCE: 3
aacgccauua ucacacuaaa ua                                                 22

<210> SEQ ID NO 4
<211> LENGTH: 22
<212> TYPE: RNA
<213> ORGANISM: Homo sapiens

<400> SEQUENCE: 4
gcugacuccu aguccagggc uc                                                 22

<210> SEQ ID NO 5
<211> LENGTH: 22
<212> TYPE: RNA
<213> ORGANISM: Homo sapiens

<400> SEQUENCE: 5
```
guggguacgg cccaguggggg gg                                                22

<210> SEQ ID NO 6
<211> LENGTH: 19
<212> TYPE: RNA
<213> ORGANISM: Homo sapiens

<400> SEQUENCE: 6
ugagcugcug uaccaaaau                                                     19

<210> SEQ ID NO 7
<211> LENGTH: 21
<212> TYPE: RNA
<213> ORGANISM: Homo sapiens

<400> SEQUENCE: 7
uugggacaua cuuaugcuaa a                                                  21

<210> SEQ ID NO 8
<211> LENGTH: 20
<212> TYPE: RNA
<213> ORGANISM: Homo sapiens

<400> SEQUENCE: 8
cggcucuggg ucugugggga                                                    20

<210> SEQ ID NO 9
<211> LENGTH: 22
<212> TYPE: RNA
<213> ORGANISM: Homo sapiens

<400> SEQUENCE: 9
cuauacggcc uccuagcuuu cc                                                 22

<210> SEQ ID NO 10
<211> LENGTH: 24
<212> TYPE: RNA
<213> ORGANISM: Homo sapiens

<400> SEQUENCE: 10
uugcagcugc cugggaguga cuuc                                               24

<210> SEQ ID NO 11
<211> LENGTH: 22
<212> TYPE: RNA
<213> ORGANISM: Homo sapiens

<400> SEQUENCE: 11
acuggacuua gggucagaag gc                                                 22

<210> SEQ ID NO 12
<211> LENGTH: 22
<212> TYPE: RNA
<213> ORGANISM: Homo sapiens

<400> SEQUENCE: 12
gaaaucaagc gugggugaga cc                                                 22

<210> SEQ ID NO 13
<211> LENGTH: 19
<212> TYPE: RNA
<213> ORGANISM: Homo sapiens

```
<400> SEQUENCE: 13
aggcugcgga auucaggac                                              19

<210> SEQ ID NO 14
<211> LENGTH: 22
<212> TYPE: RNA
<213> ORGANISM: Homo sapiens

<400> SEQUENCE: 14
caucuuacug ggcagcauug ga                                          22

<210> SEQ ID NO 15
<211> LENGTH: 22
<212> TYPE: RNA
<213> ORGANISM: Homo sapiens

<400> SEQUENCE: 15
ugcccugugg acucaguucu gg                                          22

<210> SEQ ID NO 16
<211> LENGTH: 22
<212> TYPE: RNA
<213> ORGANISM: Homo sapiens

<400> SEQUENCE: 16
aaauuauugu acaucggaug ag                                          22

<210> SEQ ID NO 17
<211> LENGTH: 21
<212> TYPE: RNA
<213> ORGANISM: Homo sapiens

<400> SEQUENCE: 17
cacugugucc uuucugcgua g                                           21

<210> SEQ ID NO 18
<211> LENGTH: 21
<212> TYPE: RNA
<213> ORGANISM: Homo sapiens

<400> SEQUENCE: 18
uugugcuuga ucuaaccaug u                                           21

<210> SEQ ID NO 19
<211> LENGTH: 21
<212> TYPE: RNA
<213> ORGANISM: Homo sapiens

<400> SEQUENCE: 19
caagucacua gugguuccgu u                                           21

<210> SEQ ID NO 20
<211> LENGTH: 22
<212> TYPE: RNA
<213> ORGANISM: Homo sapiens

<400> SEQUENCE: 20
uguaaacauc cucgacugga ag                                          22

<210> SEQ ID NO 21
<211> LENGTH: 22
<212> TYPE: RNA
<213> ORGANISM: Homo sapiens
```

```
<400> SEQUENCE: 21
acuuguaugc uagcucaggu ag                                              22

<210> SEQ ID NO 22
<211> LENGTH: 19
<212> TYPE: RNA
<213> ORGANISM: Homo sapiens

<400> SEQUENCE: 22
gggcgccugu gaucccaac                                                  19

<210> SEQ ID NO 23
<211> LENGTH: 21
<212> TYPE: RNA
<213> ORGANISM: Homo sapiens

<400> SEQUENCE: 23 cguacaggc cacugccuug c                                                21

<210> SEQ ID NO 24
<211> LENGTH: 21
<212> TYPE: RNA
<213> ORGANISM: Homo sapiens

<400> SEQUENCE: 24
acagucugcu gagguuggag c                                               21

<210> SEQ ID NO 25
<211> LENGTH: 22
<212> TYPE: RNA
<213> ORGANISM: Homo sapiens

<400> SEQUENCE: 25
cuagguaugg ucccagggau cc                                              22

<210> SEQ ID NO 26
<211> LENGTH: 23
<212> TYPE: RNA
<213> ORGANISM: Homo sapiens

<400> SEQUENCE: 26
ugcaccaugg uugucugagc aug                                             23

<210> SEQ ID NO 27
<211> LENGTH: 20
<212> TYPE: RNA
<213> ORGANISM: Homo sapiens

<400> SEQUENCE: 27 gugucgggc ggacagcugc                                                  20

<210> SEQ ID NO 28
<211> LENGTH: 21
<212> TYPE: RNA
<213> ORGANISM: Homo sapiens

<400> SEQUENCE: 28
gcgacccaua cuugguuuca g                                               21

<210> SEQ ID NO 29
<211> LENGTH: 22
<212> TYPE: RNA
```

<213> ORGANISM: Homo sapiens

<400> SEQUENCE: 29
cagugguuuu acccuauggu ag                                          22

<210> SEQ ID NO 30
<211> LENGTH: 21
<212> TYPE: RNA
<213> ORGANISM: Homo sapiens

<400> SEQUENCE: 30
gugggcgggg gcaggugugu g                                           21

<210> SEQ ID NO 31
<211> LENGTH: 22
<212> TYPE: RNA
<213> ORGANISM: Homo sapiens

<400> SEQUENCE: 31
cccugugccc ggcccacuuc ug                                          22

<210> SEQ ID NO 32
<211> LENGTH: 20
<212> TYPE: RNA
<213> ORGANISM: Homo sapiens

<400> SEQUENCE: 32
uacaguauag augauguacu                                             20

<210> SEQ ID NO 33
<211> LENGTH: 22
<212> TYPE: RNA
<213> ORGANISM: Homo sapiens

<400> SEQUENCE: 33
caucuuccag uacaguguug ga                                          22

<210> SEQ ID NO 34
<211> LENGTH: 22
<212> TYPE: RNA
<213> ORGANISM: Homo sapiens

<400> SEQUENCE: 34
uucuccaaaa gggagcacuu uc                                          22

<210> SEQ ID NO 35
<211> LENGTH: 19
<212> TYPE: RNA
<213> ORGANISM: Homo sapiens

<400> SEQUENCE: 35
gaugaugcug cugaugcug                                              19

<210> SEQ ID NO 36
<211> LENGTH: 22
<212> TYPE: RNA
<213> ORGANISM: Homo sapiens

<400> SEQUENCE: 36
caagcucgcu ucuauggguc ug                                          22

<210> SEQ ID NO 37
<211> LENGTH: 22

```
<212> TYPE: RNA
<213> ORGANISM: Homo sapiens

<400> SEQUENCE: 37
aaagugcuuc ucuuuggugg gu                                    22

<210> SEQ ID NO 38
<211> LENGTH: 22
<212> TYPE: RNA
<213> ORGANISM: Homo sapiens

<400> SEQUENCE: 38
aguuuugcau aguugcacua ca                                    22

<210> SEQ ID NO 39
<211> LENGTH: 27
<212> TYPE: RNA
<213> ORGANISM: Homo sapiens

<400> SEQUENCE: 39
cacuguaggu gaugugaga gugggca                                27

<210> SEQ ID NO 40
<211> LENGTH: 22
<212> TYPE: RNA
<213> ORGANISM: Homo sapiens

<400> SEQUENCE: 40
uuguacaugg uaggcuuuca uu                                    22

<210> SEQ ID NO 41
<211> LENGTH: 22
<212> TYPE: RNA
<213> ORGANISM: Homo sapiens

<400> SEQUENCE: 41
aggugguccg uggcgcguuc gc                                    22

<210> SEQ ID NO 42
<211> LENGTH: 20
<212> TYPE: RNA
<213> ORGANISM: Homo sapiens

<400> SEQUENCE: 42 gugguggaa augcuucugc                                        20

<210> SEQ ID NO 43
<211> LENGTH: 23
<212> TYPE: RNA
<213> ORGANISM: Homo sapiens

<400> SEQUENCE: 43
ugugcaaauc caugcaaaac uga                                   23

<210> SEQ ID NO 44
<211> LENGTH: 21
<212> TYPE: RNA
<213> ORGANISM: Homo sapiens

<400> SEQUENCE: 44
aucauagagg aaaauccacg u                                     21

<210> SEQ ID NO 45
```

```
<211> LENGTH: 21
<212> TYPE: RNA
<213> ORGANISM: Homo sapiens

<400> SEQUENCE: 45
gcaguccaug ggcauauaca c                                              21

<210> SEQ ID NO 46
<211> LENGTH: 22
<212> TYPE: RNA
<213> ORGANISM: Homo sapiens

<400> SEQUENCE: 46
ggugcagugc ugcaucucug gu                                             22

<210> SEQ ID NO 47
<211> LENGTH: 22
<212> TYPE: RNA
<213> ORGANISM: Homo sapiens

<400> SEQUENCE: 47 ugugcacuc gaugaccacu gu                                              22

<210> SEQ ID NO 48
<211> LENGTH: 22
<212> TYPE: RNA
<213> ORGANISM: Homo sapiens

<400> SEQUENCE: 48
acuguugcua auaugcaacu cu                                             22

<210> SEQ ID NO 49
<211> LENGTH: 21
<212> TYPE: RNA
<213> ORGANISM: Homo sapiens

<400> SEQUENCE: 49
cuucuugugc ucuaggauug u                                              21

<210> SEQ ID NO 50
<211> LENGTH: 23
<212> TYPE: RNA
<213> ORGANISM: Homo sapiens

<400> SEQUENCE: 50 ugcacucgg cucggcccac uac                                             23

<210> SEQ ID NO 51
<211> LENGTH: 23
<212> TYPE: RNA
<213> ORGANISM: Homo sapiens

<400> SEQUENCE: 51
aucccuugca ggggcuguug ggu                                            23

<210> SEQ ID NO 52
<211> LENGTH: 19
<212> TYPE: RNA
<213> ORGANISM: Homo sapiens

<400> SEQUENCE: 52
agguugacau acguuuccc                                                 19
```

```
<210> SEQ ID NO 53
<211> LENGTH: 22
<212> TYPE: RNA
<213> ORGANISM: Homo sapiens

<400> SEQUENCE: 53
uaacugguug aacaacugaa cc                                          22

<210> SEQ ID NO 54
<211> LENGTH: 23
<212> TYPE: RNA
<213> ORGANISM: Homo sapiens

<400> SEQUENCE: 54
ugugcaaauc uaugcaaaac uga                                         23

<210> SEQ ID NO 55
<211> LENGTH: 21
<212> TYPE: RNA
<213> ORGANISM: Homo sapiens

<400> SEQUENCE: 55
aauaauacau gguugaucuu u                                           21

<210> SEQ ID NO 56
<211> LENGTH: 20
<212> TYPE: RNA
<213> ORGANISM: Homo sapiens

<400> SEQUENCE: 56
gucccugagu guauguggug                                             20

<210> SEQ ID NO 57
<211> LENGTH: 26
<212> TYPE: RNA
<213> ORGANISM: Homo sapiens

<400> SEQUENCE: 57
gaugaugaug gcagcaaauu cugaaa                                      26

<210> SEQ ID NO 58
<211> LENGTH: 22
<212> TYPE: RNA
<213> ORGANISM: Homo sapiens

<400> SEQUENCE: 58
gagagcagug uguguugccu gg                                          22

<210> SEQ ID NO 59
<211> LENGTH: 23
<212> TYPE: RNA
<213> ORGANISM: Homo sapiens

<400> SEQUENCE: 59
uggaguccag gaaucugcau uuu                                         23

<210> SEQ ID NO 60
<211> LENGTH: 22
<212> TYPE: RNA
<213> ORGANISM: Homo sapiens

<400> SEQUENCE: 60
cggaugagca aagaaagugg uu                                          22
```

```
<210> SEQ ID NO 61
<211> LENGTH: 22
<212> TYPE: RNA
<213> ORGANISM: Homo sapiens

<400> SEQUENCE: 61
agucauugga ggguuugagc ag                                         22

<210> SEQ ID NO 62
<211> LENGTH: 18
<212> TYPE: RNA
<213> ORGANISM: Homo sapiens

<400> SEQUENCE: 62
ugcuuccuuu cagagggu                                              18

<210> SEQ ID NO 63
<211> LENGTH: 21
<212> TYPE: RNA
<213> ORGANISM: Homo sapiens

<400> SEQUENCE: 63
ucuaguaaga guggcagucg a                                          21

<210> SEQ ID NO 64
<211> LENGTH: 22
<212> TYPE: RNA
<213> ORGANISM: Homo sapiens

<400> SEQUENCE: 64
cuuggcaccu agcaagcacu ca                                         22

<210> SEQ ID NO 65
<211> LENGTH: 22
<212> TYPE: RNA
<213> ORGANISM: Homo sapiens

<400> SEQUENCE: 65
aacaauaucc uggugcugag ug                                         22

<210> SEQ ID NO 66
<211> LENGTH: 22
<212> TYPE: RNA
<213> ORGANISM: Homo sapiens

<400> SEQUENCE: 66
uauguaacau gguccacuaa cu                                         22

<210> SEQ ID NO 67
<211> LENGTH: 25
<212> TYPE: RNA
<213> ORGANISM: Homo sapiens

<400> SEQUENCE: 67
uaggcagugu auugcuagcg gcugu                                      25

<210> SEQ ID NO 68
<211> LENGTH: 22
<212> TYPE: RNA
<213> ORGANISM: Homo sapiens

<400> SEQUENCE: 68
caaaguuuaa gauccuugaa gu                                         22
```

<210> SEQ ID NO 69
<211> LENGTH: 18
<212> TYPE: RNA
<213> ORGANISM: Homo sapiens

<400> SEQUENCE: 69
uucacaggga ggugucau                                             18

<210> SEQ ID NO 70
<211> LENGTH: 22
<212> TYPE: RNA
<213> ORGANISM: Homo sapiens

<400> SEQUENCE: 70
cucuagaggg aagcgcuuuc ug                                        22

<210> SEQ ID NO 71
<211> LENGTH: 22
<212> TYPE: RNA
<213> ORGANISM: Homo sapiens

<400> SEQUENCE: 71
ggagaaauua uccuuggugu gu                                        22

<210> SEQ ID NO 72
<211> LENGTH: 20
<212> TYPE: RNA
<213> ORGANISM: Homo sapiens

<400> SEQUENCE: 72
cgugccaccc uuuucccag                                            20

<210> SEQ ID NO 73
<211> LENGTH: 22
<212> TYPE: RNA
<213> ORGANISM: Homo sapiens

<400> SEQUENCE: 73
aauugcacuu uagcaauggu ga                                        22

<210> SEQ ID NO 74
<211> LENGTH: 22
<212> TYPE: RNA
<213> ORGANISM: Homo sapiens

<400> SEQUENCE: 74 ugauuggu ac gucuguggu ag                                        22

<210> SEQ ID NO 75
<211> LENGTH: 22
<212> TYPE: RNA
<213> ORGANISM: Homo sapiens

<400> SEQUENCE: 75
cugggagaag gcuguuuacu cu                                        22

<210> SEQ ID NO 76
<211> LENGTH: 22
<212> TYPE: RNA
<213> ORGANISM: Homo sapiens

<400> SEQUENCE: 76

| | |
|---|---|
| gacuauagaa cuucccccu ca | 22 |

<210> SEQ ID NO 77
<211> LENGTH: 21
<212> TYPE: RNA
<213> ORGANISM: Homo sapiens

<400> SEQUENCE: 77

| | |
|---|---|
| cuccagaggg aaguacuuuc u | 21 |

<210> SEQ ID NO 78
<211> LENGTH: 22
<212> TYPE: RNA
<213> ORGANISM: Homo sapiens

<400> SEQUENCE: 78

| | |
|---|---|
| uauugcacuu gucccggccu gu | 22 |

<210> SEQ ID NO 79
<211> LENGTH: 25
<212> TYPE: RNA
<213> ORGANISM: Homo sapiens

<400> SEQUENCE: 79

| | |
|---|---|
| ggcggaggga aguagguccg uuggu | 25 |

<210> SEQ ID NO 80
<211> LENGTH: 22
<212> TYPE: RNA
<213> ORGANISM: Homo sapiens

<400> SEQUENCE: 80

| | |
|---|---|
| accuggcaua caauguagau uu | 22 |

<210> SEQ ID NO 81
<211> LENGTH: 22
<212> TYPE: RNA
<213> ORGANISM: Homo sapiens

<400> SEQUENCE: 81

| | |
|---|---|
| agaggcuggc cgugaugaau uc | 22 |

<210> SEQ ID NO 82
<211> LENGTH: 21
<212> TYPE: RNA
<213> ORGANISM: Homo sapiens

<400> SEQUENCE: 82

| | |
|---|---|
| caaagaggaa ggucccauua c | 21 |

<210> SEQ ID NO 83
<211> LENGTH: 22
<212> TYPE: RNA
<213> ORGANISM: Homo sapiens

<400> SEQUENCE: 83

| | |
|---|---|
| uucccuuugu cauccuucgc cu | 22 |

<210> SEQ ID NO 84
<211> LENGTH: 18
<212> TYPE: RNA
<213> ORGANISM: Homo sapiens

<400> SEQUENCE: 84
ucagcuggcc cucauuuc                                                         18

<210> SEQ ID NO 85
<211> LENGTH: 23
<212> TYPE: RNA
<213> ORGANISM: Homo sapiens

<400> SEQUENCE: 85
ucucuggagg gaagcacuuu cug                                                   23

<210> SEQ ID NO 86
<211> LENGTH: 22
<212> TYPE: RNA
<213> ORGANISM: Homo sapiens

<400> SEQUENCE: 86
uuauaaagca augagacuga uu                                                    22

<210> SEQ ID NO 87
<211> LENGTH: 21
<212> TYPE: RNA
<213> ORGANISM: Homo sapiens

<400> SEQUENCE: 87
uaaaguaaau augcaccaaa a                                                     21

<210> SEQ ID NO 88
<211> LENGTH: 20
<212> TYPE: RNA
<213> ORGANISM: Homo sapiens

<400> SEQUENCE: 88
ucguuugccu uuuucugcuu                                                       20

<210> SEQ ID NO 89
<211> LENGTH: 23
<212> TYPE: RNA
<213> ORGANISM: Homo sapiens

<400> SEQUENCE: 89
aggaagcccu ggaggggcug gag                                                   23

<210> SEQ ID NO 90
<211> LENGTH: 21
<212> TYPE: RNA
<213> ORGANISM: Homo sapiens

<400> SEQUENCE: 90
aagcauucuu ucauugguug g                                                     21

<210> SEQ ID NO 91
<211> LENGTH: 18
<212> TYPE: RNA
<213> ORGANISM: Homo sapiens

<400> SEQUENCE: 91
cagggaggug aaugugau                                                         18

<210> SEQ ID NO 92
<211> LENGTH: 22
<212> TYPE: RNA
<213> ORGANISM: Homo sapiens

```
<400> SEQUENCE: 92
uuugaggcua cagugagaug ug                                              22

<210> SEQ ID NO 93
<211> LENGTH: 22
<212> TYPE: RNA
<213> ORGANISM: Homo sapiens

<400> SEQUENCE: 93
uaaugccccu aaaaauccuu au                                              22

<210> SEQ ID NO 94
<211> LENGTH: 22
<212> TYPE: RNA
<213> ORGANISM: Homo sapiens

<400> SEQUENCE: 94
caaucagcaa guauacugcc cu                                              22

<210> SEQ ID NO 95
<211> LENGTH: 22
<212> TYPE: RNA
<213> ORGANISM: Homo sapiens

<400> SEQUENCE: 95
ucggauccgu cugagcuugg cu                                              22

<210> SEQ ID NO 96
<211> LENGTH: 21
<212> TYPE: RNA
<213> ORGANISM: Homo sapiens

<400> SEQUENCE: 96
caacaccagu cgaugggcug u                                               21

<210> SEQ ID NO 97
<211> LENGTH: 22
<212> TYPE: RNA
<213> ORGANISM: Homo sapiens

<400> SEQUENCE: 97
caauuuagug ugugugauau uu                                              22

<210> SEQ ID NO 98
<211> LENGTH: 22
<212> TYPE: RNA
<213> ORGANISM: Homo sapiens

<400> SEQUENCE: 98
cuauacaguc uacugucuuu cc                                              22

<210> SEQ ID NO 99
<211> LENGTH: 22
<212> TYPE: RNA
<213> ORGANISM: Homo sapiens

<400> SEQUENCE: 99
uguaaacauc cuugacugga ag                                              22

<210> SEQ ID NO 100
<211> LENGTH: 22
<212> TYPE: RNA
<213> ORGANISM: Homo sapiens
```

```
<400> SEQUENCE: 100
aucuggaggu aagaagcacu uu                                              22

<210> SEQ ID NO 101
<211> LENGTH: 21
<212> TYPE: RNA
<213> ORGANISM: Homo sapiens

<400> SEQUENCE: 101
aguuaaugaa uccuggaaag u                                               21

<210> SEQ ID NO 102
<211> LENGTH: 20
<212> TYPE: RNA
<213> ORGANISM: Homo sapiens

<400> SEQUENCE: 102
aggguguuuc ucucaucucu                                                 20

<210> SEQ ID NO 103
<211> LENGTH: 23
<212> TYPE: RNA
<213> ORGANISM: Homo sapiens

<400> SEQUENCE: 103
uaaaucccau ggugccuucu ccu                                             23

<210> SEQ ID NO 104
<211> LENGTH: 22
<212> TYPE: RNA
<213> ORGANISM: Homo sapiens

<400> SEQUENCE: 104
agacuuccca uuugaaggug gc                                              22

<210> SEQ ID NO 105
<211> LENGTH: 22
<212> TYPE: RNA
<213> ORGANISM: Homo sapiens

<400> SEQUENCE: 105
uguaaacauc cccgacugga ag                                              22

<210> SEQ ID NO 106
<211> LENGTH: 22
<212> TYPE: RNA
<213> ORGANISM: Homo sapiens

<400> SEQUENCE: 106
uacguagaua uauauguauu uu                                              22

<210> SEQ ID NO 107
<211> LENGTH: 22
<212> TYPE: RNA
<213> ORGANISM: Homo sapiens

<400> SEQUENCE: 107
gccugcuggg guggaaccug gu                                              22

<210> SEQ ID NO 108
<211> LENGTH: 22
<212> TYPE: RNA
```

```
<213> ORGANISM: Homo sapiens

<400> SEQUENCE: 108
ucaguaaaug uuuauuagau ga                                         22

<210> SEQ ID NO 109
<211> LENGTH: 22
<212> TYPE: RNA
<213> ORGANISM: Homo sapiens

<400> SEQUENCE: 109
aaaaguaauc gcgguuuuug uc                                         22

<210> SEQ ID NO 110
<211> LENGTH: 22
<212> TYPE: RNA
<213> ORGANISM: Homo sapiens

<400> SEQUENCE: 110
ccuguucucc auuacuuggc uc                                         22

<210> SEQ ID NO 111
<211> LENGTH: 24
<212> TYPE: RNA
<213> ORGANISM: Homo sapiens

<400> SEQUENCE: 111
agccuggaag cuggagccug cagu                                       24

<210> SEQ ID NO 112
<211> LENGTH: 19
<212> TYPE: RNA
<213> ORGANISM: Homo sapiens

<400> SEQUENCE: 112
uggauuuuug gaucaggga                                             19

<210> SEQ ID NO 113
<211> LENGTH: 22
<212> TYPE: RNA
<213> ORGANISM: Homo sapiens

<400> SEQUENCE: 113
uaugcauugu auuuuuaggu cc                                         22

<210> SEQ ID NO 114
<211> LENGTH: 22
<212> TYPE: RNA
<213> ORGANISM: Homo sapiens

<400> SEQUENCE: 114
uggguggucu ggagauuugu gc                                         22

<210> SEQ ID NO 115
<211> LENGTH: 27
<212> TYPE: RNA
<213> ORGANISM: Homo sapiens

<400> SEQUENCE: 115
accuucuugu auaagcacug ugcuaaa                                    27

<210> SEQ ID NO 116
<211> LENGTH: 22
```

<212> TYPE: RNA
<213> ORGANISM: Homo sapiens

<400> SEQUENCE: 116
uccuucauuc caccggaguc ug					22

<210> SEQ ID NO 117
<211> LENGTH: 22
<212> TYPE: RNA
<213> ORGANISM: Homo sapiens

<400> SEQUENCE: 117
cugccaauuc cauaggucac ag					22

<210> SEQ ID NO 118
<211> LENGTH: 20
<212> TYPE: RNA
<213> ORGANISM: Homo sapiens

<400> SEQUENCE: 118
ggggagcugu ggaagcagua					20

<210> SEQ ID NO 119
<211> LENGTH: 23
<212> TYPE: RNA
<213> ORGANISM: Homo sapiens

<400> SEQUENCE: 119
caagucuuau uugagcaccu guu					23

<210> SEQ ID NO 120
<211> LENGTH: 23
<212> TYPE: RNA
<213> ORGANISM: Homo sapiens

<400> SEQUENCE: 120
aacauucauu guguucggug ggu					23

<210> SEQ ID NO 121
<211> LENGTH: 18
<212> TYPE: RNA
<213> ORGANISM: Homo sapiens

<400> SEQUENCE: 121
gucccuguuc aggcgcca					18

<210> SEQ ID NO 122
<211> LENGTH: 22
<212> TYPE: RNA
<213> ORGANISM: Homo sapiens

<400> SEQUENCE: 122 ugguggggccg cagaacaugu gc					22

<210> SEQ ID NO 123
<211> LENGTH: 24
<212> TYPE: RNA
<213> ORGANISM: Homo sapiens

<400> SEQUENCE: 123
ccagacagaa uucuaugcac uuuc					24

<210> SEQ ID NO 124

```
<211> LENGTH: 21
<212> TYPE: RNA
<213> ORGANISM: Homo sapiens

<400> SEQUENCE: 124
cauaaaguag aaagcacuac u                                              21

<210> SEQ ID NO 125
<211> LENGTH: 22
<212> TYPE: RNA
<213> ORGANISM: Homo sapiens

<400> SEQUENCE: 125
cucuagaggg aagcgcuuuc ug                                             22

<210> SEQ ID NO 126
<211> LENGTH: 22
<212> TYPE: RNA
<213> ORGANISM: Homo sapiens

<400> SEQUENCE: 126
uugggaucau uuugcaucca ua                                             22

<210> SEQ ID NO 127
<211> LENGTH: 23
<212> TYPE: RNA
<213> ORGANISM: Homo sapiens

<400> SEQUENCE: 127
aucaacagac auuaauuggg cgc                                            23

<210> SEQ ID NO 128
<211> LENGTH: 22
<212> TYPE: RNA
<213> ORGANISM: Homo sapiens

<400> SEQUENCE: 128
agaaggaaau ugaaucauu ua                                              22

<210> SEQ ID NO 129
<211> LENGTH: 22
<212> TYPE: RNA
<213> ORGANISM: Homo sapiens

<400> SEQUENCE: 129
ggaggggucc cgcacuggga gg                                             22

<210> SEQ ID NO 130
<211> LENGTH: 21
<212> TYPE: RNA
<213> ORGANISM: Homo sapiens

<400> SEQUENCE: 130
acuggacuug gagucagaag g                                              21

<210> SEQ ID NO 131
<211> LENGTH: 21
<212> TYPE: RNA
<213> ORGANISM: Homo sapiens

<400> SEQUENCE: 131
aacaggugac ugguuagaca a                                              21
```

```
<210> SEQ ID NO 132
<211> LENGTH: 22
<212> TYPE: RNA
<213> ORGANISM: Homo sapiens

<400> SEQUENCE: 132
cuccuacaua uuagcauuaa ca                                              22

<210> SEQ ID NO 133
<211> LENGTH: 22
<212> TYPE: RNA
<213> ORGANISM: Homo sapiens

<400> SEQUENCE: 133
ucugcaagug ucagaggcga gg                                              22

<210> SEQ ID NO 134
<211> LENGTH: 22
<212> TYPE: RNA
<213> ORGANISM: Homo sapiens

<400> SEQUENCE: 134
cuugguucag ggaggguccc ca                                              22

<210> SEQ ID NO 135
<211> LENGTH: 22
<212> TYPE: RNA
<213> ORGANISM: Homo sapiens

<400> SEQUENCE: 135
cuauacgacc ugcugccuuu cu                                              22

<210> SEQ ID NO 136
<211> LENGTH: 22
<212> TYPE: RNA
<213> ORGANISM: Homo sapiens

<400> SEQUENCE: 136
gaaggcgcuu cccuuuagag cg                                              22

<210> SEQ ID NO 137
<211> LENGTH: 22
<212> TYPE: RNA
<213> ORGANISM: Homo sapiens

<400> SEQUENCE: 137
ucgacagcac gacacugccu uc                                              22

<210> SEQ ID NO 138
<211> LENGTH: 22
<212> TYPE: RNA
<213> ORGANISM: Homo sapiens

<400> SEQUENCE: 138
agaguugagu cuggacgucc cg                                              22

<210> SEQ ID NO 139
<211> LENGTH: 22
<212> TYPE: RNA
<213> ORGANISM: Homo sapiens

<400> SEQUENCE: 139
aaucacuaac cacacggcca gg                                              22
```

```
<210> SEQ ID NO 140
<211> LENGTH: 23
<212> TYPE: RNA
<213> ORGANISM: Homo sapiens

<400> SEQUENCE: 140
uucauuuggu auaaaccgcg auu                                               23

<210> SEQ ID NO 141
<211> LENGTH: 21
<212> TYPE: RNA
<213> ORGANISM: Homo sapiens

<400> SEQUENCE: 141
gcuaguccug acucagccag u                                                 21

<210> SEQ ID NO 142
<211> LENGTH: 23
<212> TYPE: RNA
<213> ORGANISM: Homo sapiens

<400> SEQUENCE: 142
ucugcucaua ccccaugguu ucu                                               23

<210> SEQ ID NO 143
<211> LENGTH: 23
<212> TYPE: RNA
<213> ORGANISM: Homo sapiens

<400> SEQUENCE: 143
ugagugugug ugugugagug ugu                                               23

<210> SEQ ID NO 144
<211> LENGTH: 22
<212> TYPE: RNA
<213> ORGANISM: Homo sapiens

<400> SEQUENCE: 144
cacccguaga accgaccuug cg                                                22

<210> SEQ ID NO 145
<211> LENGTH: 24
<212> TYPE: RNA
<213> ORGANISM: Homo sapiens

<400> SEQUENCE: 145
ucccugagac ccuuuaaccu guga                                              24

<210> SEQ ID NO 146
<211> LENGTH: 25
<212> TYPE: RNA
<213> ORGANISM: Homo sapiens

<400> SEQUENCE: 146 aggggugguq uugggacagc uccgu                                             25

<210> SEQ ID NO 147
<211> LENGTH: 21
<212> TYPE: RNA
<213> ORGANISM: Homo sapiens

<400> SEQUENCE: 147
agugaaugau ggguucugac c                                                 21
```

<210> SEQ ID NO 148
<211> LENGTH: 22
<212> TYPE: RNA
<213> ORGANISM: Homo sapiens

<400> SEQUENCE: 148
ugucuacuac uggagacacu gg                                              22

<210> SEQ ID NO 149
<211> LENGTH: 22
<212> TYPE: RNA
<213> ORGANISM: Homo sapiens

<400> SEQUENCE: 149
caaaaaccac aguuucuuuu gc                                              22

<210> SEQ ID NO 150
<211> LENGTH: 23
<212> TYPE: RNA
<213> ORGANISM: Homo sapiens

<400> SEQUENCE: 150
uggugcggag agggcccaca gug                                             23

<210> SEQ ID NO 151
<211> LENGTH: 20
<212> TYPE: RNA
<213> ORGANISM: Homo sapiens

<400> SEQUENCE: 151
cuuccucguc ugucugcccc                                                 20

<210> SEQ ID NO 152
<211> LENGTH: 23
<212> TYPE: RNA
<213> ORGANISM: Homo sapiens

<400> SEQUENCE: 152
cagugcaaug auauugucaa agc                                             23

<210> SEQ ID NO 153
<211> LENGTH: 22
<212> TYPE: RNA
<213> ORGANISM: Homo sapiens

<400> SEQUENCE: 153
aggcagugua uuguuagcug gc                                              22

<210> SEQ ID NO 154
<211> LENGTH: 22
<212> TYPE: RNA
<213> ORGANISM: Homo sapiens

<400> SEQUENCE: 154
cuguugccac uaaccucaac cu                                              22

<210> SEQ ID NO 155
<211> LENGTH: 20
<212> TYPE: RNA
<213> ORGANISM: Homo sapiens

<400> SEQUENCE: 155
cuguaugccc ucaccgcuca                                              20

<210> SEQ ID NO 156
<211> LENGTH: 22
<212> TYPE: RNA
<213> ORGANISM: Homo sapiens

<400> SEQUENCE: 156
uggcucaguu cagcaggaac ag                                           22

<210> SEQ ID NO 157
<211> LENGTH: 21
<212> TYPE: RNA
<213> ORGANISM: Homo sapiens

<400> SEQUENCE: 157
uggcagggag gcugggaggg g                                            21

<210> SEQ ID NO 158
<211> LENGTH: 22
<212> TYPE: RNA
<213> ORGANISM: Homo sapiens

<400> SEQUENCE: 158
ggagacgcgg cccuguugga gu                                           22

<210> SEQ ID NO 159
<211> LENGTH: 23
<212> TYPE: RNA
<213> ORGANISM: Homo sapiens

<400> SEQUENCE: 159
guccaguuuu cccaggaauc ccu                                          23

<210> SEQ ID NO 160
<211> LENGTH: 21
<212> TYPE: RNA
<213> ORGANISM: Homo sapiens

<400> SEQUENCE: 160
uuggccacaa uggguuagaa c                                            21

<210> SEQ ID NO 161
<211> LENGTH: 21
<212> TYPE: RNA
<213> ORGANISM: Homo sapiens

<400> SEQUENCE: 161
cuagacugaa gcuccuugag g                                            21

<210> SEQ ID NO 162
<211> LENGTH: 22
<212> TYPE: RNA
<213> ORGANISM: Homo sapiens

<400> SEQUENCE: 162
acugcaguga aggcacuugu ag                                           22

<210> SEQ ID NO 163
<211> LENGTH: 22
<212> TYPE: RNA
<213> ORGANISM: Homo sapiens

<400> SEQUENCE: 163

```
gguccagagg ggagauaggu uc                                          22

<210> SEQ ID NO 164
<211> LENGTH: 22
<212> TYPE: RNA
<213> ORGANISM: Homo sapiens

<400> SEQUENCE: 164 cguacagcc uccuagcuuu cc                                           22

<210> SEQ ID NO 165
<211> LENGTH: 22
<212> TYPE: RNA
<213> ORGANISM: Homo sapiens

<400> SEQUENCE: 165
ugagaacuga auuccauggg uu                                          22

<210> SEQ ID NO 166
<211> LENGTH: 21
<212> TYPE: RNA
<213> ORGANISM: Homo sapiens

<400> SEQUENCE: 166
aggaggcagc gcucucagga c                                           21

<210> SEQ ID NO 167
<211> LENGTH: 22
<212> TYPE: RNA
<213> ORGANISM: Homo sapiens

<400> SEQUENCE: 167
acuguaguau gggcacuucc ag                                          22

<210> SEQ ID NO 168
<211> LENGTH: 22
<212> TYPE: RNA
<213> ORGANISM: Homo sapiens

<400> SEQUENCE: 168
ccuauucuug guuacuugca cg                                          22

<210> SEQ ID NO 169
<211> LENGTH: 22
<212> TYPE: RNA
<213> ORGANISM: Homo sapiens

<400> SEQUENCE: 169
gaaguuguuc gugguggauu cg                                          22

<210> SEQ ID NO 170
<211> LENGTH: 22
<212> TYPE: RNA
<213> ORGANISM: Homo sapiens

<400> SEQUENCE: 170
ugccuacuga gcugaaacac ag                                          22

<210> SEQ ID NO 171
<211> LENGTH: 22
<212> TYPE: RNA
<213> ORGANISM: Homo sapiens
```

<400> SEQUENCE: 171
cacuggcucc uuucugggua ga                                        22

<210> SEQ ID NO 172
<211> LENGTH: 21
<212> TYPE: RNA
<213> ORGANISM: Homo sapiens

<400> SEQUENCE: 172
gaagugugcc guggugyguc u                                         21

<210> SEQ ID NO 173
<211> LENGTH: 17
<212> TYPE: RNA
<213> ORGANISM: Homo sapiens

<400> SEQUENCE: 173
uaauugcuuc cauguuu                                              17

<210> SEQ ID NO 174
<211> LENGTH: 23
<212> TYPE: RNA
<213> ORGANISM: Homo sapiens

<400> SEQUENCE: 174
ucuuggagua ggucauuggg ugg                                       23

<210> SEQ ID NO 175
<211> LENGTH: 22
<212> TYPE: RNA
<213> ORGANISM: Homo sapiens

<400> SEQUENCE: 175
accaucgacc guugauugua cc                                        22

<210> SEQ ID NO 176
<211> LENGTH: 21
<212> TYPE: RNA
<213> ORGANISM: Homo sapiens

<400> SEQUENCE: 176
uaggacacau ggucuacuuc u                                         21

<210> SEQ ID NO 177
<211> LENGTH: 20
<212> TYPE: RNA
<213> ORGANISM: Homo sapiens

<400> SEQUENCE: 177
uguuuugaua acaguaaugu                                           20

<210> SEQ ID NO 178
<211> LENGTH: 21
<212> TYPE: RNA
<213> ORGANISM: Homo sapiens

<400> SEQUENCE: 178
ccaguccugu gccugccgcc u                                         21

<210> SEQ ID NO 179
<211> LENGTH: 22
<212> TYPE: RNA
<213> ORGANISM: Homo sapiens

<400> SEQUENCE: 179
uuggggaaac ggccgcugag ug					22

<210> SEQ ID NO 180
<211> LENGTH: 22
<212> TYPE: RNA
<213> ORGANISM: Homo sapiens

<400> SEQUENCE: 180
uggugggcac agaaucugga cu					22

<210> SEQ ID NO 181
<211> LENGTH: 22
<212> TYPE: RNA
<213> ORGANISM: Homo sapiens

<400> SEQUENCE: 181
uaugugccuu uggacuacau cg					22

<210> SEQ ID NO 182
<211> LENGTH: 22
<212> TYPE: RNA
<213> ORGANISM: Homo sapiens

<400> SEQUENCE: 182
ugguugacca uagaacaugc gc					22

<210> SEQ ID NO 183
<211> LENGTH: 23
<212> TYPE: RNA
<213> ORGANISM: Homo sapiens

<400> SEQUENCE: 183
gaagugcuuc gauuuugggg ugu					23

<210> SEQ ID NO 184
<211> LENGTH: 25
<212> TYPE: RNA
<213> ORGANISM: Homo sapiens

<400> SEQUENCE: 184
gcugggcagg gcuucugagc uccuu					25

<210> SEQ ID NO 185
<211> LENGTH: 21
<212> TYPE: RNA
<213> ORGANISM: Homo sapiens

<400> SEQUENCE: 185
agaccuggcc cagaccucag c						21

<210> SEQ ID NO 186
<211> LENGTH: 23
<212> TYPE: RNA
<213> ORGANISM: Homo sapiens

<400> SEQUENCE: 186
uuauugcuua agaauacgcg uag					23

<210> SEQ ID NO 187
<211> LENGTH: 21
<212> TYPE: RNA

```
<213> ORGANISM: Homo sapiens

<400> SEQUENCE: 187
uugcucacug uucuucccua g                                              21

<210> SEQ ID NO 188
<211> LENGTH: 21
<212> TYPE: RNA
<213> ORGANISM: Homo sapiens

<400> SEQUENCE: 188
gaaagcgcuu cucuuuagag g                                              21

<210> SEQ ID NO 189
<211> LENGTH: 21
<212> TYPE: RNA
<213> ORGANISM: Homo sapiens

<400> SEQUENCE: 189
cuccagaggg augcacuuuc u                                              21

<210> SEQ ID NO 190
<211> LENGTH: 22
<212> TYPE: RNA
<213> ORGANISM: Homo sapiens

<400> SEQUENCE: 190
uagucccuuc cuugaagcgg uc                                             22

<210> SEQ ID NO 191
<211> LENGTH: 22
<212> TYPE: RNA
<213> ORGANISM: Homo sapiens

<400> SEQUENCE: 191
ccucccacac ccaaggcuug ca                                             22

<210> SEQ ID NO 192
<211> LENGTH: 22
<212> TYPE: RNA
<213> ORGANISM: Homo sapiens

<400> SEQUENCE: 192
gguggcccgg ccgugccuga gg                                             22

<210> SEQ ID NO 193
<211> LENGTH: 22
<212> TYPE: RNA
<213> ORGANISM: Homo sapiens

<400> SEQUENCE: 193
uucacauugu gcuacugucu gc                                             22

<210> SEQ ID NO 194
<211> LENGTH: 21
<212> TYPE: RNA
<213> ORGANISM: Homo sapiens

<400> SEQUENCE: 194
ugacaacuau ggaugagcuc u                                              21

<210> SEQ ID NO 195
<211> LENGTH: 22
```

```
<212> TYPE: RNA
<213> ORGANISM: Homo sapiens

<400> SEQUENCE: 195
uauaccucag uuuuaucagg ug                                              22

<210> SEQ ID NO 196
<211> LENGTH: 22
<212> TYPE: RNA
<213> ORGANISM: Homo sapiens

<400> SEQUENCE: 196
aaaaccgucu aguuacaguu gu                                              22

<210> SEQ ID NO 197
<211> LENGTH: 21
<212> TYPE: RNA
<213> ORGANISM: Homo sapiens

<400> SEQUENCE: 197
uaaggcaccc uucugaguag a                                               21

<210> SEQ ID NO 198
<211> LENGTH: 21
<212> TYPE: RNA
<213> ORGANISM: Homo sapiens

<400> SEQUENCE: 198
ugagcuaaau gugugcuggg a                                               21

<210> SEQ ID NO 199
<211> LENGTH: 22
<212> TYPE: RNA
<213> ORGANISM: Homo sapiens

<400> SEQUENCE: 199
uggauuucuu ugugaaucac ca                                              22

<210> SEQ ID NO 200
<211> LENGTH: 22
<212> TYPE: RNA
<213> ORGANISM: Homo sapiens

<400> SEQUENCE: 200
uagguaguuu ccuguuguug gg                                              22

<210> SEQ ID NO 201
<211> LENGTH: 22
<212> TYPE: RNA
<213> ORGANISM: Homo sapiens

<400> SEQUENCE: 201
ugucuuacuc ccucaggcac au                                              22

<210> SEQ ID NO 202
<211> LENGTH: 22
<212> TYPE: RNA
<213> ORGANISM: Homo sapiens

<400> SEQUENCE: 202
aaugcacccg ggcaaggauu cu                                              22

<210> SEQ ID NO 203
```

```
<211> LENGTH: 22
<212> TYPE: RNA
<213> ORGANISM: Homo sapiens

<400> SEQUENCE: 203
ugcggggcua gggcuaacag ca                                              22

<210> SEQ ID NO 204
<211> LENGTH: 22
<212> TYPE: RNA
<213> ORGANISM: Homo sapiens

<400> SEQUENCE: 204
aaugcaccug ggcaaggauu ca                                              22

<210> SEQ ID NO 205
<211> LENGTH: 23
<212> TYPE: RNA
<213> ORGANISM: Homo sapiens

<400> SEQUENCE: 205
cgcaucgccu agggcauugg ugu                                             23

<210> SEQ ID NO 206
<211> LENGTH: 21
<212> TYPE: RNA
<213> ORGANISM: Homo sapiens

<400> SEQUENCE: 206
uaccacaggg uagaaccacg g                                               21

<210> SEQ ID NO 207
<211> LENGTH: 21
<212> TYPE: RNA
<213> ORGANISM: Homo sapiens

<400> SEQUENCE: 207
aauggcgcca cuaggguugu g                                               21

<210> SEQ ID NO 208
<211> LENGTH: 23
<212> TYPE: RNA
<213> ORGANISM: Homo sapiens

<400> SEQUENCE: 208
uuaaugcuaa ucgugauagg ggu                                             23

<210> SEQ ID NO 209
<211> LENGTH: 23
<212> TYPE: RNA
<213> ORGANISM: Homo sapiens

<400> SEQUENCE: 209
ucucacacag aaaucgcacc cgu                                             23

<210> SEQ ID NO 210
<211> LENGTH: 23
<212> TYPE: RNA
<213> ORGANISM: Homo sapiens

<400> SEQUENCE: 210
uauucauuua uccccagccu aca                                             23
```

```
<210> SEQ ID NO 211
<211> LENGTH: 22
<212> TYPE: RNA
<213> ORGANISM: Homo sapiens

<400> SEQUENCE: 211
caccuugcgc uacucagguc ug                                              22

<210> SEQ ID NO 212
<211> LENGTH: 22
<212> TYPE: RNA
<213> ORGANISM: Homo sapiens

<400> SEQUENCE: 212
ucguaccgug aguaauaaug cg                                              22

<210> SEQ ID NO 213
<211> LENGTH: 22
<212> TYPE: RNA
<213> ORGANISM: Homo sapiens

<400> SEQUENCE: 213
augcaccugg gcaaggauuc ug                                              22

<210> SEQ ID NO 214
<211> LENGTH: 23
<212> TYPE: RNA
<213> ORGANISM: Homo sapiens

<400> SEQUENCE: 214
agcuacauug ucugcugggu uuc                                             23

<210> SEQ ID NO 215
<211> LENGTH: 22
<212> TYPE: RNA
<213> ORGANISM: Homo sapiens

<400> SEQUENCE: 215
ucaggcucag uccccucccg au                                              22

<210> SEQ ID NO 216
<211> LENGTH: 18
<212> TYPE: RNA
<213> ORGANISM: Homo sapiens

<400> SEQUENCE: 216
aauccuugcu accugggu                                                   18

<210> SEQ ID NO 217
<211> LENGTH: 23
<212> TYPE: RNA
<213> ORGANISM: Homo sapiens

<400> SEQUENCE: 217
agcucggucu gaggccccuc agu                                             23

<210> SEQ ID NO 218
<211> LENGTH: 22
<212> TYPE: RNA
<213> ORGANISM: Homo sapiens

<400> SEQUENCE: 218
ugagguagua guuuguacag uu                                              22
```

```
<210> SEQ ID NO 219
<211> LENGTH: 22
<212> TYPE: RNA
<213> ORGANISM: Homo sapiens

<400> SEQUENCE: 219
uucaccaccu ucuccaccca gc                                           22

<210> SEQ ID NO 220
<211> LENGTH: 23
<212> TYPE: RNA
<213> ORGANISM: Homo sapiens

<400> SEQUENCE: 220
ucccuguccu ccaggagcuc acg                                          23

<210> SEQ ID NO 221
<211> LENGTH: 23
<212> TYPE: RNA
<213> ORGANISM: Homo sapiens

<400> SEQUENCE: 221
uaauccuugc uaccugggug aga                                          23

<210> SEQ ID NO 222
<211> LENGTH: 22
<212> TYPE: RNA
<213> ORGANISM: Homo sapiens

<400> SEQUENCE: 222
uagcuuauca gacugauguu ga                                           22

<210> SEQ ID NO 223
<211> LENGTH: 18
<212> TYPE: RNA
<213> ORGANISM: Homo sapiens

<400> SEQUENCE: 223
cuaagaaguu gacugaag                                                18

<210> SEQ ID NO 224
<211> LENGTH: 22
<212> TYPE: RNA
<213> ORGANISM: Homo sapiens

<400> SEQUENCE: 224
ggauaucauc auauacugua ag                                           22

<210> SEQ ID NO 225
<211> LENGTH: 22
<212> TYPE: RNA
<213> ORGANISM: Homo sapiens

<400> SEQUENCE: 225
aaucugagaa ggcgcacaag gu                                           22

<210> SEQ ID NO 226
<211> LENGTH: 22
<212> TYPE: RNA
<213> ORGANISM: Homo sapiens

<400> SEQUENCE: 226
caggccauau ugugcugccu ca                                           22
```

<210> SEQ ID NO 227
<211> LENGTH: 19
<212> TYPE: RNA
<213> ORGANISM: Homo sapiens

<400> SEQUENCE: 227
aucccaccac ugccaccau                                                  19

<210> SEQ ID NO 228
<211> LENGTH: 22
<212> TYPE: RNA
<213> ORGANISM: Homo sapiens

<400> SEQUENCE: 228
ucugggcaac aaagugagac cu                                              22

<210> SEQ ID NO 229
<211> LENGTH: 21
<212> TYPE: RNA
<213> ORGANISM: Homo sapiens

<400> SEQUENCE: 229
gccccugggc cuauccuaga a                                               21

<210> SEQ ID NO 230
<211> LENGTH: 22
<212> TYPE: RNA
<213> ORGANISM: Homo sapiens

<400> SEQUENCE: 230
uguaacagca acuccaugug ga                                              22

<210> SEQ ID NO 231
<211> LENGTH: 22
<212> TYPE: RNA
<213> ORGANISM: Homo sapiens

<400> SEQUENCE: 231
ucucccaacc cuuguaccag ug                                              22

<210> SEQ ID NO 232
<211> LENGTH: 22
<212> TYPE: RNA
<213> ORGANISM: Homo sapiens

<400> SEQUENCE: 232
guggaguccu ggggaaugga ga                                              22

<210> SEQ ID NO 233
<211> LENGTH: 20
<212> TYPE: RNA
<213> ORGANISM: Homo sapiens

<400> SEQUENCE: 233
acugccccag gugcugcugg                                                 20

<210> SEQ ID NO 234
<211> LENGTH: 21
<212> TYPE: RNA
<213> ORGANISM: Homo sapiens

<400> SEQUENCE: 234

-continued agcuacaucu ggcuacuggg u                                                   21

<210> SEQ ID NO 235
<211> LENGTH: 22
<212> TYPE: RNA
<213> ORGANISM: Homo sapiens

<400> SEQUENCE: 235
auaauacaac cugcuaagug cu                                                  22

<210> SEQ ID NO 236
<211> LENGTH: 22
<212> TYPE: RNA
<213> ORGANISM: Homo sapiens

<400> SEQUENCE: 236
acugcugagc uagcacuucc cg                                                  22

<210> SEQ ID NO 237
<211> LENGTH: 22
<212> TYPE: RNA
<213> ORGANISM: Homo sapiens

<400> SEQUENCE: 237
cagcagcaau ucauguuuug aa                                                  22

<210> SEQ ID NO 238
<211> LENGTH: 20
<212> TYPE: RNA
<213> ORGANISM: Homo sapiens

<400> SEQUENCE: 238
uagaggaagc uguggagaga                                                     20

<210> SEQ ID NO 239
<211> LENGTH: 22
<212> TYPE: RNA
<213> ORGANISM: Homo sapiens

<400> SEQUENCE: 239
uuaugguuug ccugggacug ag                                                  22

<210> SEQ ID NO 240
<211> LENGTH: 23
<212> TYPE: RNA
<213> ORGANISM: Homo sapiens

<400> SEQUENCE: 240 uccccaggu gugauucuga uuu                                                  23

<210> SEQ ID NO 241
<211> LENGTH: 22
<212> TYPE: RNA
<213> ORGANISM: Homo sapiens

<400> SEQUENCE: 241
acuccagccc cacagccuca gc                                                  22

<210> SEQ ID NO 242
<211> LENGTH: 23
<212> TYPE: RNA
<213> ORGANISM: Homo sapiens

<400> SEQUENCE: 242

-continued

| | |
|---|---|
| ugaggggcag agagcgagac uuu | 23 |

<210> SEQ ID NO 243
<211> LENGTH: 21
<212> TYPE: RNA
<213> ORGANISM: Homo sapiens

<400> SEQUENCE: 243

| | |
|---|---|
| aucacauugc cagggauuac c | 21 |

<210> SEQ ID NO 244
<211> LENGTH: 22
<212> TYPE: RNA
<213> ORGANISM: Homo sapiens

<400> SEQUENCE: 244

| | |
|---|---|
| ugaccgauuu cuccuggugu uc | 22 |

<210> SEQ ID NO 245
<211> LENGTH: 22
<212> TYPE: RNA
<213> ORGANISM: Homo sapiens

<400> SEQUENCE: 245

| | |
|---|---|
| caaagaauuc uccuuuuggg cu | 22 |

<210> SEQ ID NO 246
<211> LENGTH: 18
<212> TYPE: RNA
<213> ORGANISM: Homo sapiens

<400> SEQUENCE: 246

| | |
|---|---|
| cagccccaca gccucaga | 18 |

<210> SEQ ID NO 247
<211> LENGTH: 22
<212> TYPE: RNA
<213> ORGANISM: Homo sapiens

<400> SEQUENCE: 247

| | |
|---|---|
| ugagguagua gguugugugg uu | 22 |

<210> SEQ ID NO 248
<211> LENGTH: 22
<212> TYPE: RNA
<213> ORGANISM: Homo sapiens

<400> SEQUENCE: 248

| | |
|---|---|
| ugagaccucu ggguucugag cu | 22 |

<210> SEQ ID NO 249
<211> LENGTH: 23
<212> TYPE: RNA
<213> ORGANISM: Homo sapiens

<400> SEQUENCE: 249

| | |
|---|---|
| uguaaacauc cuacacucuc agc | 23 |

<210> SEQ ID NO 250
<211> LENGTH: 23
<212> TYPE: RNA
<213> ORGANISM: Homo sapiens

```
<400> SEQUENCE: 250
uggaagacua gugauuuugu ugu                                          23

<210> SEQ ID NO 251
<211> LENGTH: 22
<212> TYPE: RNA
<213> ORGANISM: Homo sapiens

<400> SEQUENCE: 251
auauaauaca accugcuaag ug                                           22

<210> SEQ ID NO 252
<211> LENGTH: 22
<212> TYPE: RNA
<213> ORGANISM: Homo sapiens

<400> SEQUENCE: 252
aaaccguuac cauuacugag uu                                           22

<210> SEQ ID NO 253
<211> LENGTH: 22
<212> TYPE: RNA
<213> ORGANISM: Homo sapiens

<400> SEQUENCE: 253
cuauacaauc uauugccuuc cc                                           22

<210> SEQ ID NO 254
<211> LENGTH: 22
<212> TYPE: RNA
<213> ORGANISM: Homo sapiens

<400> SEQUENCE: 254
ggggcugggg ccggggccga gc                                           22

<210> SEQ ID NO 255
<211> LENGTH: 22
<212> TYPE: RNA
<213> ORGANISM: Homo sapiens

<400> SEQUENCE: 255
uuuucaacuc uaaugggaga ga                                           22

<210> SEQ ID NO 256
<211> LENGTH: 22
<212> TYPE: RNA
<213> ORGANISM: Homo sapiens

<400> SEQUENCE: 256
cuggcccucu cugcccuucc gu                                           22

<210> SEQ ID NO 257
<211> LENGTH: 22
<212> TYPE: RNA
<213> ORGANISM: Homo sapiens

<400> SEQUENCE: 257
ugaaacauac acgggaaacc uc                                           22

<210> SEQ ID NO 258
<211> LENGTH: 22
<212> TYPE: RNA
<213> ORGANISM: Homo sapiens
```

```
<400> SEQUENCE: 258
aggugcucca ggcuggcuca ca                                              22

<210> SEQ ID NO 259
<211> LENGTH: 22
<212> TYPE: RNA
<213> ORGANISM: Homo sapiens

<400> SEQUENCE: 259
cgucaacacu ugcugguuuc cu                                              22

<210> SEQ ID NO 260
<211> LENGTH: 23
<212> TYPE: RNA
<213> ORGANISM: Homo sapiens

<400> SEQUENCE: 260
cccaguguuc agacuaccug uuc                                             23

<210> SEQ ID NO 261
<211> LENGTH: 21
<212> TYPE: RNA
<213> ORGANISM: Homo sapiens

<400> SEQUENCE: 261
aggggugcua ucugugauug a                                               21

<210> SEQ ID NO 262
<211> LENGTH: 20
<212> TYPE: RNA
<213> ORGANISM: Homo sapiens

<400> SEQUENCE: 262
ccccagggcg acgcggcggg                                                 20

<210> SEQ ID NO 263
<211> LENGTH: 16
<212> TYPE: RNA
<213> ORGANISM: Homo sapiens

<400> SEQUENCE: 263
uucagcagga acagcu                                                     16

<210> SEQ ID NO 264
<211> LENGTH: 22
<212> TYPE: RNA
<213> ORGANISM: Homo sapiens

<400> SEQUENCE: 264
uuaucagaau cuccaggggu ac                                              22

<210> SEQ ID NO 265
<211> LENGTH: 22
<212> TYPE: RNA
<213> ORGANISM: Homo sapiens

<400> SEQUENCE: 265
agagguagua gguugcauag uu                                              22

<210> SEQ ID NO 266
<211> LENGTH: 22
<212> TYPE: RNA
```

-continued

<213> ORGANISM: Homo sapiens

<400> SEQUENCE: 266
cagcccggau cccagcccac uu                                    22

<210> SEQ ID NO 267
<211> LENGTH: 21
<212> TYPE: RNA
<213> ORGANISM: Homo sapiens

<400> SEQUENCE: 267
uggacugccc ugaucuggag a                                     21

<210> SEQ ID NO 268
<211> LENGTH: 17
<212> TYPE: RNA
<213> ORGANISM: Homo sapiens

<400> SEQUENCE: 268
cacugugggu acaugcu                                          17

<210> SEQ ID NO 269
<211> LENGTH: 22
<212> TYPE: RNA
<213> ORGANISM: Homo sapiens

<400> SEQUENCE: 269
ugagguagua gguuguaugg uu                                    22

<210> SEQ ID NO 270
<211> LENGTH: 17
<212> TYPE: RNA
<213> ORGANISM: Homo sapiens

<400> SEQUENCE: 270
acauugccag ggaguuu                                          17

<210> SEQ ID NO 271
<211> LENGTH: 21
<212> TYPE: RNA
<213> ORGANISM: Homo sapiens

<400> SEQUENCE: 271
augaccuaug aauugacaga c                                     21

<210> SEQ ID NO 272
<211> LENGTH: 23
<212> TYPE: RNA
<213> ORGANISM: Homo sapiens

<400> SEQUENCE: 272
uagcaccauu ugaaaucagu guu                                   23

<210> SEQ ID NO 273
<211> LENGTH: 22
<212> TYPE: RNA
<213> ORGANISM: Homo sapiens

<400> SEQUENCE: 273
cuauacaacc uacugccuuc cc                                    22

<210> SEQ ID NO 274
<211> LENGTH: 21

```
<212> TYPE: RNA
<213> ORGANISM: Homo sapiens

<400> SEQUENCE: 274
uacaguacug ugauaacuga a                                          21

<210> SEQ ID NO 275
<211> LENGTH: 23
<212> TYPE: RNA
<213> ORGANISM: Homo sapiens

<400> SEQUENCE: 275
uguaguguuu ccuacuuuau gga                                        23

<210> SEQ ID NO 276
<211> LENGTH: 17
<212> TYPE: RNA
<213> ORGANISM: Homo sapiens

<400> SEQUENCE: 276
ucccaccgcu gccaccc                                               17

<210> SEQ ID NO 277
<211> LENGTH: 22
<212> TYPE: RNA
<213> ORGANISM: Homo sapiens

<400> SEQUENCE: 277
cauugcacuu gucucggucu ga                                         22

<210> SEQ ID NO 278
<211> LENGTH: 22
<212> TYPE: RNA
<213> ORGANISM: Homo sapiens

<400> SEQUENCE: 278
cuccugacuc cagguccugu gu                                         22

<210> SEQ ID NO 279
<211> LENGTH: 22
<212> TYPE: RNA
<213> ORGANISM: Homo sapiens

<400> SEQUENCE: 279
aauugcacgg uauccaucug ua                                         22

<210> SEQ ID NO 280
<211> LENGTH: 21
<212> TYPE: RNA
<213> ORGANISM: Homo sapiens

<400> SEQUENCE: 280 aggggggaaag uucuauaguc c                                         21

<210> SEQ ID NO 281
<211> LENGTH: 17
<212> TYPE: RNA
<213> ORGANISM: Homo sapiens

<400> SEQUENCE: 281
ucucgcuggg gccucca                                               17

<210> SEQ ID NO 282
```

```
<211> LENGTH: 22
<212> TYPE: RNA
<213> ORGANISM: Homo sapiens

<400> SEQUENCE: 282
cacgcucaug cacacaccca ca                                              22

<210> SEQ ID NO 283
<211> LENGTH: 21
<212> TYPE: RNA
<213> ORGANISM: Homo sapiens

<400> SEQUENCE: 283
ucacagugaa ccggucucuu u                                               21

<210> SEQ ID NO 284
<211> LENGTH: 22
<212> TYPE: RNA
<213> ORGANISM: Homo sapiens

<400> SEQUENCE: 284
aacuggccua caaaguccca gu                                              22

<210> SEQ ID NO 285
<211> LENGTH: 24
<212> TYPE: RNA
<213> ORGANISM: Homo sapiens

<400> SEQUENCE: 285 ugggagcug aggcucuggg ggug                                             24

<210> SEQ ID NO 286
<211> LENGTH: 23
<212> TYPE: RNA
<213> ORGANISM: Homo sapiens

<400> SEQUENCE: 286
uaaagugcuu auagugcagg uag                                             23

<210> SEQ ID NO 287
<211> LENGTH: 21
<212> TYPE: RNA
<213> ORGANISM: Homo sapiens

<400> SEQUENCE: 287
cugaccuaug aauugacagc c                                               21

<210> SEQ ID NO 288
<211> LENGTH: 22
<212> TYPE: RNA
<213> ORGANISM: Homo sapiens

<400> SEQUENCE: 288
cagugcaaug uuaaaagggc au                                              22

<210> SEQ ID NO 289
<211> LENGTH: 22
<212> TYPE: RNA
<213> ORGANISM: Homo sapiens

<400> SEQUENCE: 289
ugagguagua gguuguauag uu                                              22
```

-continued

```
<210> SEQ ID NO 290
<211> LENGTH: 21
<212> TYPE: RNA
<213> ORGANISM: Homo sapiens

<400> SEQUENCE: 290
uucacagugg cuaaguuccg c                                              21

<210> SEQ ID NO 291
<211> LENGTH: 23
<212> TYPE: RNA
<213> ORGANISM: Homo sapiens

<400> SEQUENCE: 291
ugagcgccuc gacgacagag ccg                                            23

<210> SEQ ID NO 292
<211> LENGTH: 22
<212> TYPE: RNA
<213> ORGANISM: Homo sapiens

<400> SEQUENCE: 292
ucuucucugu uuuggccaug ug                                             22

<210> SEQ ID NO 293
<211> LENGTH: 22
<212> TYPE: RNA
<213> ORGANISM: Homo sapiens

<400> SEQUENCE: 293
aagcugccag uugaagaacu gu                                             22

<210> SEQ ID NO 294
<211> LENGTH: 22
<212> TYPE: RNA
<213> ORGANISM: Homo sapiens

<400> SEQUENCE: 294
uggggcggag cuuccggagg cc                                             22

<210> SEQ ID NO 295
<211> LENGTH: 22
<212> TYPE: RNA
<213> ORGANISM: Homo sapiens

<400> SEQUENCE: 295
gugagucucu aagaaaagag ga                                             22

<210> SEQ ID NO 296
<211> LENGTH: 22
<212> TYPE: RNA
<213> ORGANISM: Homo sapiens

<400> SEQUENCE: 296
gggagccagg aaguauugau gu                                             22

<210> SEQ ID NO 297
<211> LENGTH: 22
<212> TYPE: RNA
<213> ORGANISM: Homo sapiens

<400> SEQUENCE: 297
cgaaucauua uuugcugcuc ua                                             22
```

```
<210> SEQ ID NO 298
<211> LENGTH: 22
<212> TYPE: RNA
<213> ORGANISM: Homo sapiens

<400> SEQUENCE: 298
uagcagcacg uaaauauugg cg                                        22

<210> SEQ ID NO 299
<211> LENGTH: 22
<212> TYPE: RNA
<213> ORGANISM: Homo sapiens

<400> SEQUENCE: 299
aauccuuugu cccuggguga ga                                        22

<210> SEQ ID NO 300
<211> LENGTH: 21
<212> TYPE: RNA
<213> ORGANISM: Homo sapiens

<400> SEQUENCE: 300
uaaagugcug acagugcaga u                                         21

<210> SEQ ID NO 301
<211> LENGTH: 22
<212> TYPE: RNA
<213> ORGANISM: Homo sapiens

<400> SEQUENCE: 301
aacacaccua uucaaggauu ca                                        22

<210> SEQ ID NO 302
<211> LENGTH: 22
<212> TYPE: RNA
<213> ORGANISM: Homo sapiens

<400> SEQUENCE: 302
uucaaguaau ccaggauagg cu                                        22

<210> SEQ ID NO 303
<211> LENGTH: 22
<212> TYPE: RNA
<213> ORGANISM: Homo sapiens

<400> SEQUENCE: 303
uaacagucua cagccauggu cg                                        22

<210> SEQ ID NO 304
<211> LENGTH: 18
<212> TYPE: RNA
<213> ORGANISM: Homo sapiens

<400> SEQUENCE: 304
cgggcguggu ggugggg                                              18

<210> SEQ ID NO 305
<211> LENGTH: 23
<212> TYPE: RNA
<213> ORGANISM: Homo sapiens

<400> SEQUENCE: 305
aacauucauu gcugucggug ggu                                       23
```

```
<210> SEQ ID NO 306
<211> LENGTH: 22
<212> TYPE: RNA
<213> ORGANISM: Homo sapiens

<400> SEQUENCE: 306
aaggagcuca cagucuauug ag                                             22

<210> SEQ ID NO 307
<211> LENGTH: 21
<212> TYPE: RNA
<213> ORGANISM: Homo sapiens

<400> SEQUENCE: 307
uaacagucuc cagucacggc c                                              21

<210> SEQ ID NO 308
<211> LENGTH: 23
<212> TYPE: RNA
<213> ORGANISM: Homo sapiens

<400> SEQUENCE: 308
caaagugcuu acagugcagg uag                                            23

<210> SEQ ID NO 309
<211> LENGTH: 24
<212> TYPE: RNA
<213> ORGANISM: Homo sapiens

<400> SEQUENCE: 309
aauccuugga accuaggugu gagu                                           24

<210> SEQ ID NO 310
<211> LENGTH: 22
<212> TYPE: RNA
<213> ORGANISM: Homo sapiens

<400> SEQUENCE: 310
ugagguagua guuugugcug uu                                             22

<210> SEQ ID NO 311
<211> LENGTH: 18
<212> TYPE: RNA
<213> ORGANISM: Homo sapiens

<400> SEQUENCE: 311
gggucccggg gaggggggg                                                 18

<210> SEQ ID NO 312
<211> LENGTH: 17
<212> TYPE: RNA
<213> ORGANISM: Homo sapiens

<400> SEQUENCE: 312
ucccuguucg ggcgcca                                                   17

<210> SEQ ID NO 313
<211> LENGTH: 21
<212> TYPE: RNA
<213> ORGANISM: Homo sapiens

<400> SEQUENCE: 313
```

-continued auccuugcua ucugggugcu a                                            21

<210> SEQ ID NO 314
<211> LENGTH: 23
<212> TYPE: RNA
<213> ORGANISM: Homo sapiens

<400> SEQUENCE: 314
aacauucaac gcugucggug agu                                          23

<210> SEQ ID NO 315
<211> LENGTH: 24
<212> TYPE: RNA
<213> ORGANISM: Homo sapiens

<400> SEQUENCE: 315
cauagcccgg ucgcuggua c auga                                        24

<210> SEQ ID NO 316
<211> LENGTH: 23
<212> TYPE: RNA
<213> ORGANISM: Homo sapiens

<400> SEQUENCE: 316
uuagggagua gaagguggg gag                                           23

<210> SEQ ID NO 317
<211> LENGTH: 23
<212> TYPE: RNA
<213> ORGANISM: Homo sapiens

<400> SEQUENCE: 317 caaagucug uucgugcagg uag                                           23

<210> SEQ ID NO 318
<211> LENGTH: 17
<212> TYPE: RNA
<213> ORGANISM: Homo sapiens

<400> SEQUENCE: 318
cgcgccgggc ccgg guu                                                17

<210> SEQ ID NO 319
<211> LENGTH: 20
<212> TYPE: RNA
<213> ORGANISM: Homo sapiens

<400> SEQUENCE: 319
ucagggaguc aggggagggc                                              20

<210> SEQ ID NO 320
<211> LENGTH: 17
<212> TYPE: RNA
<213> ORGANISM: Homo sapiens

<400> SEQUENCE: 320
accccacucc uggua cc                                                17

<210> SEQ ID NO 321
<211> LENGTH: 22
<212> TYPE: RNA
<213> ORGANISM: Homo sapiens

<400> SEQUENCE: 321

```
cagugcaaug augaaagggc au                                    22

<210> SEQ ID NO 322
<211> LENGTH: 22
<212> TYPE: RNA
<213> ORGANISM: Homo sapiens

<400> SEQUENCE: 322
ugagguagua gauuguauag uu                                    22

<210> SEQ ID NO 323
<211> LENGTH: 17
<212> TYPE: RNA
<213> ORGANISM: Homo sapiens

<400> SEQUENCE: 323
uggagagaaa ggcagua                                          17

<210> SEQ ID NO 324
<211> LENGTH: 24
<212> TYPE: RNA
<213> ORGANISM: Homo sapiens

<400> SEQUENCE: 324
uuuggcaaug guagaacuca cacu                                  24

<210> SEQ ID NO 325
<211> LENGTH: 25
<212> TYPE: RNA
<213> ORGANISM: Homo sapiens

<400> SEQUENCE: 325
agggaucgcg ggcggguggc ggccu                                 25

<210> SEQ ID NO 326
<211> LENGTH: 21
<212> TYPE: RNA
<213> ORGANISM: Homo sapiens

<400> SEQUENCE: 326
uucacagugg cuaaguucug c                                     21

<210> SEQ ID NO 327
<211> LENGTH: 18
<212> TYPE: RNA
<213> ORGANISM: Homo sapiens

<400> SEQUENCE: 327
aaagcugggu ugagaagg                                         18

<210> SEQ ID NO 328
<211> LENGTH: 23
<212> TYPE: RNA
<213> ORGANISM: Homo sapiens

<400> SEQUENCE: 328
caaagugcuc auagugcagg uag                                   23

<210> SEQ ID NO 329
<211> LENGTH: 23
<212> TYPE: RNA
<213> ORGANISM: Homo sapiens
```

```
<400> SEQUENCE: 329
agcagcauug uacagggcua uga                                    23

<210> SEQ ID NO 330
<211> LENGTH: 22
<212> TYPE: RNA
<213> ORGANISM: Homo sapiens

<400> SEQUENCE: 330
ucagugcacu acagaacuuu gu                                     22

<210> SEQ ID NO 331
<211> LENGTH: 22
<212> TYPE: RNA
<213> ORGANISM: Homo sapiens

<400> SEQUENCE: 331
ucagugcauc acagaacuuu gu                                     22

<210> SEQ ID NO 332
<211> LENGTH: 18
<212> TYPE: RNA
<213> ORGANISM: Homo sapiens

<400> SEQUENCE: 332
cggggcggca ggggccuc                                          18

<210> SEQ ID NO 333
<211> LENGTH: 20
<212> TYPE: RNA
<213> ORGANISM: Homo sapiens

<400> SEQUENCE: 333
aaaagcuggg uugagagggu                                        20

<210> SEQ ID NO 334
<211> LENGTH: 18
<212> TYPE: RNA
<213> ORGANISM: Homo sapiens

<400> SEQUENCE: 334
aucccaccuc ugccacca                                          18

<210> SEQ ID NO 335
<211> LENGTH: 22
<212> TYPE: RNA
<213> ORGANISM: Homo sapiens

<400> SEQUENCE: 335
aaaagcuggg uugagagggc aa                                     22

<210> SEQ ID NO 336
<211> LENGTH: 23
<212> TYPE: RNA
<213> ORGANISM: Homo sapiens

<400> SEQUENCE: 336
uagugcaaua uugcuuauag ggu                                    23

<210> SEQ ID NO 337
<211> LENGTH: 23
<212> TYPE: RNA
<213> ORGANISM: Homo sapiens
```

-continued

<400> SEQUENCE: 337
ugaggauaug gcagggaagg gga                                             23

<210> SEQ ID NO 338
<211> LENGTH: 22
<212> TYPE: RNA
<213> ORGANISM: Homo sapiens

<400> SEQUENCE: 338
uagcaccauc ugaaaucggu ua                                              22

<210> SEQ ID NO 339
<211> LENGTH: 22
<212> TYPE: RNA
<213> ORGANISM: Homo sapiens

<400> SEQUENCE: 339
uauggcacug guagaauuca cu                                              22

<210> SEQ ID NO 340
<211> LENGTH: 22
<212> TYPE: RNA
<213> ORGANISM: Homo sapiens

<400> SEQUENCE: 340
ugagguagua aguuguauug uu                                              22

<210> SEQ ID NO 341
<211> LENGTH: 21
<212> TYPE: RNA
<213> ORGANISM: Homo sapiens

<400> SEQUENCE: 341
agggcccccc cucaauccug u                                               21

<210> SEQ ID NO 342
<211> LENGTH: 22
<212> TYPE: RNA
<213> ORGANISM: Homo sapiens

<400> SEQUENCE: 342
caugccuuga guguaggacc gu                                              22

<210> SEQ ID NO 343
<211> LENGTH: 19
<212> TYPE: RNA
<213> ORGANISM: Homo sapiens

<400> SEQUENCE: 343
ggggccuggc ggugggcgg                                                  19

<210> SEQ ID NO 344
<211> LENGTH: 21
<212> TYPE: RNA
<213> ORGANISM: Homo sapiens

<400> SEQUENCE: 344
uagcagcaca gaaauauugg c                                               21

<210> SEQ ID NO 345
<211> LENGTH: 23
<212> TYPE: RNA

<213> ORGANISM: Homo sapiens

<400> SEQUENCE: 345
caacggaauc ccaaaagcag cug    23

<210> SEQ ID NO 346
<211> LENGTH: 22
<212> TYPE: RNA
<213> ORGANISM: Homo sapiens

<400> SEQUENCE: 346
gagcuuauuc auaaaagugc ag    22

<210> SEQ ID NO 347
<211> LENGTH: 20
<212> TYPE: RNA
<213> ORGANISM: Homo sapiens

<400> SEQUENCE: 347
ccucugggcc cuuccuccag    20

<210> SEQ ID NO 348
<211> LENGTH: 21
<212> TYPE: RNA
<213> ORGANISM: Homo sapiens

<400> SEQUENCE: 348
gugccagcug cagugggga g    21

<210> SEQ ID NO 349
<211> LENGTH: 23
<212> TYPE: RNA
<213> ORGANISM: Homo sapiens

<400> SEQUENCE: 349
aaugacacga ucacucccgu uga    23

<210> SEQ ID NO 350
<211> LENGTH: 22
<212> TYPE: RNA
<213> ORGANISM: Homo sapiens

<400> SEQUENCE: 350
uccuguacug agcugccccg ag    22

<210> SEQ ID NO 351
<211> LENGTH: 22
<212> TYPE: RNA
<213> ORGANISM: Homo sapiens

<400> SEQUENCE: 351
ugucaguuug ucaaauaccc ca    22

<210> SEQ ID NO 352
<211> LENGTH: 19
<212> TYPE: RNA
<213> ORGANISM: Homo sapiens

<400> SEQUENCE: 352
aaaagcuggg uugagagga    19

<210> SEQ ID NO 353
<211> LENGTH: 22

<212> TYPE: RNA
<213> ORGANISM: Homo sapiens

<400> SEQUENCE: 353
uguaaacauc cuacacucag cu                                          22

<210> SEQ ID NO 354
<211> LENGTH: 22
<212> TYPE: RNA
<213> ORGANISM: Homo sapiens

<400> SEQUENCE: 354
ccaauauuac ugugcugcuu ua                                          22

<210> SEQ ID NO 355
<211> LENGTH: 19
<212> TYPE: RNA
<213> ORGANISM: Homo sapiens

<400> SEQUENCE: 355
gagccaguug gacaggagc                                              19

<210> SEQ ID NO 356
<211> LENGTH: 22
<212> TYPE: RNA
<213> ORGANISM: Homo sapiens

<400> SEQUENCE: 356
cuuucagucg gauguuuaca gc                                          22

<210> SEQ ID NO 357
<211> LENGTH: 23
<212> TYPE: RNA
<213> ORGANISM: Homo sapiens

<400> SEQUENCE: 357
uaaggugcau cuagugcaga uag                                         23

<210> SEQ ID NO 358
<211> LENGTH: 22
<212> TYPE: RNA
<213> ORGANISM: Homo sapiens

<400> SEQUENCE: 358
uaguaccagu accuuguguu ca                                          22

<210> SEQ ID NO 359
<211> LENGTH: 23
<212> TYPE: RNA
<213> ORGANISM: Homo sapiens

<400> SEQUENCE: 359
cagugcaaua guauugucaa agc                                         23

<210> SEQ ID NO 360
<211> LENGTH: 22
<212> TYPE: RNA
<213> ORGANISM: Homo sapiens

<400> SEQUENCE: 360
uggagagaaa ggcaguuccu ga                                          22

<210> SEQ ID NO 361

```
<211> LENGTH: 17
<212> TYPE: RNA
<213> ORGANISM: Homo sapiens

<400> SEQUENCE: 361 guggggaga ggcuguc                                                  17

<210> SEQ ID NO 362
<211> LENGTH: 23
<212> TYPE: RNA
<213> ORGANISM: Homo sapiens

<400> SEQUENCE: 362
agcagcauug uacagggcua uca                                          23

<210> SEQ ID NO 363
<211> LENGTH: 22
<212> TYPE: RNA
<213> ORGANISM: Homo sapiens

<400> SEQUENCE: 363
guucucccaa cguaagccca gc                                           22

<210> SEQ ID NO 364
<211> LENGTH: 18
<212> TYPE: RNA
<213> ORGANISM: Homo sapiens

<400> SEQUENCE: 364
agcaggugcg gggcggcg                                                18

<210> SEQ ID NO 365
<211> LENGTH: 22
<212> TYPE: RNA
<213> ORGANISM: Homo sapiens

<400> SEQUENCE: 365
uacccauugc auaucggagu ug                                           22

<210> SEQ ID NO 366
<211> LENGTH: 21
<212> TYPE: RNA
<213> ORGANISM: Homo sapiens

<400> SEQUENCE: 366
aucacauugc cagggauuuc c                                            21

<210> SEQ ID NO 367
<211> LENGTH: 22
<212> TYPE: RNA
<213> ORGANISM: Homo sapiens

<400> SEQUENCE: 367
uagcaccauu ugaaaucggu ua                                           22

<210> SEQ ID NO 368
<211> LENGTH: 21
<212> TYPE: RNA
<213> ORGANISM: Homo sapiens

<400> SEQUENCE: 368
ucgaggagcu cacagucuag u                                            21
```

-continued

```
<210> SEQ ID NO 369
<211> LENGTH: 21
<212> TYPE: RNA
<213> ORGANISM: Homo sapiens

<400> SEQUENCE: 369
uucaaguaau ucaggauagg u                                              21

<210> SEQ ID NO 370
<211> LENGTH: 22
<212> TYPE: RNA
<213> ORGANISM: Homo sapiens

<400> SEQUENCE: 370
aaaagcuggg uugagagggc ga                                             22

<210> SEQ ID NO 371
<211> LENGTH: 23
<212> TYPE: RNA
<213> ORGANISM: Homo sapiens

<400> SEQUENCE: 371
agcuucuuua cagugcugcc uug                                            23

<210> SEQ ID NO 372
<211> LENGTH: 21
<212> TYPE: RNA
<213> ORGANISM: Homo sapiens

<400> SEQUENCE: 372
aaggcagggc ccccgcuccc c                                              21

<210> SEQ ID NO 373
<211> LENGTH: 21
<212> TYPE: RNA
<213> ORGANISM: Homo sapiens

<400> SEQUENCE: 373
uggguuuacg uugggagaac u                                              21

<210> SEQ ID NO 374
<211> LENGTH: 23
<212> TYPE: RNA
<213> ORGANISM: Homo sapiens

<400> SEQUENCE: 374
uaaggugcau cuagugcagu uag                                            23

<210> SEQ ID NO 375
<211> LENGTH: 22
<212> TYPE: RNA
<213> ORGANISM: Homo sapiens

<400> SEQUENCE: 375
gugaauuacc gaagggccau aa                                             22

<210> SEQ ID NO 376
<211> LENGTH: 18
<212> TYPE: RNA
<213> ORGANISM: Homo sapiens

<400> SEQUENCE: 376
gggcucacau caccccau                                                  18
```

```
<210> SEQ ID NO 377
<211> LENGTH: 22
<212> TYPE: RNA
<213> ORGANISM: Homo sapiens

<400> SEQUENCE: 377
aacccguaga uccgaucuug ug                                              22

<210> SEQ ID NO 378
<211> LENGTH: 22
<212> TYPE: RNA
<213> ORGANISM: Homo sapiens

<400> SEQUENCE: 378
uagcagcaca uaaugguuug ug                                              22

<210> SEQ ID NO 379
<211> LENGTH: 22
<212> TYPE: RNA
<213> ORGANISM: Homo sapiens

<400> SEQUENCE: 379
uuauaauaca accugauaag ug                                              22

<210> SEQ ID NO 380
<211> LENGTH: 22
<212> TYPE: RNA
<213> ORGANISM: Homo sapiens

<400> SEQUENCE: 380
cugugcgugu gacagcggcu ga                                              22

<210> SEQ ID NO 381
<211> LENGTH: 23
<212> TYPE: RNA
<213> ORGANISM: Homo sapiens

<400> SEQUENCE: 381
uuuggcacua gcacauuuuu gcu                                             23

<210> SEQ ID NO 382
<211> LENGTH: 22
<212> TYPE: RNA
<213> ORGANISM: Homo sapiens

<400> SEQUENCE: 382
uccagcauca gugauuuugu ug                                              22

<210> SEQ ID NO 383
<211> LENGTH: 17
<212> TYPE: RNA
<213> ORGANISM: Homo sapiens

<400> SEQUENCE: 383
ggcgggugcg gggugg                                                     17

<210> SEQ ID NO 384
<211> LENGTH: 22
<212> TYPE: RNA
<213> ORGANISM: Homo sapiens

<400> SEQUENCE: 384
uagcagcaca ucaugguuua ca                                              22
```

```
<210> SEQ ID NO 385
<211> LENGTH: 22
<212> TYPE: RNA
<213> ORGANISM: Homo sapiens

<400> SEQUENCE: 385
ucccugagac ccuaacuugu ga                                              22

<210> SEQ ID NO 386
<211> LENGTH: 18
<212> TYPE: RNA
<213> ORGANISM: Homo sapiens

<400> SEQUENCE: 386
gcuggugaca ugagaggc                                                   18

<210> SEQ ID NO 387
<211> LENGTH: 22
<212> TYPE: RNA
<213> ORGANISM: Homo sapiens

<400> SEQUENCE: 387
ugagaacuga auuccauagg cu                                              22
```

COMPLEX SETS OF MIRNAS AS NON-INVASIVE BIOMARKERS FOR DILATED CARDIOMYOPATHY

This application is a 35 U.S.C. 371 National Phase Entry Application of the International Application No. PCT/EP2012/060927, filed on 8 Jun. 2012, which claims priority to European Patent Application EP11169192.9, filed on 8 Jun. 2011, the disclosures of which are incorporated herein by reference in their entirety.

TECHNICAL FIELD OF THE INVENTION

The present invention relates to a method for diagnosing and/or prognosing of dilated cardiomyopathy (DCM) based on the determination of expression profiles of sets of miRNAs representative for dilated cardiomyopathy (DCM) compared to a reference. Furthermore, the present invention relates to sets of polynucleotides and/or primer pairs for detecting sets of miRNAs for diagnosing and/or prognosing of dilated cardiomyopathy (DCM) in a biological sample from a subject. Further, the present invention relates to means for diagnosing and/or prognosing of dilated cardiomyopathy (DCM) comprising said sets of primer pairs and/or polynucleotides. In addition, the present invention relates to a kit for diagnosing and/or prognosing of dilated cardiomyopathy (DCM) comprising means for determining expression profiles of sets of miRNAs representative for dilated cardiomyopathy (DCM) and at least one reference. Further, the present invention relates to use of polynucleotides and/or primer pairs for for diagnosing and/or prognosing of dilated cardiomyopathy (DCM) in a biological samples of a subject.

BACKGROUND OF THE INVENTION

Today, biomarkers play a key role in early diagnosis, risk stratification, and therapeutic management of various diseases. While progress in biomarker research has accelerated over the last 5 years, the clinical translation of disease biomarkers as endpoints in disease management and as the foundation for diagnostic products still poses a challenge.

MicroRNAs (miRNAs) are a new class of biomarkers. They represent a group of small noncoding RNAs that regulate gene expression at the posttranslational level by degrading or blocking translation of messenger RNA (mRNA) targets. MiRNAs are important players when it comes to regulate cellular functions and in several diseases, including cancer.

So far, miRNAs have been extensively studied in tissue material. It has been found that miRNAs are expressed in a highly tissue-specific manner. Disease-specific expression of miRNAs have been reported in many human cancers employing primarily tissue material as the miRNA source. In this context miRNAs expression profiles were found to be useful in identifying the tissue of origin for cancers of unknown primary origin.

Since recently it is known that miRNAs are not only present in tissues but also in other body fluid samples, including human blood. Nevertheless, the mechanism why miRNAs are found in body fluids, especially in blood, or their function in these body fluids is not understood yet.

Various miRNA biomarkers found in tissue material have been proposed to be correlated with certain diseases, e.g. cancer. However, there is still a need for novel miRNAs as biomarkers for the detection and/or prediction of these and other types of diseases. Especially desirable are non-invasive biomarkers, that allow for quick, easy and cost-effective diagnosis/prognosis which cause only minimal stress for the patient eliminating the need for surgical intervention Particularly, the potential role of miRNAs as non-invasive biomarkers for the diagnosis and/or prognosis of dilated cardiomyopathy (DCM) has not been systematically evaluated yet. In addition, many of the miRNA biomarkers presently available for diagnosing and/or prognosing of diseases have shortcomings such as reduced sensitivity, not sufficient specificity or do not allow timely diagnosis or represent invasive biomarkers. Accordingly, there is still a need for novel and efficient miRNAs or sets of miRNAs as markers, effective methods and kits for the non-invasive diagnosis and/or prognosis of diseases such as dilated cardiomyopathy (DCM).

The inventors of the present invention assessed for the first time the expression of miRNAs on a whole-genome level in subjects with dilated cardiomyopathy (DCM) as non-invasive biomarkers from body fluids, preferably in blood. They surprisingly found that miRNAs are significantly dysregulated in blood of dilated cardiomyopathy (DCM) subjects in comparison to healthy controls and thus, miRNAs are appropriated non-invasive biomarkers for diagnosing and/or prognosing of dilated cardiomyopathy (DCM). This finding is surprising, since there is nearly no overlap of the miRNA biomarkers found in blood and the miRNA biomarkers found in tissue material representing the origin of the disease. The inventors of the present invention surprisingly found miRNA biomarkers in body fluids, especially in blood, that have not been found to be correlated to dilated cardiomyopathy (DCM) when tissues material was used for this kind of analysis. Therefore, the inventors of the invention identified for the first time miRNAs as non-invasive surrogate biomarkers for diagnosis and/or prognosis of dilated cardiomyopathy (DCM). The inventors of the present invention identified single miRNAs which predict dilated cardiomyopathy (DCM) with high specificity, sensitivity and accuracy. The inventors of the present invention also pursued a multiple biomarker strategy, thus implementing sets of miRNA biomarkers for diagnosing and/or prognosing of dilated cardiomyopathy (DCM) leading to added specificity, sensitivity, accuracy and predictive power, thereby circumventing the limitations of single biomarker. In detail, by using a machine learning algorithms, they identified unique sets of miRNAs (miRNA signatures) that allow for non-invasive diagnosis of dilated cardiomyopathy (DCM) with even higher power, indicating that sets of miRNAs (miRNA signatures) derived from a body fluid sample, such as blood from a subject (e.g. human) can be used as novel non-invasive biomarkers.

SUMMARY OF THE INVENTION

In a first aspect, the invention provides a method for diagnosing and/or prognosing of DCM comprising the steps of:
(i) determining an expression profile of a set comprising at least two miRNAs representative for DCM in a body fluid sample from a subject, and
(ii) comparing said expression profile to a reference, wherein the comparison of said expression profile to said reference allows for the diagnosis and/or prognosis of DCM, In a second aspect, the invention provides a set comprising polynucleotides for detecting a set comprising at least two miRNAs for diagnosing and/or prognosing of DCM in a body fluid sample from a subject.

In a third aspect, the invention provides a use of a set of polynucleotides according to the second aspect of the invention for diagnosing and/or prognosing DCM in a subject In a fourth aspect, the invention provides a set of primer pairs for determining the expression level of a set of miRNAs in a body fluid sample of a subject suffering or suspected of suffering from DCM.

In a fifth aspect, the invention provides a use of set of primer pairs according to the fourth aspect of the invention for diagnosing and/or prognosing DCM in a subject In a sixth aspect, the invention provides means for diagnosing and/or prognosing of DCM in a body fluid sample of a subject comprising:
  (i) a set of at least two polynucleotides according to the second aspect of the invention or
  (ii) a set of primer pairs according the fourth aspect of the invention.

In a seventh aspect, the invention provides a kit for diagnosing and/or prognosing of DCM comprising
  (i) means for determining an expression profile of a set comprising at least two miRNAs representative for DCM in a body fluid sample from a subject, and
  (ii) at least one reference.

In an eighth aspect, the invention provides a set of miRNAs in a body fluid sample isolated from a subject for diagnosing and/or prognosing of DCM.

In a ninth aspect, the invention provides a use of a set of miRNAs according to the eighth aspect of the invention for diagnosing and/or prognosing of DCM in a subject, In a tenth aspect, the present invention relates to a method for diagnosing and/or prognosing of DCM.

In an eleventh aspect, the invention relates to a method for diagnosing the severity of dilated cardiomyopathy In a twelfth aspect, the invention relates to a method for diagnosing dilated cardiomyopathy and diagnosing the severity of dilated cardiomyopathy In thirteenth aspect, the invention relates to a method for assessing the cardiac contractility.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (anti-strand), or passenger strand, is degraded as a RISC substrate.

Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The terms "microRNA*" or "miRNA*" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The "miRNA*s", also known as the "anti-guide strands" or "passenger strands", are mostly complementary to the "mature miRNAs" or "guide strands", but have usually single-stranded overhangs on each end. There are usually one or more mispairs and there are sometimes extra or missing bases causing single-stranded "bubbles". The miRNA*s are likely to act in a regulatory fashion as the miRNAs (see also above). In the context of the present invention, the terms "miRNA" and "miRNA*" are interchangeable used. The present invention encompasses (target) miRNAs which are dysregulated in biological samples such as blood or tissue of DCM patients in comparison to healthy controls. Said (target) miRNAs are preferably selected from the group consisting of SEQ ID NO: 1 to 387.

The term "miRBase" refers to a well established repository of validated miRNAs. The miRBase is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally spacer elements and/or elongation elements described below. The depiction of a single strand of a polynucleotide also defines the sequence of the complementary strand. Polynucleotides may be single stranded or double stranded, or may contain portions of both double stranded and single stranded sequences. The term "polynucleotide" means a polymer of deoxyribonucleotide or ribonucleotide bases and includes DNA and RNA molecules, both sense and anti-sense strands. In detail, the polynucleotide may be DNA, both cDNA and genomic DNA, RNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine Polynucleotides may be obtained by chemical synthesis methods or by recombinant methods.

In the context of the present invention, a polynucleotide as a single polynucleotide strand provides a probe (e.g. miRNA capture probe) that is capable of binding to, hybridizing with, or detecting a target of complementary sequence, such as a nucleotide sequence of a miRNA or miRNA*, through one or more types of chemical bonds, usually through complementary base pairing, usually through hydrogen bond formation. Polynucleotides in their function as probes may bind target sequences, such as nucleotide sequences of miRNAs or miRNAs*, lacking complete complementarity with the polynucleotide sequences depending upon the stringency of the hybridization condition. There may be any number of base pair mismatches which will interfere with hybridization between the target sequence, such as a nucleotide sequence of a miRNA or miRNA*, and the single stranded polynucleotide described herein. However, if the number of mutations is so great that no hybridization can occur under even the least stringent hybridization conditions, the sequences are no complementary sequences. The present invention encompasses polynucleotides in form of single polynucleotide strands as probes for binding to, hybridizing with or detecting complementary sequences of (target) miRNAs for diagnosing and/or prognosing of DCM. Said (target) miRNAs are preferably selected from the group consisting of SEQ ID NO: 1 to 387.

Because of the conservation of miRNAs among species, for example between humans and other mammals, e.g. animals such as mice, monkey or rat, the polynucleotide(s) of the invention may not only be suitable for detecting a miRNA(s) of a specific species, e.g. a human miRNA, but may also be suitable for detecting the respective miRNA orthologue(s) in another species, e.g. in another mammal, e.g. animal such as mouse or rat.

The term "antisense", as used herein, refers to nucleotide sequences which are complementary to a specific DNA or RNA sequence. The term "antisense strand" is used in reference to a nucleic acid strand that is complementary to the "sense" strand.

The term "label", as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which can be made detectable. A label may be incorporated into nucleic acids at any position, e.g. at the 3' or 5' end or internally. The polynucleotide for detecting a miRNA (polynucleotide probe) and/or the miRNA itself may be labeled. For detection purposes, the miRNA(s) or miRNA*(s) may be employed unlabeled, directly labeled, or indirectly labeled, such as with biotin to which a streptavidin complex may later bind.

The term "stringent hybridization conditions", as used herein, means conditions under which a first nucleotide sequence (e.g. polynucleotide in its function as a probe for detecting a miRNA or miRNA*) will hybridize to a second nucleotide sequence (e.g. target sequence such as nucleotide sequence of a miRNA or miRNA*), such as in a complex mixture of nucleotide sequences. Stringent conditions are sequence-dependent and will be different in different circumstances. Stringent conditions may be selected to be about 5 to 10° C. lower than the thermal melting point (Tm) for the specific sequence at a defined ionic strength, pH. The Tm may be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01 to 1.0 M sodium ion concentration (or other salts) at pH 7.0 to 8.3 and the temperature is at least about 20° C. for short probes (e.g. about 10-35 nucleotides) and up to 60° C. for long probes (e.g. greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "biological sample", as used in the context of the present invention, refers to any biological sample containing miRNA(s). Said biological sample may be a biological fluid, tissue, cell(s) or mixtures thereof. For example, biological samples encompassed by the present invention are body fluids, tissue (e.g. section or explant) samples, cell culture samples, cell colony samples, single cell samples, collection of single cell samples, blood samples (e.g. whole blood or a blood fraction such as serum or plasma), urine samples, or samples from other peripheral sources. Said biological samples may be mixed or pooled, e.g. a biological sample may be a mixture of blood and urine samples. A "biological sample" may be provided by removing cell(s), cell colonies, an explant, or a section from a subject suspected to be affected by DCM, but may also be provided by using a previously isolated sample. For example, a tissue sample may be removed from a subject suspected to be affected by DCMs by conventional biopsy techniques or a blood sample may be taken from a subject suspected to be affected by DCM by conventional blood collection techniques. The biological sample, e.g. tissue or blood sample, may be obtained from a subject suspected to be affected by DCM prior to initiation of the therapeutic treatment, during the therapeutic treatment and/or after the therapeutic treatment.

The term "body fluid sample", as used in the context of the present invention, refers to liquids originating from the body of a subject. Said body fluid samples include, but are not limited to, blood, urine, sputum, breast milk, cerebrospinal fluid, cerumen (earwax), endolymph, perilymph, gastric juice, mucus, peritoneal fluid, pleural fluid, saliva, sebum (skin oil), semen, sweat, tears, vaginal secretion, vomit including components or fractions thereof. Said body fluid samples may be mixed or pooled, e.g. a body fluid sample may be a mixture of blood and urine samples or blood and tissue material. A "body fluid sample" may be provided by removing a body liquid from a subject, but may also be provided by using previously isolated sample material.

Preferably, the body fluid sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" allows for a non-invasive diagnosis/and or prognosis of a subject.

The term "blood sample", as used in the context of the present invention, refers to a blood sample originating from a subject. The "blood sample" may be derived by removing blood from a subject by conventional blood collecting techniques, but may also be provided by using previously isolated and/or stored blood samples. For example a blood sample may be whole blood, plasma, serum, PBMC (peripheral blood mononuclear cells), blood cellular fractions including red blood cells (erythrocytes), white blood cells (leukocytes), platelets (thrombocytes), or blood collected in blood collection tubes (e.g. EDTA-, heparin-, citrate-, PAXgene-, Tempus-tubes) including components or fractions thereof. For example, a blood sample may be taken from a subject suspected to be affected or to be suspected to be affected by DCM, prior to initiation of a therapeutic treatment, during the therapeutic treatment and/or after the therapeutic treatment.

Preferably, the blood sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" allows for a non-invasive diagnosis/and or prognosis of a subject.

Preferably, when the blood sample is collected from the subject the RNA-fraction, especially the miRNA fraction, is guarded against degradation. For this purpose special collection tubes (e.g. PAXgene RNA tubes from Preanalytix, Tempus Blood RNA tubes from Applied Biosystems) or additives (e.g. RNAlater from Ambion, RNAsin from Promega) that stabilize the RNA fraction and/or the miRNA fraction are employed.

The biological sample, preferably the body fluid sample may be from a subject (e.g. human or mammal) that has been therapeutically treated or that has not been therapeutically treated. In one embodiment, the therapeutical treatment is monitored on the basis of the detection of the miRNA or set of miRNAs by the polynucleotide or set of polynucleotides of the invention. It is also preferred that total RNA or a subfraction thereof, isolated (e.g. extracted) from a biological sample of a subject (e.g. human or animal), is used for detecting the miRNA or set of miRNAs by the polynucleotide or set of polynucleotides or primer pairs of the invention.

The term "non-invasive", as used in the context of the present invention, refers to methods for obtaining a biological sample, particularly a body fluid sample, without the need for an invasive surgical intervention or invasive medical procedure. In the context of the present invention, a blood drawn represents a non-invasive procedure, therefore a blood-based test (utilizing blood or fractions thereof) is a non-invasive test. Other body fluid samples for non-invasive tests are e.g. urine, sputum, tears, mothers mild, cerumen, sweat, saliva, vaginal secretion, vomit, etc.

The term "minimal invasive", as used in the context of the present invention, refers to methods for obtaining a biological sample, particularly a body fluid sample, with a minimal need for an invasive surgical intervention or invasive medical procedure.

The term "biomarker", as used in the context of the present invention, represents a characteristic that can be objectively measured and evaluated as an indicator of normal and disease processes or pharmacological responses. A biomarker is a parameter that can be used to measure the onset or the progress of disease or the effects of treatment. The parameter can be chemical, physical or biological.

The term "surrogate biomarker", as used in the context of the present invention, represents biomarker intended to substitute for a clinical endpoint. It is a measure of a clinical condition or a measure of effect of a certain treatment that may correlate with the real clinical condition (e.g. healthy, diseased) but doesn't necessarily have a guaranteed relationship. An ideal surrogate biomarker is a laboratory substitute for a clinically meaningful result, and should lie directly in the causal pathway linking disease to outcome. Surrogate biomarkers are used when the primary endpoint is undesired (e.g. death). A commonly used example is cholesterol: while elevated cholesterol levels increase the likelihood for heart disease, the relationship is not linear—many people with normal cholesterol develop heart disease, and many with high cholesterol do not. "Death from heart disease" is the endpoint of interest, but "cholesterol" is the surrogate biomarker.

The term "diagnosis" as used in the context of the present invention refers to the process of determining a possible disease or disorder and therefore is a process attempting to define the (clinical) condition of a subject. The determination of the expression level of a set of miRNAs according to the present invention correlates with the (clinical) condition of a subject. Preferably, the diagnosis comprises (i) determining the occurrence/presence of DCM, (ii) monitoring the course of DCM, (iii) staging of DCM, (iv) measuring the response of a patient with DCM to therapeutic intervention, and/or (v) segmentation of a subject suffering from DCM.

The term "prognosis" as used in the context of the present invention refers to describing the likelihood of the outcome or course of a disease or a disorder. Preferably, the prognosis comprises (i) identifying of a subject who has a risk to develop DCM, (ii) predicting/estimating the occurrence, preferably the severity of occurrence of DCM, and/or (iii) predicting the response of a subject with DCM to therapeutic intervention.

The term "(clinical) condition" (biological state or health state), as used herein, means a status of a subject that can be described by physical, mental or social criteria. It includes so-called "healthy" and "diseased" conditions. For the definition of "healthy" and "diseased" conditions it is referred to the international classification of diseases (ICD) of the WHO. When one condition is compared according to a preferred embodiment of the method of the present invention, it is understood that said condition is DCM or a specific form of DCM. When two or more conditions are compared according to another preferred embodiment of the method of the present invention, it is understood that this is possible for all conditions that can be defined and is not limited to a comparison of a diseased versus healthy comparison and extends to multiway comparison, under the proviso that at least one condition is DCMs, preferably a specific form of DCM.

The term "miRNA expression profile" as used in the context of the present invention, represents the determination of the miRNA expression level or a measure that correlates with the miRNA expression level in a biological sample. The miRNA expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX) and the like, that allow the analysis of differential miRNA expression levels between samples of a subject (e.g. diseased) and a control subject (e.g. healthy, reference sample). The sample material measure by the aforementioned means may be total RNA, labeled total RNA, amplified total RNA, cDNA, labeled cDNA, amplified cDNA, miRNA, labeled miRNA, amplified miRNA or any derivatives that may be generated from the aforementioned RNA/DNA species. By determining the miRNA expression profile, each miRNA is represented by a numerical value. The higher the value of an individual miRNA, the higher is the expression level of said miRNA, or the lower the value of an individual miRNA, the lower is the expression level of said miRNA.

The "miRNA expression profile", as used herein, represents the expression level/expression data of a single miRNA or a collection of expression levels of at least two miRNAs, preferably of least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more, or up to all known miRNAs.

The term "differential expression" of miRNAs as used herein, means qualitative and/or quantitative differences in the temporal and/or local miRNA expression patterns, e.g. within and/or among biological samples, body fluid samples, cells, or within blood. Thus, a differentially expressed miRNA may qualitatively have its expression altered, including an activation or inactivation in, for example, blood from a diseases subject versus blood from a healthy subject. The difference in miRNA expression may also be quantitative, e.g. in that expression is modulated, i.e. either up-regulated, resulting in an increased amount of miRNA, or down-regulated, resulting in a decreased amount of miRNA. The degree to which miRNA expression differs need only be large enough to be quantified via standard expression characterization techniques, e.g. by quantitative hybridization (e.g. to a microarray), amplification (PCR, RT-PCR, qRT-PCR, high-throughput RT-PCR), ELISA for quantitation, next generation sequencing (e.g. ABI SOLID, Illumina Genome Analyzer, Roche 454 GS FL), flow cytometry (e.g. LUMINEX, Firefly Bioworks) and the like.

Nucleic acid hybridization may be performed using a microarray/biochip or in situ hybridization. In situ hybridization is preferred for the analysis of a single miRNA or a set comprising a low number of miRNAs (e.g. a set of at least 2 to 50 miRNAs such as a set of 2, 5, 10, 20, 30, or 40 miRNAs). The microarray/biochip, however, allows the analysis of a single miRNA as well as a complex set of miRNAs (e.g. a all known miRNAs or subsets thereof).

For nucleic acid hybridization, for example, the polynucleotides (probes) according to the present invention with complementarity to the corresponding miRNAs to be detected are attached to a solid phase to generate a microarray/biochip (e.g. 387 polynucleotides (probes) which are complementary to the 387 miRNAs having SEQ ID NO: 1 to 387. Said microarray/biochip is then incubated with a biological sample containing miRNAs, isolated (e.g. extracted) from the body fluid sample such as blood sample from a subject such as a human or an animal, which may be labelled, e.g. fluorescently labelled, or unlabelled. Quantification of the expression level of the miRNAs may then be carried out e.g. by direct read out of a label or by additional manipulations, e.g. by use of a polymerase reaction (e.g. template directed primer extension, MPEA-Assay, RAKE-assay) or a ligation reaction to incorporate or add labels to the captured miRNAs.

Alternatively, the polynucleotides which are at least partially complementary (e.g. a set of chimeric polynucleotides with each a first stretch being complementary to a set of miRNA sequences and a second stretch complementary to capture probes bound to a solid surface (e.g. beads, Luminex beads)) to miRNAs having SEQ ID NO: 1 to 387. are contacted with the biological sample containing miRNAs (e.g a body fluid sample, preferably a blood sample) in solution to hybridize. Afterwards, the hybridized duplexes are pulled down to the surface (e.g a plurality of beads) and successfully captured miRNAs are quantitatively determined (e.g. FlexmiR-assay, FlexmiR v2 detection assays from Luminex, Firelex from Firefly Bioworks).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 50 miRNAs such as a set of 2, 5, 10, 20, 30, or 40 miRNAs), whereas high-throughput RT-PCR technologies (e.g. OpenArray from Applied Biosystems, SmartPCR from Wafergen, Biomark System from Fluidigm) are also able to measure large sets (e.g a set of 10, 20, 30, 50, 80, 100, 200 or more) to all known miRNAs in a high parallel fashion. RT-PCR is particularly suitable for detecting low abandoned miRNAs.

The aforesaid real time polymerase chain reaction (RT-PCR) may include the following steps:

(i) extracting the total RNA from a biological sample or body fluid sample such as a blood sample (e.g. whole blood, serum, or plasma) of a subjects such as human or animal, and obtaining cDNA samples by RNA reverse transcription (RT) reaction using universal or miRNA-specific primers; or collecting a body fluid sample such as urine or blood sample (e.g. whole blood, serum, or plasma) of a patient such as human or animal, and conducting reverse transcriptase reaction using universal or miRNA-specific primers (e.g. looped RT-primers) within the body fluid sample such as urine or blood sample (e.g. whole blood, serum, or plasma) being a buffer so as to prepare directly cDNA samples, (ii) designing miRNA-specific cDNA forward primers and providing universal reverse primers to amplify the cDNA via polymerase chain reaction (PCR), (iii) adding a fluorescent dye (e.g. SYBR Green) or a fluorescent probe (e.g. Taqman probe) probe to conduct PCR, and (iv) detecting the miRNA(s) level in the body fluid sample such as urine or blood sample (e.g. whole blood, serum, or plasma).

A variety of kits and protocols to determine an expression profile by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300. Alternative kits are available from Ambion, Roche, Qiagen, Invitrogen, SABiosciences, Exiqon etc.

The term "subject", as used in the context of the present invention, means a patient or individual or mammal suspected to be affected by DCM. The patient may be diagnosed to be affected by DCM, i.e. diseased, or may be diagnosed to be not affected by DCM, i.e. healthy. The subject may also be diagnosed to be affected by a specific form of DCM. The subject may further be diagnosed to develop DCM or a specific form of DCM as the inventors of the present invention surprisingly found that miRNAs representative for DCM are already present in the biological sample, e.g. blood sample, before DCM occurs or during the early stage of DCM. It should be noted that a subject that is diagnosed as being healthy, i.e. not suffering from DCM or from a specific form of DCM, may possibly suffer from another disease not tested/known. The subject may be any mammal, including both a human and another mammal, e.g. an animal such as a rabbit, mouse, rat, or monkey. Human subjects are particularly preferred. Therefore, the miRNA from a subject may be a human miRNA or a miRNA from another mammal, e.g. an animal miRNA such as a mouse, monkey or rat miRNA, or the miRNAs comprised in a set may be human miRNAs or miRNAs from another mammal, e.g. animal miRNAs such as mouse, monkey or rat miRNAs.

The term "control subject", as used in the context of the present invention, may refer to a subject known to be affected with DCM (positive control), i.e. diseased, or to a subject known to be not affected with DCM (negative control), i.e. healthy. It may also refer to a subject known to be effected by another disease/condition (see definition "(clinical) condition"). It should be noted that a control subject that is known to be healthy, i.e. not suffering from DCM, may possibly suffer from another disease not tested/known. The control subject may be any mammal, including both a human and another mammal, e.g. an animal such as a rabbit, mouse, rat, or monkey. Human "control subjects" are particularly preferred.

The term "set comprising at least two miRNAs representative for DCM", as used herein, refers to refers to at least two fixed defined miRNAs comprised in a set which are known to be differential between subjects (e.g. humans or other mammals such as animals) suffering from DCM (diseased state) and control subjects (e.g. humans or other mammals such as animals and are, thus, representative for DCM. Said "set comprising at least two miRNAs representative for DCM" are preferably selected from the group consisting of SEQ ID NO: 1 to 387, a fragment thereof, and a sequence having at least 80% sequence identity thereto.

The term "dilated cardiomyopathy or DCM", as used herein refers to a condition in which the heart becomes weakened and enlarged and cannot pump blood efficiently. The decreased heart function can affect the lungs, liver, and other body systems. DCM is one of the cardiomyo-pathies, a group of diseases that primarily affect the myocardium (the muscle of the heart). Different cardiomyopathies have different causes and affect the heart in different ways. In DCM a portion of the myocardium is dilated, often without any obvious cause. Left or right ventricular systolic pump function of the heart is impaired, leading to progressive cardiac enlargement and hypertrophy, a process called remodeling. Dilated cardiomyopathy is the most common form of non-ischemic cardiomyopathy. It occurs more frequently in men than in women, and is most common between the ages of 20 and 60 years. About one in three cases of congestive heart failure (CHF) is due to dilated cardiomyopathy. Dilated cardiomyopathy also occurs in children. Once symptoms appear, the condition may be tentatively diagnosed based on a physical examination and a patient's medical history. More often, though, further examination is needed to differentiate dilated cardiomyopathy from other causes of heart failure. Diagnosis requires elimination of other possible causes of heart failure and arrhythmias No single test confirms dilated cardiomyopathy. Therefore, there is a high need for improved tests for diagnosis of DCM and furthermore for assessing the severity of DCM, especially in the field of non-invasive test.

The term "cardiac contractility" represents the intrinsic ability of the heart/myocardium to contract. It is a measure of cardiac pump performance, the degree to which muscle fibers can shorten when activated by a stimulus independent of preload and afterload The term "LVEF (eft ventricular ejection fraction)" is the measurement of how much blood is being pumped out of the left ventricle of the heart (the main pumping chamber) with each contraction. Ejection fraction is usually expressed as a percentage. A normal heart pumps a little more than half the heart's blood volume with each beat. A normal LVEF ranges from 55-70%. A LVEF of 65, for example, means that 65% of the total amount of blood in the left ventricle is pumped out with each heartbeat. The LVEF may be lower when the heart muscle has become damaged due to a heart attack, heart muscle disease (cardiomyopathy), or other causes.

The inventors of the present invention surprisingly found that miRNAs are significantly dysregulated in body fluid samples such as blood of DCM subjects in comparison to a cohort of controls (healthy subjects) and thus, miRNAs are appropriated biomarkers for diagnosing and/or prognosing of DCM in a non-invasive fashion or minimal-invasive fashion. Furthermore, the sets of miRNAs of the present invention lead to high performance in diagnosing and/or prognosing of DCM, thus expose very high specificity, sensitivity and accuracy. They succeeded in determining the miRNAs that are differentially regulated in body fluid samples from patients having DCM compared to a cohort of controls (healthy subjects) (see experimental section for experimental details). Additionally, the inventors of the present invention performed hypothesis tests (e.g. t-test, limma-test) or other measurements (e.g. AUC, mutual information) on the expression level of the found miRNAs, in all controls (healthy subjects) and subjects suffering from DCM. These tests resulted in a significance value (p-value) for each miRNA. This p-value is a measure for the diagnostic power of each of these single miRNAs to discriminate, for example, between the two clinical conditions: controls (healthy subjects), i.e. not suffering from DCM, or diseased, i.e. suffering from DCM. Since a manifold of tests are carried out, one for each miRNA, the p-values may be too optimistic and, thus, over-estimate the actual discriminatory power. Hence, the p-values are corrected for multiple testing by the Benjamini Hochberg approach.

Furthermore, the inventors surprisingly found that the expression of a set of predetermined miRNA biomarkers is highly correlated with the cardiac contractility. Even more surprising, the inventors found that by measuring the expression of a set of predetermined miRNA biomarkers as well the diagnosis of DCM, as well the determination of the severity is possible and that this assessment may be performed by measuring the same miRNA biomarkers in a simultaneous fashion.

An overview of the miRNAs that are found to be significantly differentially regulated in biological samples of DCM and that performed best according to t-test, limma-test or AUC is provided in FIGS. 1 and/or 2 (Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with DCM, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment). The miRNAs, i.e. miRNAs according to SEQ ID NO: 1 to 387, are sorted in order of their t-test significance as described in more detail in the experimental section (see ttest_adjp=adjusted p-value calculated according to ttest). It should be noted that the lower the ttest_adjp value of a single miRNA, the higher is the diagnostic power of said miRNA for diagnosing and/or prognosing of DCM.

Usually the diagnostic power of a single miRNA biomarker is not sufficient to reach high accuracy, specificity and sensitivity for discrimination between healthy subjects (controls) and subjects suffering from DCM, hence no simple threshold method can be used for diagnosis and/or prognosis.

Therefore, the inventors of the present invention employed more than one miRNA biomarker, i.e. sets of miRNA biomarkers (signatures), to further increase and/or improve the performance for diagnosing and/or prognosing of subjects suffering from DCM. This leads to a significant increase in sensitivity, specificity and accuracy when compared to the prior art.

In order to be able to discriminate, for example, between two or more clinical conditions, e.g. healthy and suffering from DCM, for a defined set of miRNA biomarkers, the inventors of the present invention applied a machine learning approach (e.g. t-test, AUC, support vector machine, hierarchical clustering, or k-means) which leads to an algorithm that is trained by reference data (i.e. data of reference miRNA expression profiles from the two clinical conditions, e.g. healthy and suffering from DCM, for the defined set of miRNA markers) to discriminate between the two statistical classes (i.e. two clinical conditions, e.g. healthy or suffering from DCM).

The inventors of the present invention surprisingly found that this approach yields in miRNA sets (signatures) that provide high diagnostic accuracy, specificity and sensitivity in the determination of DCM in patients (see FIG. 3A or FIG. 3B). Said miRNA sets (signatures) comprise at least two miRNAs, wherein the nucleotide sequences of said miRNAs are preferably selected from the group consisting of SEQ ID NO: 1 to 387.

An exemplarily approach to arrive at miRNA sets/signatures that correlate with DCM is summarized below:

Step 1: Total RNA (or subfractions thereof) is extracted from the biological sample, e.g. a body fluid sample, preferably a blood sample (including plasma, serum, PBMC or other blood fractions), using suitable kits and/or purification methods.

Step 2: From the respective samples the quantity (expression level) of one miRNA or sets of at least two miRNAs, e.g. selected from the group consisting of SEQ ID NO: 1 to SEQ ID NO: 387, is measured using experimental techniques. These techniques include but are not restricted to array based approaches, amplification methods (PCR, RT-PCR, qPCR), sequencing, next generation sequencing, flow cytometry and/or mass spectroscopy.

Step 3: In order to gather information on the diagnostic/prognostic value and the redundancy of each of the single miRNA biomarkers, mathematical methods are applied. These methods include, but are not restricted to, basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3) is used to estimate for each miRNA biomarker the diagnostic content or value. Usually, however, this diagnostic value is too small to get a highly accurate diagnosis with accuracy rates, specificities and sensitivities beyond the 90% barrier.

The diagnostic content of the miRNAs suitable for diagnosing/prognosing DCM is exemplarily listed in FIGS. 1 and/or 2 (Experimental details: SEQ ID NO: sequence identification number, miRNA: identifier of the miRNA according to miRBase, median g1: median intensity obtained from microarray analysis for healthy controls, median g2: median intensity obtained from microarray analysis for subjects with DCM, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment). This Figures includes the miRNAs according to SEQ ID NO: 1 to 387.

Step 5: In order to increase the performance for diagnosing/prognosing of subjects suffering from DCM, more than one miRNA biomarker needs to be employed. Thus statistical learning/machine learning/bioinformatics/computational approaches are applied for set selection in order to select/define sets of miRNA biomarkers (e.g. comprising miRNAs SEQ ID NO: 1 to 387) that are tailored for the detection of DCM. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis/prognosis of DCM. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning (Step 6) an algorithm or mathematical function for diagnosing/prognosing DCM is obtained. This algorithm or mathematical function is applied to a miRNA expression profile of a subject to be diagnosed for DCM.

In a first aspect, the present invention relates to a method for diagnosing and/or prognosing of DCM comprising the steps of:
(i) determining an expression profile of a set comprising at least two miRNAs representative for DCM in a body fluid sample from a subject, and
(ii) comparing said expression profile to a reference, wherein the comparison of said expression profile to said reference allows for the diagnosis and/or prognosis of DCM, It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is from the group consisting of SEQ ID NO: 1 to 387.

More preferably, the set comprising at least two miRNAs is from the group consisting of SEQ ID NO: 1, 3, 6, 14, 24, 27, 30, 34.

It is preferred that the set comprising at least two miRNAs is selected from the set of miRNAs listed in FIG. 3A or FIG. 3B.

It is preferred that the set comprising at least two miRNAs comprises at least one set of miRNAs listed in FIG. 3A or FIG. 3B.

It is more preferred that the levels of at least 2 miRNAs having (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 27, fragments thereof, or sequences have at least 90% sequence identity thereto, (vi) SEQ ID NO: 1 and SEQ ID NO: 30, fragments thereof, or sequences have at least 90% sequence identity thereto, (vii) SEQ ID NO: 1 and SEQ ID NO: 34, fragments thereof, or sequences have at least 90% sequence identity thereto, (viii) SEQ ID NO: 3 and SEQ ID NO: 6, fragments thereof, or sequences have at least 90% sequence identity thereto, (ix) SEQ ID NO: 3 and SEQ ID NO: 14, fragments thereof, or sequences have at least 90% sequence identity thereto, (x) SEQ ID NO: 3 and SEQ ID NO: 24, fragments thereof, or sequences have at least 90% sequence identity thereto, (xi) SEQ ID NO: 3 and SEQ ID NO: 27, fragments thereof, or sequences have at least 90% sequence identity thereto, (xii) SEQ ID NO: 3 and SEQ ID NO: 30, fragments thereof, or sequences have at least 90% sequence identity thereto, (xiii) SEQ ID NO: 3 and SEQ ID NO: 34, fragments thereof, or sequences have at least 90% sequence identity thereto, (xiv) SEQ ID NO: 6 and SEQ ID NO: 14, fragments thereof, or sequences have at least 90% sequence identity thereto, (xv) SEQ ID NO: 6 and SEQ ID NO: 24, fragments thereof, or sequences have at least 90% sequence identity thereto, (xvi) SEQ ID NO: 6 and SEQ ID NO: 27, fragments thereof, or sequences have at least 90% sequence identity thereto, (xvii) SEQ ID NO: 6 and SEQ ID NO: 30, fragments thereof, or sequences have at least 90% sequence identity thereto, (xviii) SEQ ID NO: 6 and SEQ ID NO: 34, fragments thereof, or sequences have at least 90% sequence identity thereto, (xix) SEQ ID NO: 14 and SEQ ID NO: 24, fragments thereof, or sequences have at least 90% sequence identity thereto, (xx) SEQ ID NO: 14 and SEQ ID NO: 27, fragments thereof, or sequences have at least 90% sequence identity thereto, (xxi) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xxiii) SEQ ID NO: 24 and SEQ ID NO: 27, fragments thereof, or sequences have at least 90% sequence identity thereto, (xxiv) SEQ ID NO: 24 and SEQ ID NO: 30, fragments thereof, or sequences have at least 90% sequence identity thereto, (xxv) SEQ ID NO: 24 and SEQ ID NO: 34, fragments thereof, or sequences have at least 90% sequence identity thereto, (xxvi) SEQ ID NO: 27 and SEQ ID NO: 30, fragments thereof, or sequences have at least 90% sequence identity thereto, (xxvii) SEQ ID NO: 27 and SEQ ID NO: 34, fragments thereof, or sequences have at least 90% sequence identity thereto, (xxviii) SEQ ID NO: 30 and SEQ ID NO: 34, fragments thereof, or sequences have at least 90% sequence identity thereto are determined.

Thus, it is preferred that the method for diagnosing and/or prognosing of DCM comprises the steps of:
(i) determining an expression profile (expression profile data) of a set comprising, essentially consisting of, or consisting of at least two miRNAs representative for DCM in a blood sample from a subject (e.g. a human or another mammal such as an animal), and
(ii) comparing said expression profile (expression profile data) to a reference, wherein the comparison of said expression profile (expression profile data) to said reference allows for the diagnosis and/or prognosis of DCM.

Thus, for analysis of a body fluid sample (e.g. blood sample) in step (i) of the method of the present invention, an expression profile of a set comprising at least two miRNAs which are known to be differential between subjects (e.g. humans or other mammals such as animals) having or being suspected to have DCM or a special form of DCM (diseased state) and subjects (e.g. humans or other mammals such as animals) not having DCM or a special form of DCM (healthy/control state) and are, thus, representative for DCM, is determined, wherein the nucleotide sequences of said miRNAs are) preferably selected from the group consisting of SEQ ID NO: 1 to 387, a fragment thereof, and a sequence having at least 80% sequence identity thereto.

It is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 387 miRNAs, representative for DCM in a body fluid sample (e.g. a blood sample) from a subject (e.g. a human or another mammal such as an animal) is determined in the step (i) of the method of the present invention, wherein the nucleotide sequences of said miRNAs are selected from the group consisting of
(i) a nucleotide sequence according to SEQ ID NO: 1 to SEQ ID NO: 387,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

Additionally, it is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 387 miRNAs, representative for DCM in a body fluid sample (e.g. a blood sample) from a subject (e.g. a human or another mammal such as an animal) is determined in the step (i) of the method of the present invention, wherein the set comprising at least two miRNAs is selected from the group consisting of
(i) a set of miRNAs listed in FIG. 3A or FIG. 3B
(ii) a combination of at least 2 sets of miRNAs listed in FIG. 3A or FIG. 3B
(iii) nucleotide sequences that are fragments of the nucleotide sequence according to (i) or (ii), preferably, nucleotide sequences that are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequences according to (i) or (ii), and
(iv) nucleotide sequences that have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequences according to (i) or (ii) or nucleotide sequence fragments according to (iii).

It is particularly preferred that the nucleotide sequences as defined in (iv) have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequences of the nucleotides according to (i) or (ii) or nucleotide fragments according to (iii).

Furthermore, according to the present invention, a first diagnosis and/or prognosis of DCM can be performed employing, as disclosed, miRNA-detection in a body fluid sample, e.g. in blood, followed by a second diagnosis and/or prognosis that is based on other methods (e.g. other biomarkers and/or imaging methods).

Furthermore, according to the present invention, the set comprising at least two miRNAs for diagnosing and/or prognosing DCM in a body fluid sample, e.g. blood sample, from a patient, e.g. human or animal, may be established on one experimental platform (e.g. microarray/biochip), while for routine diagnosis/prognosis another experimental platform (e.g. qPCR) may be chosen.

Subsequent to the determination of an expression profile (of expression profile data) of a set comprising at least two miRNAs representative for DCM as defined above in a body fluid sample (e.g. blood sample) from a patient (e.g. human or animal) in step (i) of the method for diagnosing and/or prognosing of DCM of the present invention, said method further comprises the step (ii) of comparing said expression profile (expression profile data) to a reference, wherein the comparison of said expression profile (expression profile data) to said reference allows for the diagnosis and/or prognosis of DCM.

The subject (e.g. human or another mammal (e.g. animal)) to be diagnosed with the method of the present invention may suffer, may be suspected to suffer or may not suffer from DCM. The subject (e.g. human or another mammal (e.g. animal)) to be diagnosed with the method of the present invention may suffer from a specific type of DCM. It is also possible to determine, whether the subject (e.g. human or another mammal (e.g. animal) to be diagnosed will develop DCM as the inventors of the present invention surprisingly found that miRNAs representative for DCM are already present in the body fluid sample, e.g. blood sample, before DCM occurs or during the early stage of DCM.

The reference may be the reference (e.g. reference expression profile (data)) of a healthy condition (i.e. not DCM), may be the reference (e.g. reference expression profile (data)) of a diseased condition (i.e. DCM) or may be the reference (e.g. reference expression profiles (data)) of at least two conditions from which at least one condition is a diseased condition (i.e. DCM). For example, (i) one condition may be a healthy condition (i.e. not DCM) and one condition may be a diseased condition (i.e. DCM), or (ii) one condition may be a diseased condition (e.g. a specific form of DCM) and one condition may be another diseased condition (i.e. specific form of DCM, or other timepoint of treatment, other therapeutic treatment).

Further, the reference may be the reference expression profiles (data) of essentially the same, preferably the same, set of miRNAs of step (i), preferably in a body fluid sample originated from the same source (e.g. urine, or blood such as serum, plasma, or blood cells) as the body fluid sample from the subject (e.g. human or animal) to be tested, but obtained from subjects (e.g. human or animal) known to not suffer from DCM and from subjects (e.g. human or animal) known to suffer from DCM (e.g.DCM, e.g. DCM that has been therapeutically treated).

Preferably, both the reference expression profile and the expression profile of step (i) are determined in the same body fluid sample, e.g. urine, or blood sample including a whole blood, a blood serum sample, blood plasma sample or a blood cell sample (e.g. erythrocytes, leukocytes and/or thrombocytes). It is understood that the reference expression profile is not necessarily obtained from a single subject known to be affected by DCM or known to be not affected by DCM (e.g. healthy subject, such as healthy human or animal, or diseased subject, such as diseased human or animal) but may be an average reference expression profile of a plurality of subjects known to be affected by DCM or known to be not affected by DCM (e.g. healthy subjects, such as healthy humans or animals, or diseased subjects, such as diseased humans or animals), e.g. at least 2 to 200 subjects, more preferably at least 10 to 150 subjects, and most preferably at least 20 to 100 subjects, (e.g. healthy subject, such as healthy human or animal, or diseased subject, such as diseased human or animal). The expression profile and the reference expression profile may be obtained from a subject/patient of the same species (e.g. human or animal), or may be obtained from a subject/patient of a different species (e.g. human or animal). Preferably, the expression profile is obtained from a subject known to be affected by DCM or known to be not affected by DCM of the same species (e.g. human or animal), of the same gender (e.g. female or male) and/or of a similar age/phase of life (e.g. infant, young child, juvenile, adult) as the subject (e.g. human or animal) to be tested or diagnosed.

Thus, in a preferred embodiment of the method of the present invention, the reference is a reference expression profile (data) of at least one subject, preferably the reference is an average expression profile (data) of at least 2 to 200 subjects, more preferably of at least 10 to 150 subjects, and most preferably of at least 20 to 100 subjects, with one known clinical condition which is DCM or a specific form of DCM, or which is not DCM or a specific form of DCM (i.e. healthy/healthiness), wherein the reference expression profile is the profile of a set comprising at least two miRNAs that have nucleotide sequences that essentially correspond (are essentially identical), preferably that correspond (are identical), to the nucleotide sequences of the miRNAs of step (i). Preferably, the reference expression profile is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 387, a fragment thereof, and a sequence having at least 80% sequence identity thereto of step (i).

The comparison of the expression profile of the patient to be diagnosed (e.g. human or animal) to the (average) reference expression profile may then allow for diagnosing and/or prognosing of DCM or a specific form of DCM (step (ii)), either the subject/patient (e.g. human or animal) to be diagnosed is healthy, i.e. not suffering from DCM, or diseased, i.e. suffering from DCM or a specific form of DCM.

The comparison of the expression profile of the subject (e.g. human or animal) to be diagnosed to said reference expression profile(s) may then allow for the diagnosis and/or prognosis of DCM (step (ii)), either the subject (e.g. human or animal) to be diagnosed is healthy, i.e. not suffering from DCM, or the subject (e.g. human or animal) is diseased, i.e. suffering from DCM.

The comparison of the expression profile of the patient (e.g. human or animal) to be diagnosed to said reference expression profiles may then allow for the diagnosis/prognosis of a specific form of DCM (step (ii)), e.g. whether the patient to be diagnosed suffers from DCM.

In a particularly preferred embodiment of the method of the present invention, the reference is an algorithm or mathematical function. Preferably, the algorithm or mathematical function is obtained on the basis of reference expression profiles (data) of at least 2 to 200 subjects, more preferably of at least 10 to 150 subjects, and most preferably of at least 20 to 100 subjects, with two known clinical conditions from which one is DCM, wherein the reference expression profiles is the profile of a set comprising at least two miRNAs that have nucleotide sequences that essentially correspond (are essentially identical), preferably that correspond (are identical), to the nucleotide sequences of the miRNAs of step (i). Preferably, is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 387, a fragment thereof, and a sequence having at least 80% sequence identity thereto of step (i).

It is preferred that the algorithm or mathematical function is obtained using a machine learning approach.

Machine learning approaches may include but are not limited to supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

The inventors of the present invention surprisingly found that the application/use of a machine learning approach (e.g. t-test, AUC, support vector machine, hierarchical clustering, or k-means) leads to the obtainment of an algorithm or mathematical function that is trained by the reference expression profile(s) or reference expression profile data mentioned above (e.g. trained by the miRNA reference expression profile (data) of a diseased condition (i.e. DCM or a specific form of DCM), for example, obtained from subjects (e.g. humans or animals) known to suffer from DCM or from a specific form of DCM (i.e. being diseased) and/or a trained by the miRNA reference expression profile (data) of a healthy condition (i.e. not DCM or a specific form of DCM), for example, obtained from subjects (e.g. humans or animals) known to not suffer from DCM or from a specific form of DCM and that this allows a better (i) discrimination between the at least two (e.g. 2 or 3) clinical conditions (the at least two statistical classes, e.g. the two conditions healthy or suffering from DCM or the two clinical conditions suffering from a specific form of DCM or suffering from another specific form of DCM or at least three clinical conditions, e.g. the three clinical conditions healthy, suffering from a specific form of DCM or suffering from another specific form of DCM or (ii) decision whether the at least one clinical condition (the one condition healthy or suffering from DCM is present. In this way, the performance for diagnosing/prognosing of individuals suffering from DCM can be increased (see also experimental section for details).

Thus, in a preferred embodiment of the method of the present invention, the algorithm or mathematical function is obtained using a machine learning approach, wherein said algorithm or mathematical function is trained by a reference expression profile (data) of at least 2 to 200 subjects, more preferably of at least 10 to 150 subjects, and most preferably of at least 20 to 100 subjects with two known clinical condition for which one is DCM or a specific form of DCM, wherein the reference expression profile is the profile of a set comprising at least two miRNAs that have nucleotide sequences that essentially correspond (are essentially identical), preferably that correspond (are identical), to the nucleotide sequences of the miRNAs of step (i), preferably to decide whether the at least one clinical condition which is DCM or a specific form of DCM.

Further, for instance, the machine learning approach may be applied to the reference expression profiles (data) of a set comprising at least 2 miRNAs (e.g. 10 miRNAs such as miRNAs according to SEQ ID NO: 1 to 10) of at least one subject (e.g. human or animal) known to suffer from DCM and of at least one subject (e.g. human or animal) known to be healthy and may led to the obtainment of an algorithm or mathematical function. This algorithm or mathematical function may then be applied to a miRNA expression profile of the same at least 2 miRNAs as mentioned above (e.g. 10 miRNAs such as miRNAs according to SEQ ID NO: 1 to 10) of a subject (e.g. human or animal) to be diagnosed for DCM and, thus, may then allow to discriminate whether the subject (e.g. human or animal) tested is healthy, i.e. not suffering from DCM, or diseased, i.e. suffering from DCM.

Additionally the algorithm may be trained to discriminate between more than 2 (e.g. 3, 4, 5 or more) clinical conditions from which at least one is DCM.

Preferably, the reference and optionally the expression profile (data) of the miRNA(s) representative for DCM is (are) stored in a database, e.g. an internet database, a centralized, and/or a decentralized database. It is preferred that the reference, e.g. mathematical function or algorithm, is comprised in a computer program, e.g. saved on a data carrier.

The above mentioned method is for diagnosing DCM in a subject, e.g. a human or another mammal such as an animal. Preferably, the diagnosis comprises (i) determining the occurrence/presence of DCM, (ii) monitoring the course of DCM, (iii) staging of DCM, (iv) measuring the response of a patient with DCM to therapeutic intervention, and/or (v) segmentation of a subject suffering from DCM.

Further, the above mentioned method is for prognosis of DCM in a subject, a human or another mammal such as an animal. Preferably, the prognosis comprises (i) identifying of a subject who has a risk to develop DCM, (ii) predicting/estimating the occurrence, preferably the severity of occurrence of DCM, and/or (iii) predicting the response of a subject with DCM to therapeutic intervention.

Further, in a preferred embodiment of the method of the present invention, for determining an expression profile of the set comprising at least two miRNAs representative for DCM in a body fluid sample from a subject comprises a set of miRNAs listed in FIG. 3A or FIG. 3B.

For example, said set comprising 30 miRNAs representative for DCM in a body fluid sample from a subject comprises a set of miRNAs listed in FIG. 3A or FIG. 3B. Alternatively, said set comprising 29, 28, 27, 26, 25, 24, 23, 22, 21, 20, 19, 18, 17, 16, 15, 14, 13, 12, 11, 10, 9, 8, 7, 6, 5, 4 or 3 miRNAs comprises a set of miRNAs listed in FIG. 3A or FIG. 3B.

For example, said set comprising 30 miRNAs representative for DCM in a body fluid sample from a subject comprises a set of miRNAs listed in FIG. 3A or FIG. 3B. For example, said set comprising 25 miRNAs representative for DCM in a body fluid sample from a subject comprises a set of miRNAs listed in FIG. 3A or FIG. 3B. For example, said set comprising 20 miRNAs representative for DCM in a body fluid sample from a subject comprises a set of miRNAs listed in FIG. 3A or FIG. 3B. For example, said set comprising 15 miRNAs representative for DCM in a body fluid sample from a subject comprises a set of miRNAs listed in FIG. 3A or FIG. 3B. For example, said set comprising 10 miRNAs representative for DCM in a body fluid sample from a subject comprises a set of miRNAs listed in FIG. 3A or FIG. 3B. For example, said set comprising 5 miRNAs representative for DCM in a body fluid sample from a subject comprises a set of miRNAs listed in FIG. 3A or FIG. 3B.

Further, in another preferred embodiment of the method of the present invention, for determining an expression profile of the set comprising at least two miRNAs representative for DCM in a body fluid sample from a subject comprises combinations of sets of miRNAs listed in FIG. 3A or FIG. 3B.

For example, said set comprising 30 miRNAs representative for DCM in a body fluid sample from a subject comprises at least 2 sets of miRNAs listed in FIG. 3A or FIG. 3B. Alternatively, said set comprising 29, 28, 27, 26, 25, 24, 23, 22, 21, 20, 19, 18, 17, 16, 15, 14, 13, 12, 11, 10, 9, 8, 7, 6, 5 or 4 miRNAs comprises a least 2 sets of miRNAs listed in FIG. 3A or FIG. 3B.

For example, said set comprising 30 miRNAs representative for DCM in a body fluid sample from a subject comprises a least 2 sets of miRNAs listed in FIG. 3A or FIG. 3B. For example, said set comprising 25 miRNAs representative for DCM in a body fluid sample from a subject comprises a least 2 sets of miRNAs listed in FIG. 3A or FIG. 3B. For example, said set comprising 20 miRNAs representative for DCM in a body fluid sample from a subject comprises a least 2 sets of miRNAs listed in FIG. 3A or FIG. 3B. For example, said set comprising 15 miRNAs representative for DCM in a body fluid sample from a subject comprises a least 2 sets of miRNAs listed in FIG. 3A or FIG. 3B. For example, said set comprising 10 miRNAs representative for DCM in a body fluid sample from a subject comprises a least 2 sets of miRNAs listed in FIG. 3A or FIG. 3B. For example, said set comprising 5 miRNAs representative for DCM in a body fluid sample from a subject comprises a least 2 sets of miRNAs listed in FIG. 3A or FIG. 3B.

In a second aspect, the invention relates to a set comprising polynucleotides for detecting a set comprising at least two miRNAs for diagnosing and/or prognosing of DCM in a body fluid sample from a subject.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the nucleotide sequences of the set comprising at least two miRNAs for diagnosing and/or prognosing of DCM in a body fluid sample, e.g. blood sample, from a patient, e.g. human or animal, are selected from the group consisting of SEQ ID NO: 1 to 387.

More preferably, the nucleotide sequences of the set comprising at least two miRNAs are selected from the group consisting of SEQ ID NO: 1, 3, 6, 14, 24, 27, 30, 34.

It is preferred that the set comprising at least two miRNAs is selected from the sets of miRNAs listed in FIG. 3A or FIG. 3B. It is preferred that the nucleotide sequences of the set comprising at least two miRNAs is selected from the sets of miRNAs listed in FIG. 3A or FIG. 3B.

It is more preferred that nucleotide sequences of the set comprising at least 2 miRNAs are selected from the sets of miRNAs comprising (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 27, fragments thereof, or sequences have at least 90% sequence identity thereto, (vi) SEQ ID NO: 1 and SEQ ID NO: 30, fragments thereof, or sequences have at least 90% sequence identity thereto, (vii) SEQ ID NO: 1 and SEQ ID NO: 34, fragments thereof, or sequences have at least 90% sequence identity thereto, (viii) SEQ ID NO: 3 and SEQ ID NO: 6, fragments thereof, or sequences have at least 90% sequence identity thereto, (ix) SEQ ID NO: 3 and SEQ ID NO: 14, fragments thereof, or sequences have at least 90% sequence identity thereto, (x) SEQ ID NO: 3 and SEQ ID NO: 24, fragments thereof, or sequences have at least 90% sequence identity thereto, (xi) SEQ ID NO: 3 and SEQ ID NO: 27, fragments thereof, or sequences have at least 90% sequence identity thereto, (xii) SEQ ID NO: 3 and SEQ ID NO: 30, fragments thereof, or sequences have at least 90% sequence identity thereto, (xiii) SEQ ID NO: 3 and SEQ ID NO: 34, fragments thereof, or sequences have at least 90% sequence identity thereto, (xiv) SEQ ID NO: 6 and SEQ ID NO: 14, fragments thereof, or sequences have at least 90% sequence identity thereto, (xv) SEQ ID NO: 6 and SEQ ID NO: 24, fragments thereof, or sequences have at least 90% sequence identity thereto, (xvi) SEQ ID NO: 6 and SEQ ID NO: 27, fragments thereof, or sequences have at least 90% sequence identity thereto, (xvii) SEQ ID NO: 6 and SEQ ID NO: 30, fragments thereof, or sequences have at least 90% sequence identity thereto, (xviii) SEQ ID NO: 6 and SEQ ID NO: 34, fragments thereof, or sequences have at least 90% sequence identity thereto, (xix) SEQ ID NO: 14 and SEQ ID NO: 24, fragments thereof, or sequences have at least 90% sequence identity thereto, (xx) SEQ ID NO: 14 and SEQ ID NO: 27, fragments thereof, or sequences have at least 90% sequence identity thereto, (xxi) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xxiii) SEQ ID NO: 24 and SEQ ID NO: 27, fragments thereof, or sequences have at least 90% sequence identity thereto, (xxiv) SEQ ID NO: 24 and SEQ ID NO: 30, fragments thereof, or sequences have at least 90% sequence identity thereto, (xxv) SEQ ID NO: 24 and SEQ ID NO: 34, fragments thereof, or sequences have at least 90% sequence identity thereto, (xxvi) SEQ ID NO: 27 and SEQ ID NO: 30, fragments thereof, or sequences have at least 90% sequence identity thereto, (xxvii) SEQ ID NO: 27 and SEQ ID NO: 34, fragments thereof, or sequences have at least 90% sequence identity thereto, (xxviii) SEQ ID NO: 30 and SEQ ID NO: 34, fragments thereof, or sequences have at least 90% sequence identity thereto.

It is preferred that (i) the polynucleotides comprised in the set of the present invention are complementary to the miRNAs comprised in the set, wherein the nucleotide sequences of said miRNAs are preferably selected from the group consisting of SEQ ID NO: 1 to 387, (ii) the polynucleotides comprised in the set are fragments of the polynucleotides comprised in the set according to (i), preferably the polynucleotides comprised in the set are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotides comprised in the set according to (i), or (iii) the polynucleotides comprised in the set have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequences of the polynucleotides comprised in the set according to (i) or polynucleotide fragments comprised in the set according to (ii).

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 387 miRNAs and wherein the nucleotide sequences of said miRNAs are selected from the group consisting of SEQ ID NO: 1 to 387.

It is preferred that the polynucleotides of the present invention are for detecting a set comprising, essentially consisting of, or consisting of at least 2 miRNAs, wherein the set comprising, miRNAs is selected from the set listed in FIG. 3A or FIG. 3B.

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 387 miRNAs and wherein the set of miRNAs comprises at least one of the sets listed in FIG. 3A or FIG. 3B.

For the body fluid sample (e.g. blood sample) analysis, it may be required that a set of polynucleotides (probes) capable of detecting a fixed defined set of miRNAs are attached to a solid support, bead, substrate, surface, platform, or matrix, e.g. biochip, which may be used for body fluid sample (e.g. blood sample) analysis. For example, if the fixed defined set of miRNAs for diagnosing DCM comprises or consists of 20 miRNAs, polynucleotides capable of detecting these 20 miRNAs are attached to a solid support, substrate, surface, platform or matrix, e.g. biochip, in order to perform the diagnostic sample analysis.

Alternatively, it may be required that a set of chimeric polynucleotides (probes) capable of detecting a fixed defined set of miRNAs it contacted in solution with a sample containing miRNAs derived from a body fluid sample. The chimeric polynucleotide may comprise of a first sequence stretch that is complementary to a miRNA and a second sequence stretch that allows to pull down the chimeric polynucleotide-miRNA-duplexes to one or more solid supports (e.g. a set of beads for determining the set of miRNAs). For example, a set of 20 chimeric polynucleotides capable of detecting 20 miRNAs are contacted with sample containing miRNAs derived from a body fluid sample in order to form duplexes that can be pulled down to 20 different species of beads and detected theron.

For example, the polynucleotides of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 miRNAs wherein the set of miRNAs comprises at least one of the set of miRNAs listed in FIG. 3A or FIG. 3B.

For example, the polynucleotides of the present invention are for detecting a set of 30 miRNAs wherein the set of miRNAs comprises at least one of the sets of miRNAs listed in FIG. 3A or FIG. 3B. For example, the polynucleotides of the present invention are for detecting a set of 25 miRNAs wherein the set of miRNAs comprises at least one of the sets of miRNAs listed in FIG. 3A or FIG. 3B. For example, the polynucleotides of the present invention are for detecting a set of 20 miRNAs wherein the set of miRNAs comprises at least one of the sets of miRNAs listed in FIG. 3A or FIG. 3B. For example, the polynucleotides of the present invention are for detecting a set of 15 miRNAs wherein the set of miRNAs comprises at least one of the sets of miRNAs listed in FIG. 3A or FIG. 3B. For example, the polynucleotides of the present invention are for detecting a set of 10 miRNAs wherein the set of miRNAs comprises at least one of the sets of miRNAs listed in FIG. 3A or FIG. 3B. For example, the polynucleotides of the present invention are for detecting a set of 8 miRNAs wherein the set of miRNAs comprises at least one of the sets of miRNAs listed in FIG. 3A or FIG. 3B. For example, the polynucleotides of the present invention are for detecting a set of 5 miRNAs wherein the set of miRNAs comprises at least one of the sets of miRNAs listed in FIG. 3A or FIG. 3B.

In a third aspect, the invention relates to the use of set of polynucleotides according to the second aspect of the invention for diagnosing and/or prognosing DCM in a subject In a fourth aspect, the invention relates to a set of at least two primer pairs for determining the expression level of a set of miRNAs in a body fluid sample of a subject suffering or suspected of suffering from DCM.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, that the set comprising at least two miRNAs for diagnosing and/or prognosing of DCM in a body fluid sample, e.g. blood sample, from a subject, e.g. patient, human or animal, are selected from the group consisting of SEQ ID NO: 1 to 387.

More preferably, the set of at least two primer pairs is selected for determining miRNAs selected from the group consisting of SEQ ID NO: 1, 3, 6, 14, 24, 27, 30, 34.

It is preferred that the set comprising at least two miRNAs is selected from the sets of miRNAs listed in FIG. 3A or FIG. 3B.

It is preferred that the set of at least two primer pairs for determining the expression level of a set of miRNAs in a body fluid sample of a subject suffering or suspected of suffering from DCM are primer pairs that are specific for at least one miRNA selected from the group consisting of SEQD ID 1 to 387.

It is preferred that the set of at least two primer pairs for determining the expression level of a set of miRNAs in a body fluid sample of a subject suffering or suspected of suffering from DCM are primer pairs that are specific for at least one set of miRNAs listed in FIG. 3A or FIG. 3B.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 387 miRNAs and wherein the nucleotide sequences of said miRNAs are selected from the group consisting of SEQ ID NO: 1 to 387.

It is preferred that the set of at least two primer pairs of the present invention are for detecting a set comprising, essentially consisting of, or consisting of at least 2 miRNAs, wherein the set comprising, miRNAs is selected from the set listed in FIG. 3A or FIG. 3B.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 387 miRNAs and wherein the set of miRNAs comprises at least one of the sets listed in FIG. 3A or FIG. 3B.

For example, the set of at least two primer pairs of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 miRNAs wherein the set of miRNAs comprises at least one of the set of miRNAs listed in FIG. 3.

For example, the set of primer pairs of the present invention are for detecting a set of 30 miRNAs wherein the set of miRNAs comprises at least one of the sets of miRNAs listed in FIG. 3A or FIG. 3B. For example, the set of primer pairs of the present invention are for detecting a set of 25 miRNAs wherein the set of miRNAs comprises at least one of the sets of miRNAs listed in FIG. 3A or FIG. 3B. For example, the set of primer pairs of the present invention are for detecting a set of 20 miRNAs wherein the set of miRNAs comprises at least one of the sets of miRNAs listed in FIG. 3A or FIG. 3B. For example, the set of primer pairs of the present invention are for detecting a set of 15 miRNAs wherein the set of miRNAs comprises at least one of the sets of miRNAs listed in FIG. 3A or FIG. 3B. For example, the set of primer pairs of the present invention are for detecting a set of 8 miRNAs wherein the set of miRNAs comprises at least one of the sets of miRNAs listed in FIG. 3A or FIG. 3B. For example, the set of primer pairs of the present invention are for detecting a set of 10 miRNAs wherein the set of miRNAs comprises at least one of the sets of miRNAs listed in FIG. 3A or FIG. 3B.

Preferably, the said primer pairs may be used for amplifying cDNA transcripts of the set of miRNAs selected from the group consisting of SEQ ID 1 to 387. Furthermore, the said primer pairs may be used for amplifying cDNA transcripts of the set of miRNAs listed in FIG. 3A or FIG. 3B It is understood that the primer pairs for detecting a set of miRNAs may consist of specific and or non-specific primers. Additionally, the set of primer pairs may be complemented by other substances or reagents (e.g. buffers, enzymes, dye, labelled probes) known to the skilled in the art for conducting real time polymerase chain reaction (RT-PCR)

In a fifth aspect, the invention relates to the use of a set of primer pairs according to the fourth aspect of the invention for diagnosing and/or prognosing DCM in a subject In a sixth aspect, the invention relates to means for diagnosing and/or prognosing of DCM in a body fluid sample of a subject Preferably, the invention relates to means for diagnosing and/or prognosing of DCM in a body fluid sample of a subject comprising
(i) a set of at least two polynucleotides according to the second aspect of the invention or
(ii) a set of at least two primer pairs according the fourth aspect of the invention.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, that the set of at least two polynucleotides or the set of at least 2 primer pairs are for detecting a set comprising at least two miRNAs for diagnosing and/or prognosing of DCM in a body fluid sample, e.g. blood sample, from a subject, e.g. patient, human or animal, wherein the set of miRNAs is selected from the group consisting of SEQ ID NO: 1 to 387.

More preferably, the set of at least two polynucleotides or the set of at least 2 primer pairs are for detecting a set comprising for determining miRNAs selected from the group consisting of SEQ ID NO: 1, 3, 6, 14, 24, 27, 30, 34.

It is preferred that the set of at least two polynucleotides or the set of at least 2 primer pairs are for detecting a set comprising at least two miRNAs for diagnosing and/or prognosing of DCM in a body fluid sample, e.g. blood sample, from a subject, e.g. patient, human or animal, wherein the set of miRNAs is selected from the sets of miRNAs listed in FIG. 3A or FIG. 3B.

It is preferred that the set of at least two primer pairs for determining the expression level of a set of miRNAs in a body fluid sample of a subject suffering or suspected of suffering from DCM are primer pairs that are specific for at least two miRNAs selected from the group consisting of SEQD ID 1 to 387.

It is preferred that the set of at least two primer pairs for determining the expression level of a set of miRNAs in a body fluid sample of a subject suffering or suspected of suffering from DCM are primer pairs that are specific for at least one set of miRNAs listed in FIG. 3A or FIG. 3B.

It is preferred that the subject is a mammal including both a human and another mammal, e.g. an animal such as a mouse, a rat, a rabbit, or a monkey. It is particularly preferred that the subject is a human.

The present invention provides means for diagnosing and/or prognosing of DCM comprising a set comprising, essentially consisting of, or consisting of at least two polynucleotides (probes) according to the second aspect of the present invention, e.g. a polynucleotide for detecting a set comprising, essentially consisting of, or consisting of at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 387 or more polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or 387 miRNAs or all known miRNAs, wherein the nucleotide sequence of said miRNAs are preferably selected from the group consisting of SEQ ID NO: 1 to 387, a fragment thereof, and a sequence having at least 80% sequence identity thereto.

The means for diagnosing and/or prognosing of DCM comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 387 polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 387 miRNAs, wherein the nucleotide sequence said miRNAs are preferably selected from the group consisting of SEQ ID NO: 1 to 387, a fragment thereof, and a sequence having at least 80% sequence identity thereto. Preferably, the above mentioned polynucleotide(s) is (are) attached or immobilized to the solid support, substrate, surface, platform or matrix. It is possible to include appropriate controls for non-specific hybridization on the solid support, substrate, surface, platform or matrix.

Additionally, the means for diagnosing and/or prognosing of DCM comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 387 polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 387 miRNAs, wherein the set of miRNAs comprises at least one set of miRNAs listed in FIG. 3A or FIG. 3B. Preferably, the above mentioned polynucleotides are attached or immobilized to the solid support, substrate, surface, platform or matrix. It is possible to include appropriate controls for non-specific hybridization on the solid support, substrate, surface, platform or matrix.

It is particularly preferred that said means for diagnosing and/or prognosing of DCM comprise, essentially consists of, or consists of a microarray/biochip comprising at least two polynucleotides according to the second aspect of the present invention.

It is also preferred that said means for diagnosing and/or prognosing of DCM comprise, essentially consists of, or consists of a set of beads comprising a at least two polynucleotides according to the second aspect of the present invention. It is especially preferred that the beads are employed within a flow cytometer setup for diagnosing and/or prognosing of DCM, e.g. in a LUMINEX system.

Additionally, the present invention provides means for diagnosing and/or prognosing of DCM comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 387 or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 387 miRNAs or all known miRNAs, wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto.

Also, the present invention provides means for diagnosing and/or prognosing of DCM comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 387 or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 387 miRNAs or all known miRNAs, wherein the set of miRNAs comprises at least one set of miRNAs listed in FIG. 3A or FIG. 3B.

In a seventh aspect, the invention relates to a kit for diagnosing and/or prognosing of DCM in a subject.

Preferably, the invention relates to a kit for diagnosing and/or prognosing of DCM comprising
  (i) means for determining an expression profile of a set comprising at least two miRNAs representative for DCM in a body fluid sample from a subject, and
  (ii) at least one reference.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

The present invention provides a kit for diagnosing and/or prognosing of DCM comprising (i) means for determining an expression profile of a a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 387 or more polynucleotides or alternatively a set of at least 2 or up to 387 or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 387 miRNAs or all known miRNAs, representative for DCM in a biological sample (e.g. a body fluid samples or a blood sample) from a subject (e.g. human or animal), wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto; and (ii) at least one reference.

The present invention provides a kit for diagnosing and/or prognosing of DCM comprising (i) means for determining an expression profile of a a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 387 or more polynucleotides or alternatively a set of at least 2 or up to 387 or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 387 miRNAs or all known miRNAs, representative for DCM in a biological sample (e.g. a body fluid samples or a blood sample) from a subject (e.g. human or animal), wherein the set of miRNAs comprises at least one of the set of miRNAs listed in FIG. 3A or FIG. 3B.

(ii) at least one reference.

Said means may comprise a set comprising, essentially consisting of, or consisting of at least two polynucleotides according to the second aspect of the present invention, a set of at least 2 primer pairs according to the fourth aspect of the invention; means according to the sixth aspect of the present invention; primers suitable to perform reverse transcriptase reaction and/or real time polymerase chain reaction such as quantitative polymerase chain reaction; and/or means for conducting next generation sequencing.

It is particularly preferred that said kit comprises (ia) a set comprising, essentially consisting of, or consisting of at least two polynucleotides according to the second aspect of the present invention, or a set of primer pairs according to the fourth aspect of the invention and (ib) optionally at least one of the means selected from the group consisting of: at least one biological sample, for example, tissue sample or body fluid sample, e.g. a blood sample, e.g. whole blood, serum, plasma, or blood cells, of a subject (e.g. human or animal), at least one sample of total RNA extracted from said biological sample, for example, body fluid sample, tissue sample or blood sample, e.g. whole blood, serum, plasma, or blood cells, of a patient (e.g. human or animal), and means to extract RNA from a body fluid sample, e.g. blood sample, e.g. for determining an expression profile of a set comprising, essentially consisting of, or consisting of at least two miRNAs representative for DCM in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto.

It is more particularly preferred that said kit comprises (ia) a solid support, substrate, surface, platform or matrix (e.g a microarray of a set of beads) according to the third aspect of the present invention comprising a polynucleotide or a set comprising, essentially consisting of, or consisting of at least two polynucleotides according of the first aspect of the present invention, and (ib) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, from a patient (e.g. human or animal), means to extract total RNA (or fractions thereof, e.g. miRNA) from a body fluid sample (e.g. blood sample), means for input/injection of a body fluid sample (e.g. blood sample), positive controls for the hybridization experiment, means for holding the solid support, substrate, platform or matrix comprising the polynucleotide(s) (probe(s)), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least two miRNAs representative for DCM in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto.

Preferably, the above mentioned set comprising, essentially consisting of, or consisting of at least two polynucleotides are attached or immobilized to the solid support, substrate, surface, platform or matrix, e.g. to a microarray or to a set of beads.

Preferably, the above mentioned set comprising, essentially consisting of, or consisting of at least two polynucleotides is (are) attached or immobilized to microarray/biochip.

It is particularly preferred that said kit comprises (ia) a miRNA-specific primer for reverse transcription of miRNA in miRNA-specific cDNA for a single miRNA (e.g. human miRNA or miRNA from another mammal such as an animal (e.g. mouse or rat miRNA)) or at least two miRNA-specific primers for reverse transcription of miRNAs in miRNA-specific cDNAs for at least 2 miRNAs (e.g. human miRNAs or miRNAs from another mammal such as an animal (e.g. mouse or rat miRNAs)), preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or 387 miRNAs (e.g. human miRNAs or miRNAs from another mammal such as an animal (e.g. mouse or rat miRNAs)), comprised in a set of miRNAs, wherein the nucleotide sequence of said miRNA or the nucleotide sequences of said miRNAs is (are) preferably selected from the group consisting of SEQ ID NO: 1 387, and (ib) preferably, a primer set comprising a forward primer which is specific for the cDNA obtained from the miRNA and an universal reverse primer for amplifying the cDNA obtained from the miRNA via real time polymerase chain reaction (RT-PCR) such as real time quantitative polymerase chain reaction (RT qPCR) for the single cDNA obtained from the miRNA or at least two primer sets comprising a forward primer which is specific for the single cDNA obtained from the miRNA and an universal reverse primer for amplifying the cDNA obtained from the miRNA via real time polymerase chain reaction (RT-PCR) such as real time quantitative polymerase chain reaction (RT qPCR) for at least 2, preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 387 cDNAs obtained from the miRNAs comprised in the set of miRNAs, wherein preferably said cDNA is complementary to the nucleotide sequence of the miRNA or said cDNAs are complementary to the nucleotide sequences of the miRNAs selected from the group consisting of SEQ ID NO: 1 to 387, and (ic) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, form a patient (e.g. human or animal), means to extract total RNA (or fractions thereof, e.g. miRNA) from a body fluid sample (e.g. blood sample), additional means to carry out the reverse transcriptase reaction (miRNA in cDNA) (e.g. reverse transcriptase (RT) enzyme, puffers, dNTPs, RNAse inhibitor), additional means to carry out real time polymerase chain reaction (RT-PCR) such as real time quantitative PCR (RT qPCR) (e.g. enzymes, puffers, water), means for labelling (e.g. fluorescent label and/or quencher), positive controls for reverse transcriptase reaction and real time PCR, and means for analysing the real time polymerase chain reaction (RT-PCR) result, e.g. for determining an expression profile of a miRNA or a set comprising, essentially consisting of, or consisting of at least 2, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or 387 miRNAs representative for DCM in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto.

The primer as defined above may also be an oligo-dT primer, e.g. if the miRNA comprises a polyA tail (e.g. as a result of a miRNA elongation, for example, subsequent to RNA extraction) or a miRNA specific looped RT primer (Please amend/adapted if required).

It is also preferred that said kit comprises means for conducting next generation sequencing in order to determine an expression profile of a (single) miRNA or a set comprising, essentially consisting of, or consisting of at least 2 miRNAs representative for DCM in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto. Preferably, said kit further comprises means selected from the group consisting of: at least one body fluid sample, for example, tissue or blood sample, e.g. blood serum, blood plasma, or blood cells from a patient (e.g. human or animal), at least one sample of total RNA (or fractions thereof, e.g. miRNA) extracted from the body fluid sample (e.g. tissue or blood sample) of a patient (e.g. human or animal), and means to extract total RNA (or fractions thereof, e.g. miRNA) from a body fluid sample (e.g. blood sample).

The above mentioned kits further comprise at least one reference (ii). A comparison to said reference may allow for the diagnosis and/or prognosis of DCM. Said reference may be the reference (e.g. reference expression profile (data)) of a healthy condition (i.e. not DCM or a specific form of DCM), may be the reference (e.g. reference expression profile (data)) of a diseased condition (i.e. DCM), or may be the reference (e.g. reference expression (data)) of at least two conditions from which at least one condition is a diseased condition (i.e. DCM).

It is preferred that said reference is a reference expression profile (data) of at least one subject (e.g. human or animal), preferably the reference is an average expression profile (data) of at least 2 to 200 subjects, more preferably at least 10 to 150 subjects, and most preferably at least 20 to 100 subjects, with one known clinical condition which is DCM or a specific form of DCM, or which is not DCM or not a specific form of DCM (i.e. healthy/healthiness), wherein the reference expression profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that said reference are (average) reference expression profiles (data) of at least two subjects, preferably of at least 2 to 200 subjects, more preferably of at least 10 to 150 subjects, and most preferably of at least 20 to 100 subjects, with at least two known clinical conditions, preferably at least 2 to 5, more preferably at least 2 to 4 (i.e. at least 2, 3, 4, or 5) known clinical conditions, from which at least one is DCM), wherein the reference expression profiles are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the reference is generated from expression profiles (data) obtained from 2 clinical conditions, which are DCM and healthy control.

Preferably, (i) the (average) reference expression profile (data), which is provided with the kit, is determined in the same type of body fluid sample (e.g. blood and/or urine sample) and/or obtained from (control) subject(s) of the same species, gender and/or of similar age/stage of life, or (ii) the (average) reference expression profiles (data), which are provided with the kit, are determined in the same type of body fluid sample (e.g. blood and/or urine sample) and/or are obtained from (control) subject(s) of the same species, gender and/or of similar age/stage of life.

Said reference, preferably said (average) reference expression profile(s) (data) may be comprised in an information leaflet (e.g. for comparing tested single reference miRNA biomarkers with the expression profile data of a patient to be diagnosed) or saved on a data carrier (e.g. for comparing tested sets of miRNA biomarkers with the expression profile data of a patient to be diagnosed). Said reference, preferably said (average) reference expression profile(s) (data) may also be comprised in a computer program which is saved on a data carrier. The kit may alternatively comprise an access code which allows the access to a database, e.g. an internet database, a centralized or a decentralized database, where said reference, preferably said (average) reference expression profile(s) (data) is (are) comprised.

It is particularly preferred that the reference is an algorithm or mathematical function.

Preferably the algorithm or mathematical function is obtained from a reference expression profile (data) of at least one subject, preferably the algorithm or mathematical function is obtained from an average reference expression profile (data) of at least 2 to 200 subjects, more preferably of at least 10 to 150 subjects, and most preferably of at least 20 to 100 subjects, i.e. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is DCM or a specific form of DCM, or which is not DCM or a specific form of DCM (i.e. healthy/healthiness), wherein the reference expression profile is the profile of a single miRNA that has a nucleotide sequence that essentially corresponds (is essentially identical), preferably that corresponds (is identical), to the nucleotide sequence of the miRNA which expression profile is determined by the means of (i), or is the profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that the algorithm or mathematical function is obtained from (average) reference expression profiles (data) of at least two subjects, preferably of at least 2 to 200 subjects, more preferably of at least 10 to 150 subjects, and most preferably of at least 20 to 100 subjects, i.e. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions, preferably at least 2 to 5, more preferably at least 2 to 4 (i.e. at least 2, 3, 4, or 5) known clinical conditions, from which at least one is DCM, wherein the reference expression profiles are the profiles of a single miRNA that has a nucleotide sequence that essentially corresponds (is essentially identical), preferably that corresponds (is identical), to the nucleotide sequence of the miRNA which expression profile is determined by the means of (i) or are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the algorithm or mathematical function is obtained using a machine learning approach (see second aspect of the present invention).

Preferably, the algorithm or mathematical function is saved on a data carrier comprised in the kit or the computer program, wherein the algorithm or mathematical function is comprised, is saved on a data carrier comprised in the kit. Said kit may alternatively comprise an access code which allows the access to an internet page, where the algorithm or mathematical function is saved or where the computer program, wherein the algorithm or mathematical function is comprised, can be downloaded.

Preferably, the algorithm or mathematical function is saved on a data carrier or the algorithm or mathematical function is comprised in a computer program which is saved on a data carrier. Said kit may alternatively comprise an access code which allows the access to a database or an internet page, where the algorithm or mathematical function is comprised, or where a computer program comprising the algorithm or mathematical function can be downloaded.

More than one reference may be comprised in the kit, e.g. 2, 3, 4, 5, or more references. For example, the kit may comprise reference data, preferably (average) reference expression profile(s) (data), which may be comprised in an information leaflet or saved on a data carrier. In addition, the kit may comprise more than one algorithm or mathematical function, e.g. two algorithms or mathematical functions, e.g. one trained to discriminate between a healthy condition and DCM and one trained to discriminate between specific forms of DCM, e.g. comprised in a computer program, preferably stored on a data carrier.

In an eighth aspect, the invention relates to a set of miRNAs isolated from a body fluid sample from a subject for diagnosing and/or prognosing of DCM, wherein the miRNAs are selected from the group consisting of SEQ ID 1 to 387.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

More preferably, the set of miRNAs is selected from the group consisting of SEQ ID NO: 1, 3, 6, 14, 24, 27, 30, 34.

It is preferred that the subject is a mammal including both a human and another mammal, e.g. an animal such as a mouse, a rat, a rabbit, or a monkey. It is particularly preferred that the subject is a human.

It is preferred that the predetermined set of miRNAs comprises miRNAs that are differentially regulated in blood samples from DCM patients as compared to healthy controls.

Preferably, the predetermined set comprising at least two miRNAs that are differentially regulated in blood samples from DCM patients as compared to healthy controls is selected from the set of miRNAs listed in FIG. 3A or FIG. 3B.

It is preferred that the predetermined set comprising at least two miRNAs that are differentially regulated in blood samples from DCM patients as compared to healthy controls comprises at least one set of miRNAs listed in FIG. 3A or FIG. 3B.

It is more preferred that set of miRNAs isolated comprising at least 2 miRNAs comprises (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 27, fragments thereof, or sequences have at least 90% sequence identity thereto, (vi) SEQ ID NO: 1 and SEQ ID NO: 30, fragments thereof, or sequences have at least 90% sequence identity thereto, (vii) SEQ ID NO: 1 and SEQ ID NO: 34, fragments thereof, or sequences have at least 90% sequence identity thereto, (viii) SEQ ID NO: 3 and SEQ ID NO: 6, fragments thereof, or sequences have at least 90% sequence identity thereto, (ix) SEQ ID NO: 3 and SEQ ID NO: 14, fragments thereof, or sequences have at least 90% sequence identity thereto, (x) SEQ ID NO: 3 and SEQ ID NO: 24, fragments thereof, or sequences have at least 90% sequence identity thereto, (xi) SEQ ID NO: 3 and SEQ ID NO: 27, fragments thereof, or sequences have at least 90% sequence identity thereto, (xii) SEQ ID NO: 3 and SEQ ID NO: 30, fragments thereof, or sequences have at least 90% sequence identity thereto, (xiii) SEQ ID NO: 3 and SEQ ID NO: 34, fragments thereof, or sequences have at least 90% sequence identity thereto, (xiv) SEQ ID NO: 6 and SEQ ID NO: 14, fragments thereof, or sequences have at least 90% sequence identity thereto, (xv) SEQ ID NO: 6 and SEQ ID NO: 24, fragments thereof, or sequences have at least 90% sequence identity thereto, (xvi) SEQ ID NO: 6 and SEQ ID NO: 27, fragments thereof, or sequences have at least 90% sequence identity thereto, (xvii) SEQ ID NO: 6 and SEQ ID NO: 30, fragments thereof, or sequences have at least 90% sequence identity thereto, (xviii) SEQ ID NO: 6 and SEQ ID NO: 34, fragments thereof, or sequences have at least 90% sequence identity thereto, (xix) SEQ ID NO: 14 and SEQ ID NO: 24, fragments thereof, or sequences have at least 90% sequence identity thereto, (xx) SEQ ID NO: 14 and SEQ ID NO: 27, fragments thereof, or sequences have at least 90% sequence identity thereto, (xxi) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xxiii) SEQ ID NO: 24 and SEQ ID NO: 27, fragments thereof, or sequences have at least 90% sequence identity thereto, (xxiv) SEQ ID NO: 24 and SEQ ID NO: 30, fragments thereof, or sequences have at least 90% sequence identity thereto, (xxv) SEQ ID NO: 24 and SEQ ID NO: 34, fragments thereof, or sequences have at least 90% sequence identity thereto, (xxvi) SEQ ID NO: 27 and SEQ ID NO: 30, fragments thereof, or sequences have at least 90% sequence identity thereto, (xxvii) SEQ ID NO: 27 and SEQ ID NO: 34, fragments thereof, or sequences have at least 90% sequence identity thereto, (xxviii) SEQ ID NO: 30 and SEQ ID NO: 34, fragments thereof, or sequences have at least 90% sequence identity thereto.

In a ninth aspect, the invention relates to the use of a set of miRNAs according to the eighth aspect of the invention for diagnosing and/or prognosing of DCM in a subject, In a tenth aspect, the present invention relates to a method for diagnosing and/or prognosing of DCM comprising the steps of:
(i) providing a set comprising at least two polynucleotides according to the second aspect of the present invention for detecting a set comprising at least two miRNAs representative for DCM in a body fluid sample (e.g. blood sample) from a patient (e.g. human or animal),
   wherein the nucleotide sequence of said miRNA or the nucleotide sequences of said miRNAs is (are) preferably selected from the group consisting of SEQ ID NO: 1 to 387, a fragment thereof, and a sequence having at least 80% sequence identity thereto,
(ii) using the polynucleotide(s) provided in (i) for determining an miRNA expression profile in a body fluid sample (e.g. blood sample) from a patient (e.g. human or animal) with an unknown clinical condition,
(iii) comparing said expression profile to a reference,
(iv) diagnosing or prognosing the clinical condition of the patient (e.g. human or animal) on the basis of said comparison.

The term "patient with an unknown clinical condition" refers to a patient (e.g. human or animal) which may suffer from DCM (i.e. diseased patient) or may not suffer from DCM (i.e. healthy patient). The patient (e.g. human or animal) to be diagnosed may further suffer from a specific type of DCM. It is also possible to determine, whether the patient (e.g. human or animal) to be diagnosed will develop the above mentioned disease as the inventors of the present invention surprisingly found that miRNAs representative for DCM are already present in the body fluid sample, e.g. blood sample, before DCM occurs or during the early stage of DCM. It should be noted that a patient that is diagnosed as being healthy, i.e. not suffering from DCM, may possibly suffer from another disease not tested/known.

In a eleventh aspect, the invention relates to a method for diagnosing the severity of dilated cardiomyopathy, comprising the steps of:
(i) determining an expression profile of a set comprising at least two miRNAs representative for dilated cardiomyopathy in a body fluid sample from a subject, and
(ii) comparing said expression profile to a reference, wherein the comparison of said expression profile to said reference allows for the diagnosis of the severity of dilated cardiomyopathy, It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is selected from the group consisting SEQ ID NO: 1, 3, 6, 14, 24, 27, 30, 34.

Preferably, the set comprising at least two miRNAs is selected from the set of miRNAs listed in FIG. 3B.

It is more preferred in the method for diagnosing the severity of dilated cardiomyopathy that the set comprising at least two miRNAs having (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 30, fragments thereof, or sequences have at least 90% sequence identity thereto, (vi) SEQ ID NO: 1 and SEQ ID NO: 34, fragments thereof, or sequences have at least 90% sequence identity thereto, (vii) SEQ ID NO: 3 and SEQ ID NO: 6, fragments thereof, or sequences have at least 90% sequence identity thereto, (viii) SEQ ID NO: 3 and SEQ ID NO: 14, fragments thereof, or sequences have at least 90% sequence identity thereto, (ix) SEQ ID NO: 3 and SEQ ID NO: 24, fragments thereof, or sequences have at least 90% sequence identity thereto, (x) SEQ ID NO: 3 and SEQ ID NO: 30, fragments thereof, or sequences have at least 90% sequence identity thereto, (xi) SEQ ID NO: 3 and SEQ ID NO: 34, fragments thereof, or sequences have at least 90% sequence identity thereto, (xii) SEQ ID NO: 6 and SEQ ID NO: 14, fragments thereof, or sequences have at least 90% sequence identity thereto, (xiii) SEQ ID NO: 6 and SEQ ID NO: 24, fragments thereof, or sequences have at least 90% sequence identity thereto, (xiv) SEQ ID NO: 6 and SEQ ID NO: 30, fragments thereof, or sequences have at least 90% sequence identity thereto, (xv) SEQ ID NO: 6 and SEQ ID NO: 34, fragments thereof, or sequences have at least 90% sequence identity thereto, (xvi) SEQ ID NO: 14 and SEQ ID NO: 24, fragments thereof, or sequences have at least 90% sequence identity thereto, (xvii) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xviii) SEQ ID NO: 24 and SEQ ID NO: 30, fragments thereof, or sequences have at least 90% sequence identity thereto, (xix) SEQ ID NO: 24 and SEQ ID NO: 34, fragments thereof, or sequences have at least 90% sequence identity thereto, (xx) SEQ ID NO: 30 and SEQ ID NO: 34, fragments thereof, or sequences have at least 90% sequence identity thereto are determined.

In a twelveth aspect, the invention relates to a method for diagnosing dilated cardiomyopathy and diagnosing the severity of dilated cardiomyopathy comprising the steps of:
(i) determining an expression profile of a set comprising at least two miRNAs representative for dilated cardiomyopathy in a body fluid sample from a subject, and
(ii) comparing said expression profile to a reference, wherein the comparison of said expression profile to said reference allows for diagnosing dilated cardiomyopathy and diagnosing the severity of dilated cardiomyopathy It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

It is further preferred that the diagnosing of dilated cardiomyopathy and the diagnosing of the severity of dilated cardiomyopathy is carried out simultaneously.

More preferably, the simultaneous diagnosing of dilated cardiomyopathy and the diagnosing of the severity of dilated cardiomyopathy is carried out from the same the set comprising at least two miRNAs.

Preferably, the set comprising at least two miRNAs for diagnosing of dilated cardiomyopathy and the diagnosing of the severity of dilated cardiomyopathy is selected from the group consisting SEQ ID NO: 1, 3, 6, 14, 24, 27, 30, 34.

Preferably, the set comprising at least two miRNAs is selected from the set of miRNAs listed in FIG. 3B.

It is more preferred that for (simultaneous) diagnosing of dilated cardiomyopathy and the diagnosing of the severity of dilated cardiomyopathy the set comprising at least two miRNAs having (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 30, fragments thereof, or sequences have at least 90% sequence identity thereto, (vi) SEQ ID NO: 1 and SEQ ID NO: 34, fragments thereof, or sequences have at least 90% sequence identity thereto, (vii) SEQ ID NO: 3 and SEQ ID NO: 6, fragments thereof, or sequences have at least 90% sequence identity thereto, (viii) SEQ ID NO: 3 and SEQ ID NO: 14, fragments thereof, or sequences have at least 90% sequence identity thereto, (ix) SEQ ID NO: 3 and SEQ ID NO: 24, fragments thereof, or sequences have at least 90% sequence identity thereto, (x) SEQ ID NO: 3 and SEQ ID NO: 30, fragments thereof, or sequences have at least 90% sequence identity thereto, (xi) SEQ ID NO: 3 and SEQ ID NO: 34, fragments thereof, or sequences have at least 90% sequence identity thereto, (xii) SEQ ID NO: 6 and SEQ ID NO: 14, fragments thereof, or sequences have at least 90% sequence identity thereto, (xiii) SEQ ID NO: 6 and SEQ ID NO: 24, fragments thereof, or sequences have at least 90% sequence identity thereto, (xiv) SEQ ID NO: 6 and SEQ ID NO: 30, fragments thereof, or sequences have at least 90% sequence identity thereto, (xv) SEQ ID NO: 6 and SEQ ID NO: 34, fragments thereof, or sequences have at least 90% sequence identity thereto, (xvi) SEQ ID NO: 14 and SEQ ID NO: 24, fragments thereof, or sequences have at least 90% sequence identity thereto, (xvii) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xviii) SEQ ID NO: 24 and SEQ ID NO: 30, fragments thereof, or sequences have at least 90% sequence identity thereto, (xix) SEQ ID NO: 24 and SEQ ID NO: 34, fragments thereof, or sequences have at least 90% sequence identity thereto, (xx) SEQ ID NO: 30 and SEQ ID NO: 34, fragments thereof, or sequences have at least 90% sequence identity thereto are determined.

In thirteenth aspect, the invention relates to a method for assessing the cardiac contractility comprising the steps of:
(i) determining an expression profile of a set comprising at least two miRNAs representative for cardiac contractility in a body fluid sample from a subject, and
(ii) comparing said expression profile to a reference, wherein the comparison of said expression profile to said reference allows for assessing of the cardiac contractility, It is preferred, that the cardiac contractility is the left ventricular ejection volume.

It is preferred that the body fluid sample is a blood sample, preferably a blood cell sample or a leukocyte containing sample, particularly preferred it is a whole blood, PBMC, serum or plasma sample, more particularly preferred it is a whole blood sample.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs for assessing the cardiac contractility is selected from the group consisting SEQ ID NO: 1, 3, 6, 14, 24, 27, 30, 34.

Preferably, the set comprising at least two miRNAs is selected from the set of miRNAs listed in FIG. 3B.

It is more preferred that assessing the cardiac contractility the set comprising at least two miRNAs having (i) SEQ ID NO: 1 and SEQ ID NO: 3, fragments thereof, or sequences have at least 90% sequence identity thereto, (ii) SEQ ID NO: 1 and SEQ ID NO: 6, fragments thereof, or sequences have at least 90% sequence identity thereto, (iii) SEQ ID NO: 1 and SEQ ID NO: 14, fragments thereof, or sequences have at least 90% sequence identity thereto, (iv) SEQ ID NO: 1 and SEQ ID NO: 24, fragments thereof, or sequences have at least 90% sequence identity thereto, (v) SEQ ID NO: 1 and SEQ ID NO: 30, fragments thereof, or sequences have at least 90% sequence identity thereto, (vi) SEQ ID NO: 1 and SEQ ID NO: 34, fragments thereof, or sequences have at least 90% sequence identity thereto, (vii) SEQ ID NO: 3 and SEQ ID NO: 6, fragments thereof, or sequences have at least 90% sequence identity thereto, (viii) SEQ ID NO: 3 and SEQ ID NO: 14, fragments thereof, or sequences have at least 90% sequence identity thereto, (ix) SEQ ID NO: 3 and SEQ ID NO: 24, fragments thereof, or sequences have at least 90% sequence identity thereto, (x) SEQ ID NO: 3 and SEQ ID NO: 30, fragments thereof, or sequences have at least 90% sequence identity thereto, (xi) SEQ ID NO: 3 and SEQ ID NO: 34, fragments thereof, or sequences have at least 90% sequence identity thereto, (xii) SEQ ID NO: 6 and SEQ ID NO: 14, fragments thereof, or sequences have at least 90% sequence identity thereto, (xiii) SEQ ID NO: 6 and SEQ ID NO: 24, fragments thereof, or sequences have at least 90% sequence identity thereto, (xiv) SEQ ID NO: 6 and SEQ ID NO: 30, fragments thereof, or sequences have at least 90% sequence identity thereto, (xv) SEQ ID NO: 6 and SEQ ID NO: 34, fragments thereof, or sequences have at least 90% sequence identity thereto, (xvi) SEQ ID NO: 14 and SEQ ID NO: 24, fragments thereof, or sequences have at least 90% sequence identity thereto, (xvii) SEQ ID NO: 14 and SEQ ID NO: 30, fragments thereof, or sequences have at least 90% sequence identity thereto, (xxii) SEQ ID NO: 14 and SEQ ID NO: 34, fragments thereof, or sequences have at least 90% sequence identity thereto, (xviii) SEQ ID NO: 24 and SEQ ID NO: 30, fragments thereof, or sequences have at least 90% sequence identity thereto, (xix) SEQ ID NO: 24 and SEQ ID NO: 34, fragments thereof, or sequences have at least 90% sequence identity thereto, (xx) SEQ ID NO: 30 and SEQ ID NO: 34, fragments thereof, or sequences have at least 90% sequence identity thereto are determined.

In summary, the present invention is composed of the following items:

1. A method for diagnosing and/or prognosing of DCM comprising the steps of:
   (i) determining an expression profile of a set comprising at least two miRNAs representative for DCM in a body fluid sample from a subject, and
   (ii) comparing said expression profile to a reference, wherein the comparison of said expression profile to said reference allows for the diagnosis and/or prognosis of DCM,
   wherein the nucleotide sequences of the miRNAs comprised in the set are selected from the group consisting of SEQ ID NO: 1 to 387, a fragment thereof, and a sequence having at least 80% sequence identity thereto.
2. The method of item 1, wherein the body fluid sample is a blood sample, preferably a blood cell sample or a leukocyte containing sample, or a fraction thereof.
3. The method of item 1 or 2, wherein the miRNAs comprised in the set are selected from the group consisting of SEQ ID NO: 1, 3, 6, 14, 24, 27, 30, 34.
4. The method of any of the items 1 to 2, wherein the set of miRNAs comprises at least one of the sets of miRNAs listed in FIG. 3A or FIG. 3B.
5. The method according to any of the items 1 to 4, wherein the reference are reference expression profiles of at least two subjects with at least two known clinical conditions from which at least one is DCM, wherein the reference expression profiles are the profiles of a set comprising at least two miRNAs that have nucleotide sequences that correspond to the nucleotide sequences of the miRNAs of step (i).
6. The method according to any of the items 1 to 4, wherein the reference is an algorithm or mathematical function that is obtained from reference expression profiles of at least two subjects with at least two known clinical conditions from which at least one is DCM, wherein the reference expression profiles are the profiles of a set comprising at least two miRNAs that have nucleotide sequences that correspond to the nucleotide sequences of the miRNAs of step (i).
7. A set comprising polynucleotides for detecting a set comprising at least two miRNAs for diagnosing and/or prognosing of DCM in a body fluid sample from a subject, wherein the nucleotide sequences of the miRNAs comprised in the set are selected from the group consisting of SEQ ID NO: 1 to 387.
8. The set comprising polynucleotides of item 7, wherein the body fluid sample is a blood sample, preferably a blood cell sample or a leukocyte containing sample, or a fraction thereof.
9. The set comprising polynucleotides of items 7 or 8, wherein the set comprising at least two miRNAs is selected from the group consisting of SEQ ID NO: 1, 3, 6, 14, 24, 27, 30, 34.
10. The set comprising polynucleotides of any of the items 7 to 8, wherein set comprising at least two miRNAs is selected from the set of miRNAs listed in FIG. 3A or FIG. 3B.
11. The set comprising polynucleotides according to any of the items 7 to 10, wherein
    (i) the polynucleotides comprised in the set are complementary to the miRNAs comprised in the set according to items 7 to 10,
    (ii) the polynucleotides comprised in the set are fragments of the polynucleotides comprised in the set according to (i), or
    (iii) the polynucleotides comprised in the set have at least 80% sequence identity to the polynucleotide sequences of the polynucleotides comprised in the set according to (i) or polynucleotide fragments comprised in the set according to (ii).
12. Use of set of polynucleotides according to any of the items 7 to 11 for diagnosing and/or prognosing DCM in a subject
13. A set of at least two primer pairs for determining the expression level of a set of miRNAs in a body fluid sample of a subject suffering or suspected of suffering from DCM, wherein the primer pairs are specific for at least two miRNAs selected from the group consisting of SEQD ID NO: 1 to 387
14. The set of primer pairs of item 13, wherein the body fluid sample is a blood sample, preferably a blood cell sample or a leukocyte containing sample, or a fraction thereof.
15. The set of primer pairs of items 13 or 14, wherein the primer pairs are specific for at least two miRNAs selected from the group consisting of SEQ ID NO: 1, 3, 6, 14, 24, 27, 30, 34.
16. The set of primer pairs of any of the items 13 to 14, wherein the sets of miRNAs comprises at least one of the sets of miRNAs listed in FIG. 3A or FIG. 3B.
17. Use of set of primer pairs according to any of the items 13 to 16 for diagnosing and/or prognosing DCM in a subject 18. Means for diagnosing and/or prognosing of DCM in a body fluid sample of a subject comprising:
   (i) a set of at least two polynucleotides according to any of the items 7 to 11 or
   (ii) a set of primer pairs according to any of the items 13 to 16.
19. The means of item 18, wherein said means comprise a biochip, a RT-PCT system, a PCR-system, a flow cytometer or a next generation sequencing system.
20. The means of items 18 or 19, wherein the body fluid sample is a blood sample, preferably a blood cell sample or a leukocyte containing sample, or a fraction thereof.
21. A kit for diagnosing and/or prognosing of DCM comprising
   (i) means for determining an expression profile of a set comprising at least two miRNAs representative for DCM in a body fluid sample from a subject, and
   (ii) at least one reference.
22. The kit of item 21, wherein the nucleotide sequences of said miRNAs are selected from the group consisting of SEQ ID NO: 1 to 387, a fragment thereof, and a sequence having at least 80% sequence identity thereto.
23. The kit of items 21 or 22, wherein said kit comprises the means according to any of the items 18 to 20.
24. A set of miRNAs isolated from a body fluid sample from a subject for diagnosing and/or prognosing of DCM, wherein the miRNAs are selected from the group consisting of SEQ ID 1 to 387
25. The set of miRNAs of item 24, wherein the body fluid sample is a blood sample, preferably a blood cell sample or a leukocyte containing sample, or a fraction thereof.
26. The set of miRNAs of items 24 or 25, wherein the miRNAs are selected from the group consisting of SEQ ID NO: 1, 3, 6, 14, 24, 27, 30, 34.
27. The set of miRNAs of items 24 or 25, wherein the set of miRNAs comprises at least one of the sets of miRNAs listed in FIG. 3A or FIG. 3B.
28. Use of a set of miRNAs according to any of the items 24 to 27 for diagnosing and/or prognosing of DCM in a subject.
29. A method for diagnosing the severity of dilated cardiomyopathy, comprising the steps of:
   (i) determining an expression profile of a set comprising at least two miRNAs representative for dilated cardiomyopathy in a body fluid sample from a subject, and
   (ii) comparing said expression profile to a reference, wherein the comparison of said expression profile to said reference allows for the diagnosis of the severity of dilated cardiomyopathy,
   wherein the nucleotide sequences of the miRNAs comprised in the set are selected from the group consisting of SEQ ID NO: 1, 3, 6, 14, 24, 30, 34, a fragment thereof, and a sequence having at least 80% sequence identity thereto.
30. The method of item 29, wherein the body fluid sample is a blood sample, preferably a blood cell sample or a leukocyte containing sample, or a fraction thereof.
31. A method for diagnosing dilated cardiomyopathy and diagnosing the severity of dilated cardiomyopathy comprising the steps of:
   (i) determining an expression profile of a set comprising at least two miRNAs representative for dilated cardiomyopathy in a body fluid sample from a subject, and
   (ii) comparing said expression profile to a reference, wherein the comparison of said expression profile to said reference allows for diagnosing dilated cardiomyopathy and diagnosing the severity of dilated cardiomyopathy
   wherein the nucleotide sequences of the miRNAs comprised in the set are selected from the group consisting of SEQ ID NO: 1, 3, 6, 14, 24, 30, 34, a fragment thereof, and a sequence having at least 80% sequence identity thereto.
32. The method of item 31, wherein the diagnosing dilated cardiomyopathy and diagnosing the severity of dilated cardiomyopathy is carried out simultaneously
33. The method of item 31 or 32, wherein the body fluid sample is a blood sample, preferably a blood cell sample or a leukocyte containing sample, or a fraction thereof.
34. A method for assessing the cardiac contractility comprising the steps of
   (i) determining an expression profile of a set comprising at least two miRNAs representative for cardiac contractility in a body fluid sample from a subject, and
   (ii) comparing said expression profile to a reference, wherein the comparison of said expression profile to said reference allows for assessing of the cardiac contractility,
   wherein the nucleotide sequences of the miRNAs comprised in the set are selected from the group consisting of SEQ ID NO: 1, 3, 6, 14, 24, 30, 34, a fragment thereof, and a sequence having at least 80% sequence identity thereto.
35. The method of item 34, wherein the cardiac contractility is the left ventricular ejection volume
36. The method of item 34 or 35, wherein the body fluid sample is a blood sample, preferably a blood cell sample or a leukocyte containing sample, or a fraction thereof.

BRIEF DESCRIPTION OF THE DRAWINGS

FIG. 1: MiRNAs for diagnosis or prognosis of DCM. Experimental data obtained for analysis of miRNAs on the Geniom microarray platform. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with DCM (including mild DCM and severe DCM), qmedian: ratio of median g1/median g2, logqmedian: log of qmedian, wmw_rawp: p-value obtained when applying wmw-test (Wilcoxon Mann Whitney test), wmw_adjp: adjusted p-value in order to reduce false discovery rate by Benjamini-Hochberg adjustment, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment. Data based on microarray analysis assessing 19 patients with mild and 14 patients with severe DCM in comparison to 20 healthy controls characterized by normal LVEF.

FIG. 2: MiRNAs for diagnosis or prognosis of DCM. Experimental data obtained for analysis of miRNAs on the Agilent microarray platform. Experimental details: SEQ ID NO: sequence identification number, miRNA: identifier of the miRNA according to miRBase, median g1:
  median intensity obtained from microarray analysis for healthy controls, median g2: median intensity obtained from microarray analysis for individuals with DCM (including mild DCM and severe DCM), qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, limma_rawp: p-value obtained when applying limma-test, limma_adjp: adjusted p-value in order to reduce false discovery rate by Benjamini-Hochberg adjustment. Data based on microarray analysis assessing 19 patients with mild and 14 patients with severe DCM in comparison to 20 healthy controls characterized by normal LVEF.

FIG. 3: Sets of miRNAs (miRNA-signatures: FIG. 3 A: DCM-1 to DCM-38; FIG. 3B: DCM-39 to DCM-94) that allow for effective diagnosis and/or prognosis of DCM when differentiating DCM and healthy controls. Experimental details: # miRNAs: number of miRNAs contained in the respective set of miRNAs; miRNA: identifier of the miRNA according to miRBase, Accuracy for classification between healthy controls and DCM patients. Data DCM-1-38 is based on microarray analysis assessing 19 patients with mild and 14 patients with severe DCM in comparison to 20 healthy controls characterized by normal LVEF. Data DCM-39-DCM94 is based on Geniom microarray analysis assessing 32 patients with mild (moderate) and 21 patients with severe DCM in comparison to 39 healthy controls.

FIG. 5B: miRNAs for diagnosis of DCM; graphical representation of statistical key figures obtained when comparing DCM patients from healthy controls (from left to right): bar-plot ttest raw p-value: frequency of miRNAs obtained when applying t-test; barplot t-test adjusted p-value: frequency of miRNAS obtained when applying t-test including Benjamini-Hochberg adjustment; barplot AUC: frequency of miRNAs obtained when applying area under the curve (AUC) test. Data based on Geniom microarray analysis assessing 32 patients with mild (moderate) and 21 patients with severe DCM in comparison to 39 healthy controls characterized by normal LVEF (for details see Table 1 in Example 2).

FIG. 6A: diagnostic miRNAs that are upregulated when DCM patients are compared to healthy controls. FIG. 6B: miRNAs that are downregulated when DCM patients are compared to healthy controls. Data based on Geniom microarray analysis assessing 32 patients with mild (moderate) and 21 patients with severe DCM in comparison to 39 healthy controls characterized by normal LVEF (for details see Table 1 in Example 2).

FIG. 7A: ROC (receiver operating characteristic) curves for 3 of the most promising diagnostic significant miRNAs for differentiating DCM patients from healthy controls with highest statistical power: hsa-miR-558, hsa-miR-122*, has-miR-520d-5p leading to AUC (area under the curve) values of 0.7, 0.7 and 0.71. FIG. 7B: left side: ROC (receiver operating characteristic) curves for a set, therefore combining the statistical information, of the 8 most promising diagnostic significant miRNAs for differentiating DCM patients from healthy controls: hsa-miR-558-122*, -520d-5p, -622, -519e*, -1228*, -200b*, -1231 leading to AUC (area under the curve) value of 0.81: right side, left bars indicate the obtained accuracy, specificity and sensitivity of 25 repeated cross-validation runs while right bars denote randomized permutation tests as negative control. Data based on Geniom microarray analysis assessing 32 patients with mild (moderate) and 21 patients with severe DCM in comparison to 39 healthy controls characterized by normal LVEF (for details see Table 1 in Example 2).

FIG. 11: ROC (receiver operating characteristic) curves for 5 of the most promising diagnostic significant miRNAs for differentiating DCM patients from healthy controls: hsa-miR-622, -1231, -200b*, -519e*, -1228*. Data based on Geniom microarray analysis assessing 32 patients with mild (moderate) and 21 patients with severe DCM in comparison to 39 healthy controls characterized by normal LVEF (for details see Table 1 in Example 2).

EXAMPLES

Figure 4:
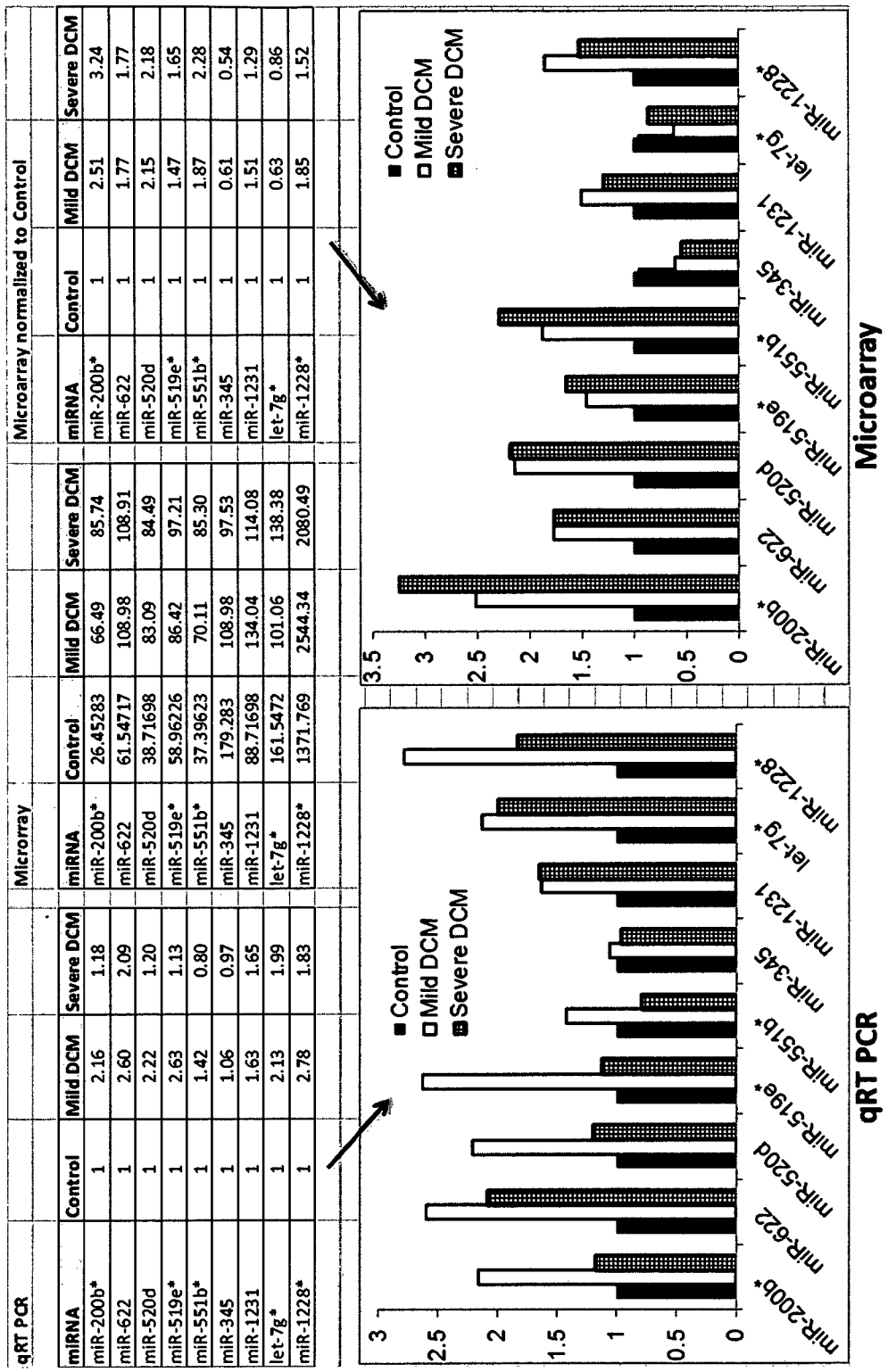
FIG. 4: Validation of the miRNA biomarker candidates, that had been identified by microarray analysis on the qRT-PCR platform. Relevant miRNA biomarker for the diagnosis of DCM include has-miR-200b*, hsa-miR-622, hsa-miR-520d, hsa-miR-519e*, hsa-miR-551b*, hsa-miR-345, hsa-miR-1231, hsa-let-7g*, hsa-miR-1228*. Left: data from qRT-PCR, Right: data from microarray analysis. Controls are healthy controls. DCM samples include mild and severe DCM patients. Results were normalized to controls in order to be able to compare qRT PCR and microarray results. The y-axis depicts the Fold Change of the respective miRNA of mild and severe DCM-patients in relation to the control samples. Data based on qRT-PCR analysis assessing 19 patients with mild and 14 patients with severe DCM in comparison to 20 healthy controls characterized by normal LVEF.

The Examples are designed in order to further illustrate the present invention and serve a better understanding. They are not to be construed as limiting the scope of the invention in any way.

Example 1

Samples

All blood donors participating in this study have given their written informed consent. The patient samples have been prepared at University Clinic Heidelberg (Innere Medizin III). Besides the samples of mild (n=19 patients) or severe (n=14 patients) cardiomyopathy patients, also normal control samples (n=20 controls) were provided.

miRNA Extraction and Microarray Screening

Blood of patients has been extracted as previously described [1]. In brief, 2.5 to 5 ml blood was extracted in PAXgene Blood RNA tubes (BD, Franklin Lakes, N.J. USA) and centrifuged at 5000×g for 10 min at room temperature. The miRNeasy kit (Qiagen GmbH, Hilden) was used to isolate total RNA including miRNA from the resuspended pellet according to manufacturer's instructions. The eluted RNA was stored at −70° C.

All samples were analyzed with the Geniom RT Analyzer (febit biomed GmbH, Heidelberg, Germany) on a Geniom Biochip miRNA Homo sapiens v16. or on the Agilent microRNA microarray platform at the in-house genomic service department. Measuring on the Agilent platform was according to the manufacturer recommendations. On the Geniom platform each array contains 5 replicates of all miRNAs and miRNA* sequences as annotated in the Sanger miRBase releases 16.0. On-chip sample labeling with biotin was carried out by microfluidic-based primer extension labeling of miRNAs (MPEA [2]). Following hybridization for 16 hours at 42° C., the biochip was washed and a program for signal enhancement was carried out. All steps from sample loading to miRNA detection were processed without any manual intervention and inside the machine. The detection pictures were evaluated using the Geniom Wizard Software. For each feature, the median signal intensity was calculated. Following a background correction step, the median of the 7 replicates of each miRNA was computed. To normalize the data across different arrays on the Geniom and the Agilent platform, quantile normalization [3] was applied and all further analyses were carried out using the normalized and background subtracted intensity values.

Statistical Analysis

To estimate the value of single miRNAs, t-tests (unpaired, two-tailed) were carried out. The resulting p-values have been adjusted for multiple testing by Benjamini-Hochberg adjustment [4, 5]. In addition to this single biomarker analysis, we performed supervised classification of samples by using Support Vector Machines (SVM [6]) as implemented in the R e1071 package [7]. As parameters, we evaluated different kernel methods including linear, polynomial (degree 2 to 5), sigmoid and radial basis function kernels. The cost parameter was sampled from 0.01 to 10 in decimal powers. As subset selection technique, a filter approach based on t-test was carried out. In each iteration, the s miRNAs with lowest p-values were computed on the training set in each fold of a standard 10-fold cross validation, where s was sampled in regular intervals between 2 and 300. The respective subset was used to train the SVM and to carry out the prediction of the test samples in the cross validation. To compute probabilities for classes instead of class labels, a regression approach based on the output of the support vectors has been applied. To test for overtraining, non-parametric permutation tests have been applied. All computations were carried out using R [7], a freely available language for statistical tasks.

References

1. Keller A, Leidinger P, Borries A, Wendschlag A, Wucherpfennig F, Scheffler M, Huwer H, Lenhof H P, Meese E: miRNAs in lung cancer—studying complex fingerprints in patient's blood cells by microarray experiments. BMC Cancer 2009, 9:353.
2. Vorwerk S, Ganter K, Cheng Y, Hoheisel J, Stahler P F, Beier M: Micro fluidic-based enzymatic on-chip labeling of miRNAs. N Biotechnol 2008, 25(2-3):142-149.
3. Bolstad B M, Irizarry R A, Astrand M, Speed T P: A comparison of normalization methods for high density oligonucleotide array data based on variance and bias. Bioinformatics 2003, 19(2):185-193.
4. Benjamini Y, Drai D, Elmer G, Kafkafi N, Golani I: Controlling the false discovery rate in behavior genetics research. Behav Brain Res 2001, 125(1-2):279-284.
5. Hochberg Y: A sharper bonferroni procedure for multiple tests of significance. Biometrica 1988, 75:185-193.
6. Vapnik V: The nature of statistical learning theory, 2nd edition edn. New York: Spinger; 2000.
7. Team R: R: A Language and Environment for Statistical Computing. In. Vienna: R Foundation for Statistical Computing; 2008.

Example 2

Non-ischemic heart failure (NIHF) is one of todays leading cardiovascular disorders. Unfortunately, therapeutic options are often limited and mainly linked to the severity of the disease. Hence, circulating biomarkers play an important role in early disease states, clinical management and cardiac risk assessment of DCM. Dilated cardiomyopathy (DCM) is the most prevalent form of non-ischemic heart failure (NIHF).

The present study evaluated the role of microRNAs as novel biomarkers for dilated cardiomyopathy (DCM). We assessed for the first time whole-genome microRNA expression profiles in 53 DCM patients and 39 controls. We identified subsets of microRNAs that show altered expression levels in peripheral blood of DCM patients, with miR-520d-5p being the most significantly dysregulated. Furthermore, we are able to demonstrate that 8 of these dysregulated miRNAs can discriminate DCM from control patients both as single markers and when combined in a multi-variate signature (accuracy 70%, specificity 66%, sensitivity 74%, AUC=0.81).

The present data strengthen the role of microRNAs as biomarkers for DCM and as potential tools to assess cardiac dysfunction due to other causes in DCM and other types of non-ischemic heart failure. In the future, microRNAs might also aid in risk stratification and therapeutic management of heart failure.

Introduction

Non-ischemic heart failure is among the most prevalent causes for heart transplantation and sudden cardiac death. It can be caused by a variety of cardiovascular disorders like idiopathic dilated cardiomyopathy or myocarditis. Affected individuals suffer from an often progressively impaired cardiac contractility followed by ventricular dilation. The therapeutic management of these patients is challenging since causative approaches are lacking in the majority of cases. In fact, symptomatic therapy is mostly correlated to disease severity and the estimated individual cardiac risk. Circulating biomarkers like brain natriuretic peptide (BNP) or cardiac troponis are therefore one of todays frequently used tools to facilitate clinical management of heart failure patients (PMID16293638; PMID: 18243857). Nevertheless, there is still an undeniable need for additional, easy accessible, reliable biomarkers to identify non ischemic heart failure in early disease states and objectively evaluate disease severity.

Small non-coding miRNAs impact on the expression of target genes on a posttranscriptional level (PMID: 14744438), thereby regulating a magnitude of physiological and pathological processes. Recent studies tried to elucidate the role of microRNAs as potential biomarkers for cardiovascular diseases and especially heart failure (Tijsen/Pinto, PMID: 20185794; Matkovich, PMID: 19237659; Naga Prasad PMID: 19641226). However, only preliminary data on the role of microRNAs as potential biomarkers for non-ischemic heart failure are available.

In the present study we assessed miRNA expression profiles in patients with DCM on a genome-wide level using microfluidic primer extension arrays. Whole blood samples were obtained from DCM patients regarding their different degrees of cardiac impairment and compared to healthy controls. We found distinct miRNAs to be dysregulated in DCM patients, some of which allow discrimination of mild versus severe DCM.

Materials and Methods
Patient Recruitment

The present study has been approved by the local ethics committee and participants have given written informed consent. In the screening cohort we included 53 DCM patients undergoing elective coronary angiography. DCM defined as an impairment of left ventricular contractility in the absence of significant coronary artery disease (CAD). Both criteria were confirmed using left ventricular angiography and coronary angiography. Hence, ischemic heart failure was invasively ruled out in all patients enrolled. Patients with valvular heart disease, acute myocarditis or a history of cardio-toxic chemotherapy were excluded. 21 individuals suffered from severe reduction in cardiac contractility (mean LV-EF=21%), 32 had mild-moderate impairment (mean LV-EF=41%). MicroRNA profiles from 39 control subjects without significant CAD and normal LV-EF served as controls. For validation of selected miRNAs we recruited an independent patient cohort consisting of 14 DCM patients and 8 controls

TABLE 1

Patient characteristics (cohort 1).

| Characteristics | Control Patients (n = 39) | Patients with moderate DCM (n = 32) | Patients with severe DCM (n = 21) |
|---|---|---|---|
| Age (years) | 63 ± 13 | 58 ± 17 | 62 ± 13 |
| Male/female (n/n) | 23/16 | 24/8 | 20/1 |
| Current smoking, n (%) | 12 (31) | 7 (22) | 5 (24) |
| DM, n (%) | 12 (31) | 6 (19) | 5 (24) |
| Hypertension, n (%) | 28 (72) | 23 (72) | 13 (62) |
| BNP (pg/mL) | 146 ± 92 | 896 ± 1531 | 3788 ± 4068 |
| TC (mmol/L) | 4.6 ± 1.1 | 4.6 ± 1.5 | 3.9 ± 1.2 |
| HDL (mmol/L) | 1.3 ± 0.5 | 1.2 ± 0.4 | 1.0 ± 0.4 |
| LDL (mmol/L) | 2.6 ± 0.8 | 2.2 ± 1.2 | 2.1 ± 0.9 |
| WBC (/nl) | 8.5 ± 3 | 8.4 ± 3 | 8.8 ± 2 |
| Creatinine (μmol/L) | 97 ± 80 | 150 ± 212 | 97 ± 27 |
| Urea (mg/dL) | 5.8 ± 2.3 | 7.5 ± 4.8 | 6.8 ± 2.7 |

DM = Diabetes mellitus, BNP = brain natriuretic peptide, TC = total cholesterol, HDL = high-density lipoprotein, LDL = low-density lipoprotein, WBC = white blood cell count.

TABLE 2

Patient characteristics (cohort 2).

| Characteristics | Control Patients (n = 8) | Patients with moderate DCM (n = 7) | Patients with severe DCM (n = 7) |
|---|---|---|---|
| Age (years) | 59.5 ± 12.5 | 59.4 ± 13 | 59 ± 7.8 |
| Male/female (n/n) | 4/4 | 3/4 | 5/2 |
| Current smoking, n (%) | 3 (38) | 2 (29) | 2 (29) |
| DM, n (%) | 3 (38) | 1 (14) | 3 (43) |
| Hypertension, n (%) | 5 (62) | 3 (43) | 5 (71) |
| Hyperlipidaemia, n (%) | 3 (38) | 4 (57) | 4 (57) |
| WBC (/nl) | 8.1 ± 2 | 8.2 ± 1 | 8.0 ± 1 |
| Creatinine (mg/dL) | 86 ± 27 | 80 ± 8.8 | 86 ± 27 |
| Urea (mmol/L) | 5.0 ± 2.3 | 4.8 ± 0.7 | 5.8 ± 3.2 |

MiRNA Expression Profiling from Peripheral Whole Blood Samples 5 ml of peripheral blood was collected from all participants according to a standardized protocol in PAXgene Blood RNA tubes (BD, USA) and stored for a maximum of 3 days at 4° C. until total RNA was extracted using the miRNeasy Mini Kit (Qiagen, Germany) (Lainscak, PMID: 20024637). Personnel blinded to patient characteristics performed microRNA expression profiling including data acquisition and normalization. Samples for microarray experiments were analyzed with the Geniom Real-time Analyzer (febit, Germany) using the Geniom Biochip miRNA Homo sapiens. Each array contains 7 replicates of 866 miRNAs and miRNA* sequences as annotated in the Sanger miRBase 12.0. Sample labeling with biotin was carried out by microfluidic-based enzymatic on-chip labeling of miRNAs (MPEA).

After hybridization for 16 hours at 42° C., the biochip was washed, signals were measured and the resulting images were evaluated using the Geniom Wizard Software (febit, Germany). For each array, the median signal intensity of all features was extracted from the raw data file. Hence, seven intensity values were calculated for each miRNA corresponding to each replicate on the array. Finally, after background correction, the seven replicate intensity values of each miRNA were summarized by their median value. To normalize the data across different arrays, quantile normalization was applied. All further analyses were based on these normalized and background subtracted data.

We validated selected miRNAs in an independent cohort using quantitative real-time PCR. Therefore, custom miRNA primer assays were synthesized by Qiagen (Hilden, Germany) and expression levels of miR-520d, miR-200b, miR-622, miR-519e, miR-1231 and miR-1228 were assessed essentially as described before (PMID:20886220). The small nuclear RNA RNU6B-2 served as the reference.

Statistical Analysis

All statistical analyses have been carried out using the normalized expression intensities. To detect differential regulated biomarkers with relevant diagnostic information content we carried out two-tailed unpaired t-tests. For each miRNA we also computed the area under the receiver operator characteristics curve (AUC value).

To transform the high-dimensional miRNA profiles to a two-dimensional space in order to graphically represent differences between controls, mild and severe DCM patients we carried out a principal component analysis. Having computed all principal components we plotted for each sample the first and second component, corresponding to these components with highest variance. For each of the three cohorts the mean and standard deviations for these two components have been plotted.

To identify potential multi-variate DCM signatures, we applied linear kernel basis Support Vector Machines (SVM) with a stepwise forward filter feature selection technique. The classification has been evaluated using 25 repetitions of 10-fold cross-validation. To test for overtraining we repeated the same classification with 25 permutation tests, i.e., we used the same miRNA expression profiles but randomly assigned class labels. As for the single markers, we computed ROC curves and AUC values for each of the classification results.

Results

Study Design and Patient Characteristics

MiRNAs are known to be dysregulated in the course of different cardiovascular disorders. To further elucidate their expression patterns in DCM patients, we examined whole blood samples from DCM patients with different stages of disease severity. In all patients a relevant coronary artery disease was excluded by routine coronary angiography. In total we included 21 patients with severely and 32 patients with moderately impaired systolic function. 39 individuals with normal left ventricular ejection fraction served as controls. Accordingly, patients of the study groups did not differ regarding their age, gender or distribution of cardiovascular risk factors (table 1).

DCM Leads to Alterations in miRNA Expression Patterns

Figure 5:
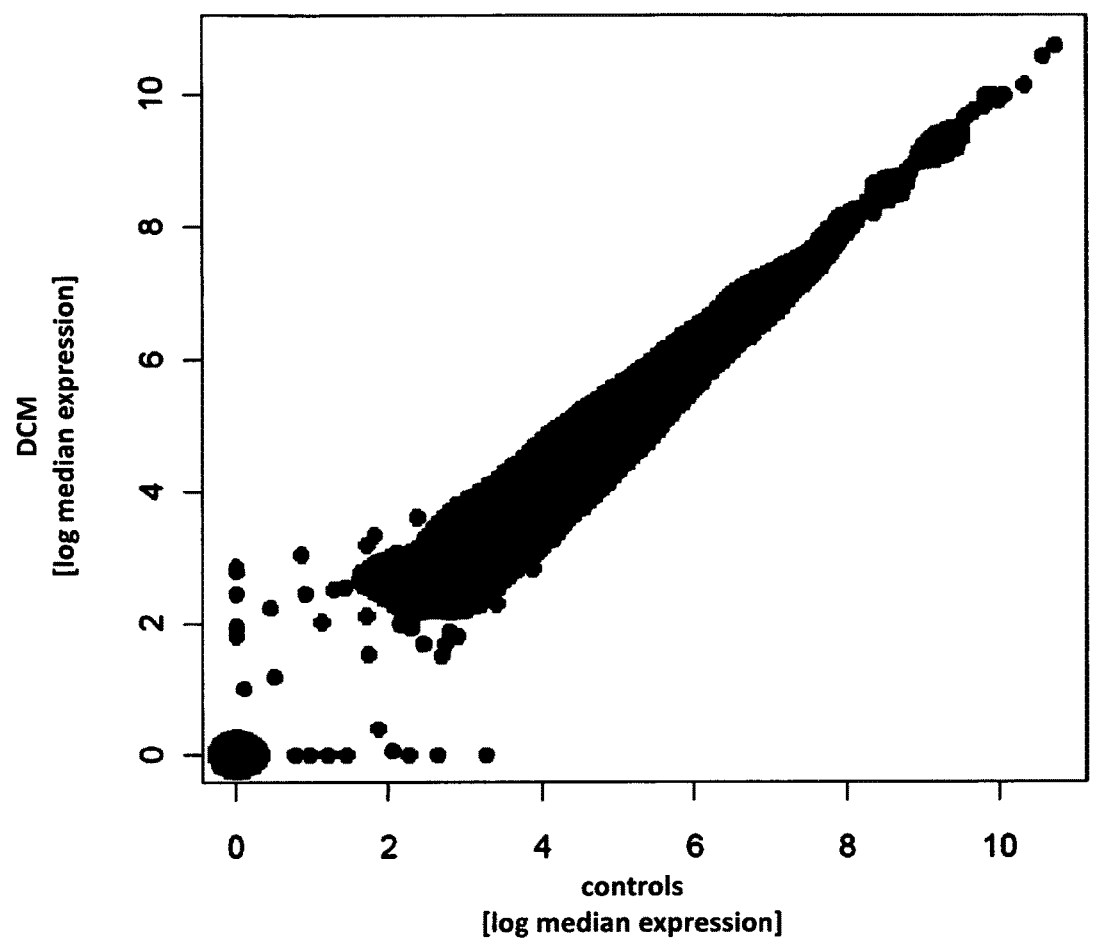
FIG. 5: A: Scatter plot from comparing miRNA expression profiles of DCM patients (y-axis) and healthy control subjects (x-axis). DCM pateints (n=53) versus healthy controls (n=39)
Figure 5:
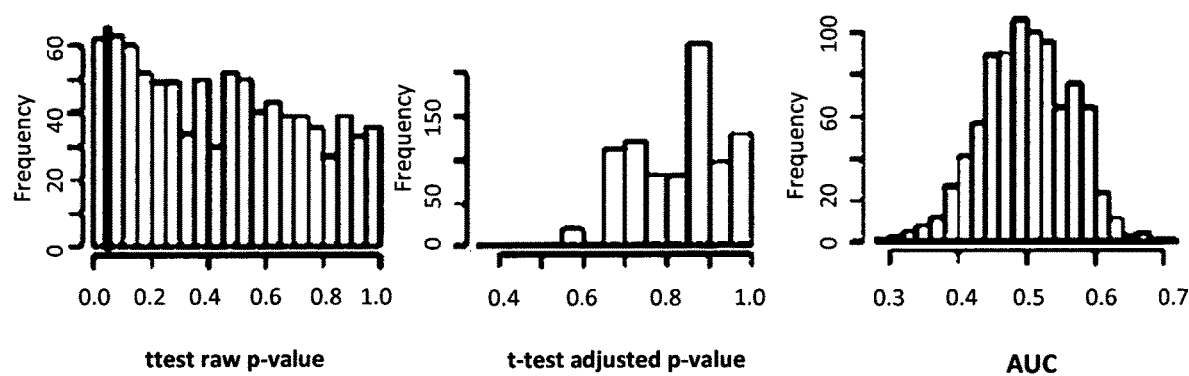
Figure 6:
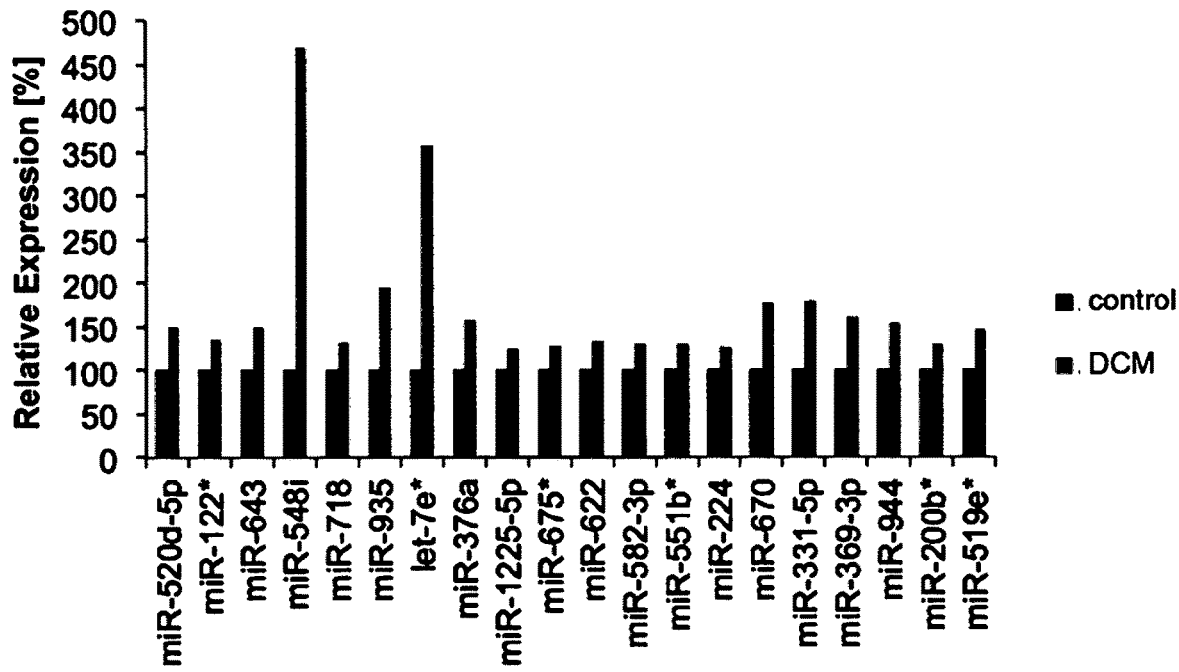
FIG. 6: miRNAs that allow for effective diagnosis of DCM when differentiating DCM and healthy controls (raw p-value <0.01); relative expression values are given for DCM patients normalized to the corresponding values in the healthy control group.
Figure 6:
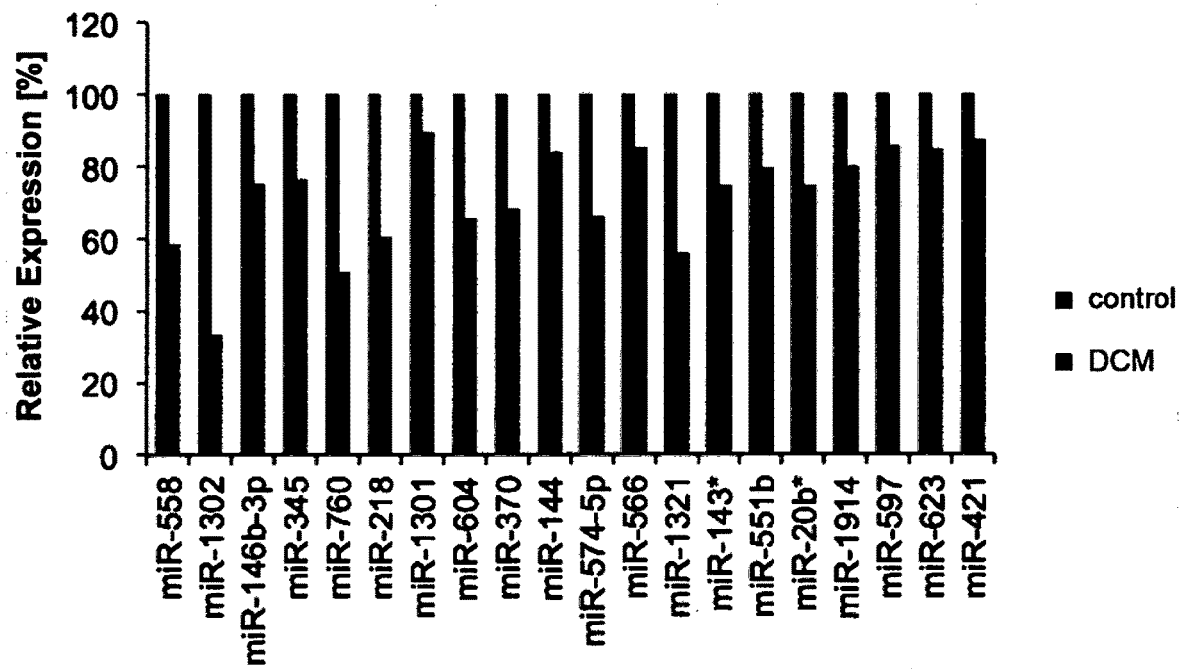
Figure 9:
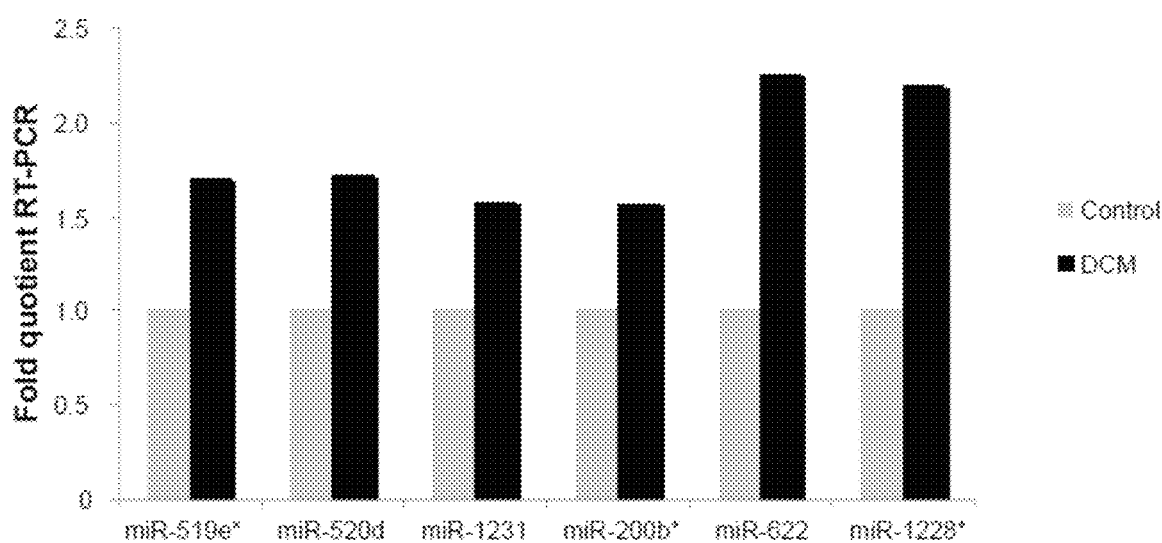
FIG. 9: validation of findings by qRT-PCR: most promising miRNAs (hsa-miR-519e*, -520d-5p, -1231, -200b*, -622, -1228*) that allow for effective diagnosis of DCM when differentiating DCM and healthy controls. The fold quotients are relative to healthy controls. Results form qRT-PCR show consistent dysregulation when compared to microarray analysis. Data based on qRT-PCR analysis in validation cohort assessing 7 patients with mild (moderate) and 7 patients with severe DCM in comparison to 8 healthy controls (for details see Table 2 in Example 2).

MiRNA expression profiles were assessed for all groups using microfluidic primer assays on a microarray platform. For most miRNAs we found a high correlation between DCM and controls as depicted in the correlation plot in FIG. 5A. However, some miRNAs were specifically dysregulated in DCM. FIG. 6A and FIG. 6B gives an overview about the 20 most significantly up—(A) or downregulated (B) miRNAs in DCM patients in comparison to individuals of the control group, given as relative expression values. To substantiate these findings, we next biologically and technically validated six selected miRNAs in an independent cohort comprising of 14 DCM patients and 8 controls. Real time PCR analysis was performed for miR-520d, miR-200b, miR-622, miR-519e, miR-1231, and miR-1228 (FIG. 9), all of them showing full concordance with the microarray results and the screening cohort.

Selected miRNAs as Biomarkers for DCM

Figure 7:
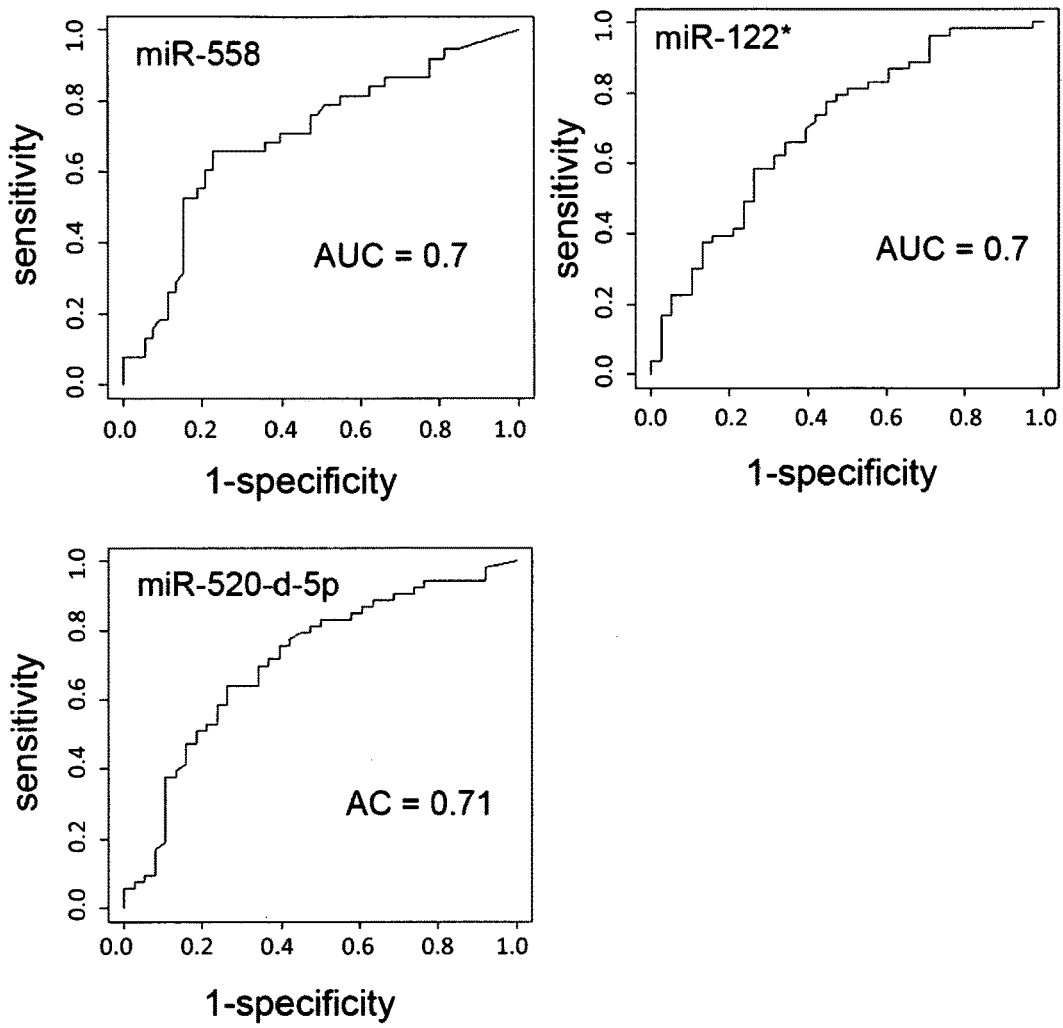
FIG. 7: Potential of single miRNAs to predict DCM.
Figure 7:
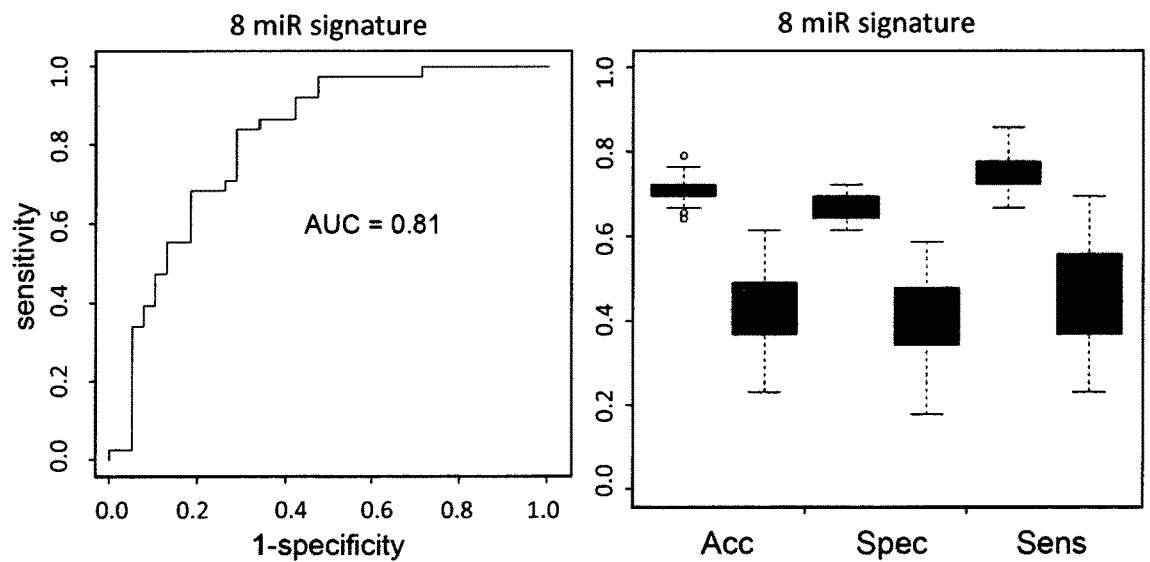

To gain further insight in the power of single miRNAs to discriminate DCM patients from controls, we applied receiver operating characteristic (ROC) analysis for miR-558, miR-122* and miR-520d-5p, which were found to be most differentially regulated in DCM patients on microarray (FIG. 7A). The AUC values of these single miRNAs ranged from 0.54 to 0.71 with miR-520d showing the highest discriminatory power as a single marker. For this miRNA, we found a sensitivity of 64%, specificity of 74%, and accuracy of 68%.

Although single miRNAs may predict the diagnosis of DCM with good sensitivity and specificity, we tested whether complex miRNA signatures derived from supervised classification may improve the test sensitivity and specificity. Hence, we combined the information content of the above described miRNAs with 5 additional, selected miRNAs (miR-200b*, miR-622, miR-519e*, miR-1231 and miR-1228*), which had been successfully replicated across different study populations and miRNA quantification techniques. The ROC analysis for these additional miRNAs as single markers for DCM are given in FIG. 11. Consequently, we applied statistical learning techniques by Support Vector Machines (SVM) with different kernels. The best results were obtained using radial basis function SVM. The cross validation procedure has been carried out 25 times to gain additional statistical significance. The best AUC for the DCM signature comprising the 8 miRNAs was 0.81 (median of 0.73) (FIG. 7B). The signature reached an average accuracy of 70%, a specificity of 66%, and a sensitivity of 74% representing an improvement as compared to the individual single miRNA biomarkers.

Dysregulation of miRNAs in Patients with DCM Correlates with Disease Severity

Figure 8:
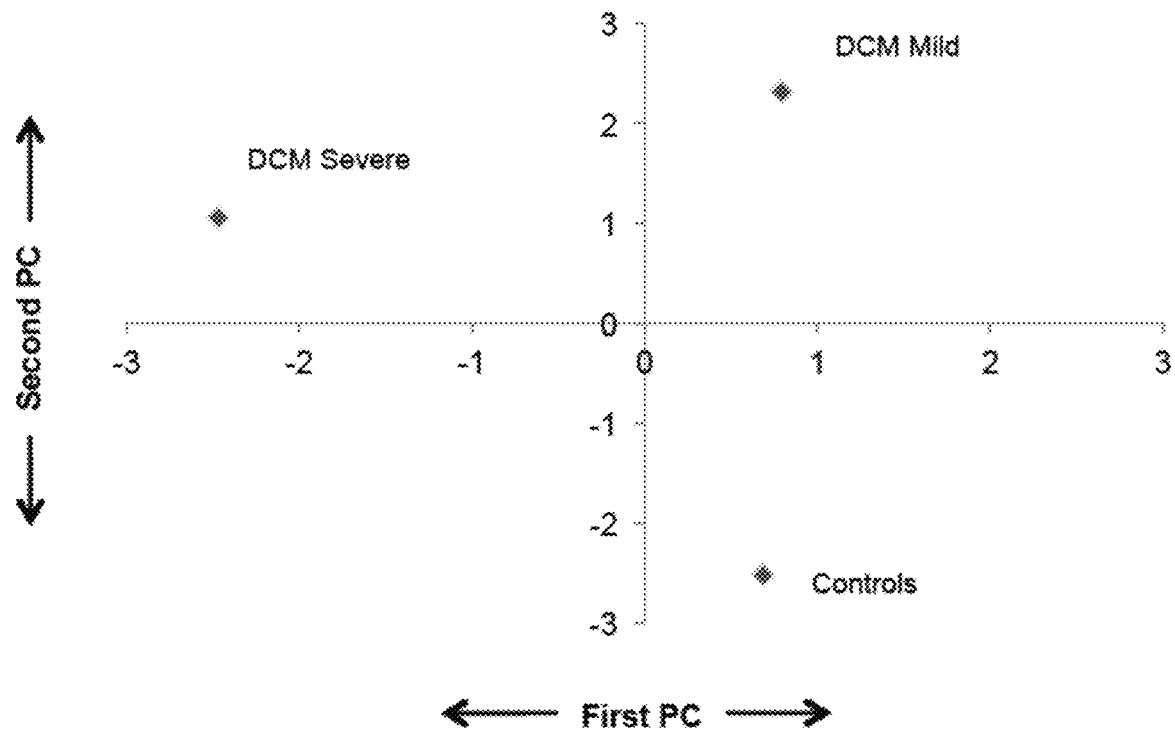
FIG. 8: Graphical representation of a Principal Component Analysis when comparing 3 groups: Controls (healthy controls), DCM Severe (patients with severe form of DCM) and DCM Mild (Patients with mild form of DCM). Patients with severe (DCM Severe) and moderate reduction (DCM Mild) in left ventricular function are about as distant from healthy controls. Data based on Geniom microarray analysis assessing 32 patients with mild (moderate) and 21 patients with severe DCM in comparison to 39 healthy controls characterized by normal LVEF (for details see Table 1 in Example 2).
Figure 10:
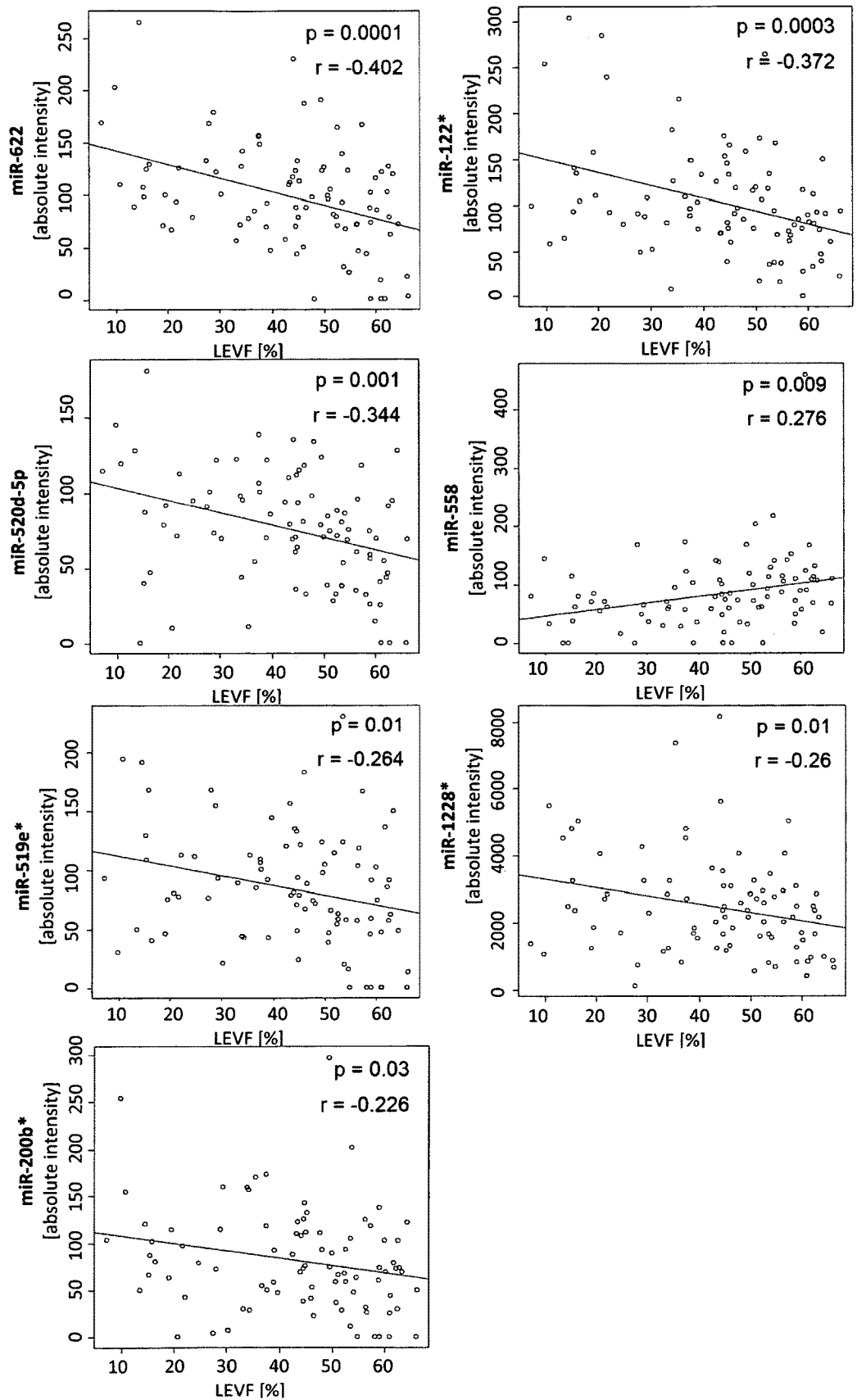
FIG. 10: MiRNA expression levels correlate with disease severity: statistical correlation of miRNA expression to the severity of the disease (DCM), measured by the LVEF (left ventricular ejection fraction). Most promising miRNA candidates are: hsa-miR-622, -520d-5p, -519e*, -200b*, -122*, -558, -1228*. Data based on Geniom microarray analysis assessing 32 patients with mild (moderate) and 21 patients with severe DCM in comparison to 39 healthy controls characterized by normal LVEF (for details see Table 1 in Example 2).

A perfect biomarker not only indicates diseased patients, but also correlates with disease severity. This means that miRNA expression patterns and values might be related to the impairment of cardiac contractility in DCM patients. To visualize such differences in miRNA expression patterns and to show the relation of the different disease stages we computed the principle components of the high-dimensional datasets (FIG. 8). As shown, the expression levels of all studied miRNAs in the control group are most distant from the DCM patients with severely reduced cardiac function. To evaluate whether miRNA expression levels also correlate with disease severity, we performed correlation analysis of single miRNAs and the computed ejection fraction in the ventricular angiography of DCM and control patients. We found a significant correlation of miRNA expression to the disease severity as shown in FIG. 10.

Discussion

The role of miRNAs as biomarkers for cardiovascular disorders is a main focus of current research. In our present study we evaluated the changes of the human miRNome related to non-ischemic heart failure, particularly in DCM patients. We assessed whole blood samples from DCM patients with varying disease severity and found several miRNAs to be dysregaluted in response to DCM, that are even able to discriminate DCM from control patients with high statistic power. Above that, miRNA expressions correlate with disease severity. These results gain even more importance when they are compared to predictive utilities for systolic function of conventional biomarkers. AUC values of e.g. NT-proBNP range from 0.71 to 0.83 (PMID: 16517806; PMID: 18298821). Hence, they are comparable to the here found corresponding values for selected miRNAs, especially when their statistic information is combined in a signature.

It is not surprising that some of the here described miRNAs play a biological role in other diseases than DCM. To our knowledge none of the 8 DCM miRNAs derived from peripheral whole blood were previously found as peripheral biomarker for a specific disease. However, they have a specific function in certain tissues. For instance, miR-558 was correlated to tumor-proliferation in patients with neuroblastoma (PMID: 21498633), miR-520d shows differential regulation in breast cancer (PMID: 22158050), miR-519e* has been shown to have tumor suppressor function in a subset of cancerous diseases (PMID: 19088191), miR-1231 was found to be downregulated in human colon cancer stem cells (PMID: 22180714) and miR-1228* is highly expressed in malignant mesothelioma tissue samples (PMID: 19396864). Hence, the role of a specific miRNA in distinctive tissues may be different.

In another study, Tijsen et al. assessed expression levels of miRNAs in plasma samples from patients with and without heart failure (PMID: 20185794). They found 6 miRNAs to be significantly dysregulated in patients. One of these candidates was miR-622, which we also find to be significantly dysregulated in response to DCM in our present study which was in comparison conducted from peripheral whole blood, representing the cellular fraction (blood cells). The pathophyiological cascades that lead to dysregulation of specific miRNAs in the course of heart failure remains elusive. To date, it is still unknown for most of the here found miRNAs if they are ubiquituously expressed or in a tissue specific manner. Since we drew whole blood rather than serum blood samples from enrolled individuals, it is highly likely that we assessed not only cardiospecific, circulating miRNAs derived from damaged cardiomyocytes. It can be assumed that the here found dysregulated miRNAs reflect a broadened view of the complex pathophysiological cascades that finally lead to DCM and disease progression involving various cell types like cardiomyocates or inflammatory cells. Above that, secondary effects on other organ systems might also lead to miRNA dysregulation, potenially reflecting disease severity. It can be presumed that further miRNAs identified in this study are indeed linked to cardiac impairment. But for all that it can still be assumed that the miRNA expression changes observed in this study are specific to DCM. It was stated in former large multicenter studies that miRNA expression profiles do reliably correlate with the underlying disease (PMID: 21892151). Aside from this, none of the 8 top miRNAs were found to be also dysregulated in response to acute myocardial infarction (AMI) in our former studies assessing whole miRNome alterations in the course of AMI (PMID: 20886220; Vogel et al.).

Therapeutic options in heart failure today are applied in a stepwise manner according to disease severity. Defining which therapeutic approach is appropriate for an individual patient might be difficult. Hence, risk stratification becomes more and more important to identify a patient at risk to receive a specific, maybe expensive or invasive treatment (e.g. an internal cardioverter defibrillator). Several biomarkers have been intensively studied in the past years to predict heart function and cardiac risk, among them cardiac troponin T (cTnT), brain natriuretic peptide (BNP) or atrial natriuretic peptides (Mukoyama PMID: 2143809). We were able to show that miRNA dysregaulation not only indicates diseased patients, but also correlates with disease severity. Hence, our data substantiate the role of miRNAs as novel, additional biomarkers for DCM, the most prevelant form of non-ischemic heart failure. Using a multiple biomarker approach, miRNAs might facilitate early diagnosis, functional assessment, risk stratification and evaluation of disease progression in DCM patients.

The invention claimed is:

1. A method of detecting an expression profile for dilated cardiomyopathy in a subject comprising the steps of:
   (i) providing a blood cell sample comprising a mixture of erythrocytes, leukocytes, and thrombocytes obtained from the subject;
   (ii) detecting whether the expression profile for dilated cardiomyopathy is present in the blood cell sample obtained from the subject by contacting the blood cell sample with probes for a miRNA expression profile and detecting binding between the probes and the miRNAs, wherein the expression profile comprises a set of at least two miRNAs selected from the group consisting of:
   1) miR-520d-5p having SEQ ID No: 1, and
   2) at least one additional miRNA selected from the group consisting of:
   miR-558 having SEQ ID NO: 6,
   miR-122* having SEQ ID NO: 3,
   miR-622 having SEQ ID NO: 24,
   miR-519e* having SEQ ID NO: 34,
   miR-1228* having SEQ ID NO: 30,
   miR-200b* having SEQ ID NO: 14, and
   miR-1231 having SEQ ID NO: 27; and
   (iii) identifying whether the subject has dilated cardiomyopathy by transforming the individual expression levels of the miRNAs in the individual blood cells of the blood cell sample to one numerical value which represents the mathematical average of the miRNA expression levels of the individual blood cells and comparing the expression profile to a reference expression profile obtained from at least one healthy human subject or a human subject not having dilated cardiomyopathy, whereby the difference between expression profile and the reference expression profile is indicative of dilated cardiomyopathy.

2. The method of claim 1, wherein the set of miRNAs comprises at least one of the sets of miRNAs selected from the group consisting of:

DCM-39: hsa-miR-558, hsa-miR-122*, hsa-miR -520d-5p, hsa-miR -622, hsa-miR-519e*, hsa-miR -1228*, hsa-miR -200b*, hsa-miR -1231;
DCM-40: hsa-miR-122*, hsa-miR-1228*;
DCM-41: hsa-miR-122*, hsa-miR-558;
DCM-42: hsa-miR-122*, hsa-miR-519e;
DCM-43: hsa-miR-122*; hsa-miR-622;
DCM-44: hsa-miR-122*, hsa-miR-520d-5p;
DCM-45: hsa-miR-122*, hsa-miR-200b*;
DCM-46: hsa-miR-1228*, hsa-miR-558;
DCM-47: hsa-miR-1228*, hsa-miR-519e*;
DCM-48: hsa-miR-1228*, hsa-miR-622;
DCM-49: hsa-miR-1228*, hsa-miR-520d-5p;
DCM-50: hsa-miR-1228*, hsa-miR-200b*;
DCM-51: hsa-miR-558, hsa-miR-519e*;
DCM-52: hsa-miR-558, hsa-miR-622;
DCM-53: hsa-miR-558, hsa-miR-520d-5p;
DCM-54: hsa-miR-558, hsa-miR-200b*;
DCM-55: hsa-miR-519e*, hsa-miR-622;
DCM-56: hsa-miR-519e*, hsa-miR-520d-5p;
DCM-57: hsa-miR-519e*, hsa-miR-200b*;
DCM-58: hsa-miR-622, hsa-miR-520d-5p;
DCM-59: hsa-miR-622, hsa-miR-200b*;
DCM-60: hsa-miR-122*, hsa-miR-1228*, hsa-miR-558;
DCM-61: hsa-miR-122*, hsa-miR-1228*, hsa-miR-519e*;
DCM-62: hsa-miR-122*, hsa-miR-1228*, hsa-miR-622;
DCM-63: hsa-miR-122*, hsa-miR-1228*, hsa-miR-520d-5p;
DCM-64: hsa-miR-122*, hsa-miR-1228*, hsa-miR-200b*;
DCM-65: hsa-miR-122*, hsa-miR-558, hsa-miR-519e*;
DCM-66: hsa-miR-122*, hsa-miR-558, hsa-miR-622;
DCM-67: hsa-miR-122*, hsa-miR-558, hsa-miR-520d-5p;
DCM-68: hsa-miR-122*, hsa-miR-558, hsa-miR-200b*;
DCM-69: hsa-miR-122*, hsa-miR-519e*, hsa-miR-622;

DCM-70: hsa-miR-122*, hsa-miR-519e*, hsa-miR-520d-5p;
DCM-71: hsa-miR-122*, hsa-miR-519e*, hsa-miR-200b*;
DCM-72: hsa-miR-122*, hsa-miR-622, hsa-miR-520d-5p;
DCM-73: hsa-miR-122*, hsa-miR-622, hsa-miR-200b*;
DCM-74: hsa-miR-122*, hsa-miR-520d-5p, hsa-miR-200b*;
DCM-75: hsa-miR-1228*, hsa-miR-558, hsa-miR-519e*;
DCM-76: hsa-miR-1228*, hsa-miR-558, hsa-miR-622;
DCM-77: hsa-miR-1228*, hsa-miR-558, hsa-miR-520d-5p;
DCM-78: hsa-miR-1228*, hsa-miR-558, hsa-miR-200b*;
DCM-79: hsa-miR-1228*, hsa-miR-519e*, hsa-miR-622;
DCM-80: hsa-miR-1228*, hsa-miR-519e*, hsa-miR-520d-5p;
DCM-81: hsa-miR-1228*, hsa-miR-519e*, hsa-miR-200b*;
DCM-82: hsa-miR-1228*, hsa-miR-622, hsa-miR-520d-5p;
DCM-83: hsa-miR-1228*, hsa-miR-622, hsa-miR-200b*;
DCM-84: hsa-miR-1228*, hsa-miR-520d-5p, hsa-miR-200b*;
DCM-85: hsa-miR-558, hsa-miR-519e*, hsa-miR-622;
DCM-86: hsa-miR-558, hsa-miR-519e*, hsa-miR-520d-5p;
DCM-87: hsa-miR-558, hsa-miR-519e*, hsa-miR-200b*;
DCM-88: hsa-miR-558, hsa-miR-622, hsa-miR-520d-5p;
DCM-89: hsa-miR-558, hsa-miR-622, hsa-miR-200b*;
DCM-90: hsa-miR-558, hsa-miR-520d-5p, hsa-miR-200b*;
DCM-91: hsa-miR-519e*, hsa-miR-622, hsa-miR-520d-5p;
DCM-92: hsa-miR-519e*, hsa-miR-622, hsa-miR-200b*;
DCM-93: hsa-miR-519e*, hsa-miR-520d-5p, hsa-miR-200b*; and
DCM-94: hsa-miR-622, hsa-miR-520d-5p, hsa-miR-200b*.

\* \* \* \* \*